US007981446B2

(12) United States Patent
Lee et al.

(10) Patent No.: US 7,981,446 B2
(45) Date of Patent: Jul. 19, 2011

(54) PHARMACEUTICAL COMPOSITIONS AND METHODS FOR DELIVERING NUCLEIC ACIDS INTO CELLS

(75) Inventors: Sang-Kyou Lee, Seoul (KR); Seung-Kyou Lee, Seoul (KR); Ki-Doo Choi, Seoul (KR)

(73) Assignee: ForHumanTech. Co., Ltd. (KR)

( * ) Notice: Subject to any disclaimer, the term of this patent is extended or adjusted under 35 U.S.C. 154(b) by 0 days.

(21) Appl. No.: 12/277,000

(22) Filed: Nov. 24, 2008

(65) Prior Publication Data

US 2009/0162857 A1    Jun. 25, 2009

Related U.S. Application Data

(60) Provisional application No. 60/990,124, filed on Nov. 26, 2007.

(51) Int. Cl.
*A61K 9/16* (2006.01)
*A61K 48/00* (2006.01)
*A61K 35/16* (2006.01)
*C12N 15/87* (2006.01)

(52) U.S. Cl. .......... 424/491; 435/459; 514/44; 530/358; 977/773; 977/906; 977/916

(58) Field of Classification Search .................. None
See application file for complete search history.

(56) References Cited

U.S. PATENT DOCUMENTS

| | | | | |
|---|---|---|---|---|
| 5,447,860 | A * | 9/1995 | Ziegler | 435/363 |
| 6,025,140 | A | 2/2000 | Langel et al. | |
| 6,103,521 | A * | 8/2000 | Capon et al. | 435/325 |
| 6,166,191 | A | 12/2000 | Randazzo | |
| 6,251,599 | B1 * | 6/2001 | Chen et al. | 435/6 |
| 6,903,077 | B1 * | 6/2005 | Heintz | 514/44 R |
| 7,332,474 | B2 * | 2/2008 | Min et al. | 514/13 |
| 2003/0104622 | A1 | 6/2003 | Robbins et al. | |
| 2003/0125242 | A1 * | 7/2003 | Rosenecker et al. | 514/8 |
| 2003/0139365 | A1 * | 7/2003 | Lo et al. | 514/44 |
| 2003/0229202 | A1 | 12/2003 | Guo et al. | |
| 2005/0014791 | A1 | 1/2005 | Tsantrizos et al. | |
| 2005/0090646 | A1 | 4/2005 | Sullivan | |
| 2005/0158373 | A1 | 7/2005 | Szeto et al. | |
| 2006/0035815 | A1 * | 2/2006 | Chen et al. | 514/7 |
| 2006/0041058 | A1 | 2/2006 | Yin et al. | |
| 2006/0148060 | A1 | 7/2006 | Lee et al. | |
| 2007/0105775 | A1 | 5/2007 | Lee et al. | |
| 2008/0132450 | A1 | 6/2008 | Lee et al. | |
| 2009/0087422 | A1 | 4/2009 | Lee et al. | |

FOREIGN PATENT DOCUMENTS

| | | |
|---|---|---|
| WO | WO 98/07858 A1 | 2/1998 |
| WO | WO 98/07860 A1 | 2/1998 |
| WO | WO 03/059940 A1 | 7/2003 |
| WO | WO 03/059941 A1 | 7/2003 |
| WO | WO 2004/044008 A1 | 5/2004 |
| WO | WO 2004/078933 A2 | 9/2004 |
| WO | WO 2007/052172 A2 | 5/2007 |

OTHER PUBLICATIONS

Hashida et al (Br. J. Cancer 90: 1252-1258, 2004).*
Segura et al (Bioconj. Chem. 18: 736-745, 2007).*
Su et al (Infection and Immunity 59(10): 3811-3814, 1991).*
Alkema, M.J., et al., "Identification of Bmi1-interacting proteins as constituents of a multimeric mammalian Polycomb complex," *Genes & Dev.* 11:226-240, Cold Spring Harbor Laboratory Press (1997).
Asemu, G., et al., "Identification of the changes in phospholipase C isozymes in ischemic-reperfused rat heart," *Arch. Biochem. Biophys.* 411:174-182, Elsevier Science (2003).
Chiu, Y.-L., et al., "Visualizing a Correlation between siRNA Localization, Cellular Uptake, and RNAi in Living Cells," *Chem. Bio.* 11:1165-1172, Elsevier Ltd. (2004).
Choi, H.S., et al., "Transduced Tat-α-Synuclein Protects against Oxidative Stress In vitro and In vivo," *J. Biochem. Mol. Biol.* 39:253-262, Korean Society for Biochemistry and Molecular Biology (May 2006).
Davidson, T.J., et al., "Highly Efficient Small Interfering RNA Delivery to Primary Mammalian Neurons Induces MicroRNA-Like Effects before mRNA Degradation," *J. Neurosci.* 24:10040-10046, Society for Neuroscience (2004).
Dent, M.R., et al., "Phospholipase C gene expression, protein content, and activities in cardiac hyperthrophy and heart failure due to volume overload," *Am. J. Physiol. Heart Circ. Physiol.* 287:H719-H727, The American Physiological Society (2004).
Dietz, G.P.H., et al., "Inhibition of Neuronal Apoptosis in Vitro and in Vivo Using TAT-Mediated Protein Transduction," *Mol. Cell. Neurosci.* 21:29-37, Elsevier Science (2002).
Dom, G., et al., "Cellular uptake of Antennapedia Penetratin peptides is a two-step process in which phase transfer precedes a tryptophan-dependent translocation," *Nucleic Acids Res.* 31:556-561, Oxford University Press (2003).
Eom, K.D., et al., "A Facile Synthesis and Physical Properties of Nano-Sized Dendritic α,ε-Poly(L-lysine)s for the Delivery of Nucleic Acids," *J. Nanosci. Nanotech.* 6:3532-3538, American Scientific Publishers (Nov. 2006).
Gunster, M.J., et al., "Identification and Characterization of Interactions between the Vertebrate Polycomb-Group Protein BMI1 and Human Homologs of Polyhomeotic," *Mol. Cell. Biol* 17:2326-2335, American Society for Microbiology (1997).
Krief, S., et al., "Identification and Characterization of cvHSP," *J. Biol. Chem.* 274:36592-36600, The American Society for Biochemistry and Molecular Biology, Inc. (1999).

(Continued)

*Primary Examiner* — Richard Schnizer
(74) *Attorney, Agent, or Firm* — Sterne Kessler Goldstein & Fox, P.L.L.C.

(57) ABSTRACT

The present invention relates to methods of delivering nucleic acids into cells using a nucleic acid binding molecule containing a multimeric or spacer-incorporated protein transduction domain (PTD). The invention also relates to novel compositions that contain a nucleic acid complexed or conjugated with a nucleic acid binding molecule. The nucleic acid binding molecule may contain a multimeric or spacer-incorporated PTD, and may further contain a nucleic acid binding region. The nucleic acid complexes or conjugations of the present invention may be employed to inhibit expression of a target gene, and/or determine the function of a target gene.

29 Claims, 16 Drawing Sheets

OTHER PUBLICATIONS

Kühnel, F., et al., "Protein Transduction Domains Fused to Virus Receptors Improve Cellular Virus Uptake and Enhance Oncolysis by Tumor-Specific Replicating Vectors," *J. Virol.* 78:13743-13754, American Society for Microbiology (2004).

Lai, Y., et al., "Selectively increasing inducible heat shock protein 70 via TAT-protein transduction protects neurons from nitrosative stress and excitotoxicity," *J. Neurochem*. 94:360-366, International Society for Neurochemistry (2005).

Lee, K-M., et al., "Molecular Basis of T Cell Inactivation by CTLA-4," *Science* 282:2263-2266, American Association for the Advancement of Science (1998).

Morris, M.C., et al., "A new peptide vector for efficient delivery of oligonucleotides into mammalian cells," *Nucleic Acids Res*. 25:2730-2736, Oxford University Press (1997).

Morris, M.C., et al., "A non-covalent peptide-based carrier for in vivo delivery of DNA mimics," *Nucleic Acids Res*. 35:e49, 1-10, Oxford University Press (Mar. 2007).

Moschos, S.A., et al., "Cell-penetrating-peptide-mediated siRNA lung delivery," *Biochem. Soc. Trans*. 35:807-810, Biochemical Society (Apr. 2007).

Muratovsk, A., and Eccles, M.R., "Conjugate for efficient delivery of short interfering RNA (siRNA) into mammalian cels," *FEBS Lett*. 558:63-68, Elsevier B.V. (2004).

Mangat, R., et al., "Inhibition of phospholipase C-$\gamma_1$ augments the decrease in cardiomyocyte viability by $H_2O_2$," *Am. J. Physiol. Heart Circ. Physiol*. 291:H854-H860, The American Physiological Society (Feb. 2006).

Noguchi, H., et al., "A new cell-permeable peptide allows successful allogenic islet transplantation in mice," *Nat. Med*. 10:305-309, Nature Publishing Company (2004).

Ohta, H., et al., "Structure and Chromosomal Localization of the *RAE28/HPH1* Gene, a Human Homologue of the *Polyhomeotic* Gene," *DNA Seq*. 11:61-73, (OPA) Overseas Publishers Association N.V. (2000).

Rudolph, C., et al., "Oligomers of the Arginine-rich Motif of the HIV-1 TAT protein Are Capable of Transferring Plasmid DNA into Cells," *J. Biol. Chem*. 278:11411-11418, The American Society for Biochemistry and Molecular Biology, Inc. (2003).

Torchilin, V.P., et al., "TAT peptide on the surface of liposomes affords their efficient intracellular delivery even at low temperature and in the presence of metabolic inhibitors," *Proc. Natl. Acad. Sci. USA* 98:8786-8791, National Academy of Sciences (2001).

Torchilin, V.P., et al., "Cell transfection in vitro and in vivo with nontoxic TAT peptide-liposome-DNA complexes," *Proc. Natl. Acad. Sci. USA* 100:1972-1977, National Academy of Sciences (2003).

Viehl, C.T., et al., "A Tat Fusion Protein-Based Tumor Vaccine for Breast Cancer," *Ann. Surg. Oncol*. 12:517-525, Society of Surgical Oncology, Inc. (2005).

Wheeler, D.S., et al., "Intracellular delivery of HSP70 using HIV-1 Tat protein transduction domain," *Biochem. Biophys. Res. Commun*. 301:54-59, Elsevier Science (2003).

Yagisawa, H., "Nucleocytoplasmic Shuttling of Phospholipase C-$\delta_1$: A Link to $Ca^{2+}$," *J. Cell. Biochem*. 97:233-243, Wiley-Liss, Inc. (2005).

International Search Report for International Application No. PCT/IB2006/003971, Korean Intellectual Property Office, Republic of Korea, mailed on Sep. 19, 2007.

International Search Report for International Application No. PCT/IB2007/003404, Korean Patent Office, Republic of Korea, mailed on May 2, 2008.

International Search Report for International Application No. PCT/IB2007/004189, Korean Patent Office, Republic of Korea, mailed on Jun. 9, 2008.

International Search Report for International Application No. PCT/KR03/00122, Korean Intellectual Property Office, Republic of Korean, mailed on May 14, 2003.

Office Action mailed on Jul. 3, 2006 in U.S. Appl. No. 11/267,817, Lee, S.-K., et al., filed Nov. 7, 2005.

Office Action mailed on Aug. 10, 2007 Jan. 12, 2007 in U.S. Appl. No. 11/267,817, Lee, S.-K., et al., filed Nov. 7, 2005.

Office Action mailed on Dec. 12, 2007 in U.S. Appl. No. 11/267,817, Lee, S.-K., et al., filed Nov. 7, 2005.

Office Action mailed on May 12, 2008 in U.S. Appl. No. 11/267,817, Lee, S.-K., et al., filed Nov. 7, 2005.

Office Action mailed on Jan. 7, 2009 in U.S. Appl. No. 11/267,817, Lee, S.-K., et al., filed Nov. 7, 2005.

Office Action mailed on Feb. 26, 2009 in U.S. Appl. No. 11/592,227, Lee, S.-K., et al., filed Nov. 3, 2006.

* cited by examiner

SEQUENCE LISTING

<160> NUMBER OF SEQ ID NOS: 60

<210> SEQ ID NO 1
<211> LENGTH: 11
<212> TYPE: PRT
<213> ORGANISM: Homo sapiens

<400> SEQUENCE: 1

Tyr Ala Arg Val Arg Arg Arg Gly Pro Arg Arg
1               5                   10

<210> SEQ ID NO 2
<211> LENGTH: 11
<212> TYPE: PRT
<213> ORGANISM: Human immunodeficiency virus

<400> SEQUENCE: 2

Tyr Gly Arg Lys Lys Arg Arg Gln Arg Arg Arg
1               5                   10

<210> SEQ ID NO 3
<211> LENGTH: 16
<212> TYPE: PRT
<213> ORGANISM: Drosophila sp.

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 27
<212> TYPE: PRT
<213> ORGANISM: Homo sapiens

<400> SEQUENCE: 4

Cys Leu Ile Lys Lys Ala Leu Ala Ala Leu Ala Lys Leu Asn Ile Lys
1               5                   10                  15

Leu Leu Tyr Gly Ala Ser Asn Leu Thr Trp Gly
            20                  25

<210> SEQ ID NO 5
<211> LENGTH: 34
<212> TYPE: PRT
<213> ORGANISM: herpes simplex virus

<400> SEQUENCE: 5

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 6
<211> LENGTH: 7
<212> TYPE: PRT
<213> ORGANISM: Homo sapiens

<400> SEQUENCE: 6

Arg Arg Arg Arg Arg Arg Arg
1               5

<210> SEQ ID NO 7

```
<211> LENGTH: 24
<212> TYPE: PRT
<213> ORGANISM: Artificial
<220> FEATURE:
<223> OTHER INFORMATION: Synthetic MPH

<400> SEQUENCE: 7

Tyr Ala Arg Val Arg Arg Arg Gly Pro Arg Arg Gly Gly Tyr Ala Arg
1               5                   10                  15

Val Arg Arg Arg Gly Pro Arg Arg
            20

<210> SEQ ID NO 8
<211> LENGTH: 26
<212> TYPE: PRT
<213> ORGANISM: Homo sapiens

<400> SEQUENCE: 8

Ala Ala Val Ala Leu Leu Pro Ala Val Leu Leu Ala Leu Leu Ala Pro
1               5                   10                  15

Ala Ala Ala Asp Gln Asn Gln Leu Met Pro
            20                  25

<210> SEQ ID NO 9
<211> LENGTH: 21
<212> TYPE: PRT
<213> ORGANISM: Homo sapiens

<400> SEQUENCE: 9

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 10
<211> LENGTH: 21
<212> TYPE: PRT
<213> ORGANISM: Homo sapiens

<400> SEQUENCE: 10

Lys Glu Thr Trp Phe Glu Thr Trp Phe Thr Glu Trp Ser Gln Pro Lys
1               5                   10                  15

Lys Lys Arg Lys Val
            20

<210> SEQ ID NO 11
<211> LENGTH: 19
<212> TYPE: PRT
<213> ORGANISM: Homo sapiens

<400> SEQUENCE: 11

Tyr Gly Phe Lys Lys Phe Arg Lys Pro Trp Thr Trp Trp Glu Thr Trp
1               5                   10                  15

Trp Thr Glu

<210> SEQ ID NO 12
<211> LENGTH: 9
<212> TYPE: PRT
<213> ORGANISM: Homo sapiens

<400> SEQUENCE: 12

Ala Lys Ala Ala Arg Gln Ala Ala Arg
1               5
```

-continued

```
<210> SEQ ID NO 13
<211> LENGTH: 27
<212> TYPE: PRT
<213> ORGANISM: Artificial
<220> FEATURE:
<223> OTHER INFORMATION: Synthetic MPG

<400> SEQUENCE: 13

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 14
<211> LENGTH: 30
<212> TYPE: PRT
<213> ORGANISM: Artificial
<220> FEATURE:
<223> OTHER INFORMATION: Synthetic KALA

<400> SEQUENCE: 14

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 15
<211> LENGTH: 12
<212> TYPE: PRT
<213> ORGANISM: Artificial
<220> FEATURE:
<223> OTHER INFORMATION: Synthetic MPH-1-PTD monomer

<400> SEQUENCE: 15

Tyr Ala Arg Val Arg Arg Arg Gly Pro Arg Arg Cys
1               5                   10

<210> SEQ ID NO 16
<211> LENGTH: 27
<212> TYPE: PRT
<213> ORGANISM: Artificial
<220> FEATURE:
<223> OTHER INFORMATION: Synthetic MPH-1-PTD dimer a

<400> SEQUENCE: 16

Tyr Ala Arg Val Arg Arg Arg Gly Pro Arg Arg Gly Gly Tyr Ala Arg
1               5                   10                  15

Val Arg Arg Arg Gly Pro Arg Arg Gly Gly Cys
            20                  25

<210> SEQ ID NO 17
<211> LENGTH: 30
<212> TYPE: PRT
<213> ORGANISM: Artificial
<220> FEATURE:
<223> OTHER INFORMATION: Synthetic MPH-1-PTD dimer b

<400> SEQUENCE: 17

Cys Gly Gly Tyr Ala Arg Val Arg Arg Arg Gly Pro Arg Arg Gly Gly
1               5                   10                  15

Tyr Ala Arg Val Arg Arg Arg Gly Pro Arg Arg Gly Gly Cys
            20                  25                  30

<210> SEQ ID NO 18
<211> LENGTH: 37
```

```
<212> TYPE: PRT
<213> ORGANISM: Artificial
<220> FEATURE:
<223> OTHER INFORMATION: Synthetic MPH-1-PTD trimer

<400> SEQUENCE: 18

Tyr Ala Arg Val Arg Arg Gly Pro Arg Arg Gly Tyr Ala Arg Val
1               5                   10                  15

Arg Arg Arg Gly Pro Arg Arg Gly Tyr Ala Arg Val Arg Arg Gly
                20                  25                  30

Pro Arg Arg Gly Cys
            35

<210> SEQ ID NO 19
<211> LENGTH: 36
<212> TYPE: PRT
<213> ORGANISM: Artificial
<220> FEATURE:
<223> OTHER INFORMATION: Synthetic recombinant MPH-1-PTD dimer

<400> SEQUENCE: 19

Tyr Arg Phe Tyr Ala Arg Val Arg Arg Arg Gly Pro Arg Arg Gly Gly
1               5                   10                  15

Ala Arg Phe Tyr Ala Arg Val Arg Arg Gly Pro Arg Arg Gly Gly
                20                  25                  30

Ala Arg Val Cys
            35

<210> SEQ ID NO 20
<211> LENGTH: 68
<212> TYPE: PRT
<213> ORGANISM: Artificial
<220> FEATURE:
<223> OTHER INFORMATION: Synthetic recombinant MPH-1-PTD tetramer

<400> SEQUENCE: 20

Tyr Arg Phe Tyr Ala Arg Val Arg Arg Arg Gly Pro Arg Arg Gly Gly
1               5                   10                  15

Ala Arg Phe Tyr Ala Arg Val Arg Arg Gly Pro Arg Arg Gly Gly
                20                  25                  30

Ala Arg Phe Tyr Ala Arg Val Arg Arg Gly Pro Arg Arg Gly Gly
            35                  40                  45

Ala Arg Phe Tyr Ala Arg Val Arg Arg Gly Pro Arg Arg Gly Gly
        50                  55                  60

Ala Arg Val Cys
65

<210> SEQ ID NO 21
<211> LENGTH: 132
<212> TYPE: PRT
<213> ORGANISM: Artificial
<220> FEATURE:
<223> OTHER INFORMATION: Synthetic recombinant MPH-1-PTD octamer

<400> SEQUENCE: 21

Tyr Arg Phe Tyr Ala Arg Val Arg Arg Arg Gly Pro Arg Arg Gly Gly
1               5                   10                  15

Ala Arg Phe Tyr Ala Arg Val Arg Arg Gly Pro Arg Arg Gly Gly
                20                  25                  30

Ala Arg Phe Tyr Ala Arg Val Arg Arg Gly Pro Arg Arg Gly Gly
            35                  40                  45

Ala Arg Phe Tyr Ala Arg Val Arg Arg Gly Pro Arg Arg Gly Gly
```

```
                    50                  55                  60
Tyr Arg Phe Tyr Ala Arg Val Arg Arg Gly Pro Arg Arg Gly Gly
 65                  70                  75                  80

Ala Arg Phe Tyr Ala Arg Val Arg Arg Gly Pro Arg Arg Gly Gly
                     85                  90                  95

Ala Arg Phe Tyr Ala Arg Val Arg Arg Gly Pro Arg Arg Gly Gly
                    100                 105                 110

Ala Arg Phe Tyr Ala Arg Val Arg Arg Gly Pro Arg Arg Gly Gly
                    115                 120                 125

Ala Arg Val Cys
    130

<210> SEQ ID NO 22
<211> LENGTH: 24
<212> TYPE: PRT
<213> ORGANISM: Artificial
<220> FEATURE:
<223> OTHER INFORMATION: Synthetic TAT (homodimer)

<400> SEQUENCE: 22

Tyr Gly Arg Lys Lys Arg Arg Gln Arg Arg Gly Gly Tyr Gly Arg
  1               5                  10                  15

Lys Lys Arg Arg Gln Arg Arg Arg
                 20

<210> SEQ ID NO 23
<211> LENGTH: 34
<212> TYPE: PRT
<213> ORGANISM: Artificial
<220> FEATURE:
<223> OTHER INFORMATION: Synthetic penetratin (homodimer)

<400> SEQUENCE: 23

Arg Gln Ile Lys Ile Trp Phe Gln Asn Arg Arg Met Lys Trp Lys Lys
  1               5                  10                  15

Gly Gly Arg Gln Ile Lys Ile Trp Phe Gln Asn Arg Arg Met Lys Trp
                 20                  25                  30

Lys Lys

<210> SEQ ID NO 24
<211> LENGTH: 44
<212> TYPE: PRT
<213> ORGANISM: Artificial
<220> FEATURE:
<223> OTHER INFORMATION: Synthetic Pep-1 (homodimer)

<400> SEQUENCE: 24

Lys Glu Thr Trp Trp Glu Thr Trp Trp Thr Glu Trp Ser Gln Pro Lys
  1               5                  10                  15

Lys Lys Arg Lys Val Gly Gly Lys Glu Thr Trp Trp Glu Thr Trp Trp
                 20                  25                  30

Thr Glu Trp Ser Gln Pro Lys Lys Lys Arg Lys Val
            35                  40

<210> SEQ ID NO 25
<211> LENGTH: 24
<212> TYPE: PRT
<213> ORGANISM: Artificial
<220> FEATURE:
<223> OTHER INFORMATION: Synthetic MPH + TAT

<400> SEQUENCE: 25
```

```
Tyr Ala Arg Val Arg Arg Arg Gly Pro Arg Arg Gly Tyr Gly Arg
1               5                   10                  15

Lys Lys Arg Arg Gln Arg Arg Arg
            20
```

<210> SEQ ID NO 26
<211> LENGTH: 29
<212> TYPE: PRT
<213> ORGANISM: Artificial
<220> FEATURE:
<223> OTHER INFORMATION: Synthetic MPH + penetratin

<400> SEQUENCE: 26

```
Tyr Ala Arg Val Arg Arg Arg Gly Pro Arg Arg Gly Gly Arg Gln Ile
1               5                   10                  15

Lys Ile Trp Phe Gln Asn Arg Arg Met Lys Trp Lys Lys
            20                  25
```

<210> SEQ ID NO 27
<211> LENGTH: 34
<212> TYPE: PRT
<213> ORGANISM: Artificial
<220> FEATURE:
<223> OTHER INFORMATION: Synthetic MPH + Pep-1

<400> SEQUENCE: 27

```
Tyr Ala Arg Val Arg Arg Arg Gly Pro Arg Arg Gly Gly Lys Glu Thr
1               5                   10                  15

Trp Trp Glu Thr Trp Trp Thr Glu Trp Ser Gln Pro Lys Lys Lys Arg
            20                  25                  30

Lys Val
```

<210> SEQ ID NO 28
<211> LENGTH: 29
<212> TYPE: PRT
<213> ORGANISM: Artificial
<220> FEATURE:
<223> OTHER INFORMATION: Synthetic TAT + penetratin

<400> SEQUENCE: 28

```
Tyr Ala Arg Val Arg Arg Arg Gly Pro Arg Arg Gly Gly Arg Gln Ile
1               5                   10                  15

Lys Ile Trp Phe Gln Asn Arg Arg Met Lys Trp Lys Lys
            20                  25
```

<210> SEQ ID NO 29
<211> LENGTH: 34
<212> TYPE: PRT
<213> ORGANISM: Artificial
<220> FEATURE:
<223> OTHER INFORMATION: Synthetic TAT + Pep-1

<400> SEQUENCE: 29

```
Tyr Ala Arg Val Arg Arg Arg Gly Pro Arg Arg Gly Gly Lys Glu Thr
1               5                   10                  15

Trp Trp Glu Thr Trp Trp Thr Glu Trp Ser Gln Pro Lys Lys Lys Arg
            20                  25                  30

Lys Val
```

<210> SEQ ID NO 30
<211> LENGTH: 39
<212> TYPE: PRT
<213> ORGANISM: Artificial
<220> FEATURE:

<223> OTHER INFORMATION: Synthetic penetratin + Pep-1

<400> SEQUENCE: 30

Arg Gln Ile Lys Ile Trp Phe Gln Asn Arg Arg Met Lys Trp Lys Lys
1               5                   10                  15

Gly Gly Lys Glu Thr Trp Trp Glu Thr Trp Trp Thr Glu Trp Ser Gln
            20                  25                  30

Pro Lys Lys Lys Arg Lys Val
        35

<210> SEQ ID NO 31
<211> LENGTH: 68
<212> TYPE: PRT
<213> ORGANISM: Artificial
<220> FEATURE:
<223> OTHER INFORMATION: Synthetic TAT (homotetramer)

<400> SEQUENCE: 31

Tyr Arg Phe Tyr Gly Arg Lys Lys Arg Arg Gln Arg Arg Gly Gly
1               5                   10                  15

Ala Arg Phe Tyr Gly Arg Lys Lys Arg Arg Gln Arg Arg Gly Gly
            20                  25                  30

Ala Arg Phe Tyr Gly Arg Lys Lys Arg Arg Gln Arg Arg Gly Gly
        35                  40                  45

Ala Arg Phe Tyr Gly Arg Lys Lys Arg Arg Gln Arg Arg Gly Gly
    50                  55                  60

Ala Arg Val Cys
65

<210> SEQ ID NO 32
<211> LENGTH: 88
<212> TYPE: PRT
<213> ORGANISM: Artificial
<220> FEATURE:
<223> OTHER INFORMATION: Synthetic penetratin (homotetramer)

<400> SEQUENCE: 32

Tyr Arg Phe Arg Gln Ile Lys Ile Trp Phe Gln Asn Arg Arg Met Lys
1               5                   10                  15

Trp Lys Lys Gly Gly Ala Arg Phe Arg Gln Ile Lys Ile Trp Phe Gln
            20                  25                  30

Asn Arg Arg Met Lys Trp Lys Lys Gly Gly Ala Arg Phe Arg Gln Ile
        35                  40                  45

Lys Ile Trp Phe Gln Asn Arg Arg Met Lys Trp Lys Lys Gly Gly Ala
    50                  55                  60

Arg Phe Arg Gln Ile Lys Ile Trp Phe Gln Asn Arg Arg Met Lys Trp
65                  70                  75                  80

Lys Lys Gly Gly Ala Arg Val Cys
            85

<210> SEQ ID NO 33
<211> LENGTH: 68
<212> TYPE: PRT
<213> ORGANISM: Artificial
<220> FEATURE:
<223> OTHER INFORMATION: Synthetic MPH + TAT (heterotetramer)

<400> SEQUENCE: 33

Tyr Arg Phe Tyr Ala Arg Val Arg Arg Arg Gly Pro Arg Arg Gly Gly
1               5                   10                  15

Ala Arg Phe Tyr Ala Arg Val Arg Arg Arg Gly Pro Arg Arg Gly Gly

```
                  20                  25                  30

Ala Arg Phe Tyr Gly Arg Lys Lys Arg Gln Arg Arg Gly Gly
            35                  40                  45

Ala Arg Phe Tyr Gly Arg Lys Lys Arg Gln Arg Arg Gly Gly
            50                  55                  60

Ala Arg Val Cys
65

<210> SEQ ID NO 34
<211> LENGTH: 78
<212> TYPE: PRT
<213> ORGANISM: Artificial
<220> FEATURE:
<223> OTHER INFORMATION: Synthetic MPH + penetratin (heterotetramer)

<400> SEQUENCE: 34

Tyr Arg Phe Tyr Ala Arg Val Arg Arg Arg Gly Pro Arg Arg Gly Gly
1               5                   10                  15

Ala Arg Phe Tyr Ala Arg Val Arg Arg Arg Gly Pro Arg Arg Gly Gly
                20                  25                  30

Ala Arg Phe Arg Gln Ile Lys Ile Trp Phe Gln Asn Arg Arg Met Lys
            35                  40                  45

Trp Lys Lys Gly Gly Ala Arg Phe Arg Gln Ile Lys Ile Trp Phe Gln
        50                  55                  60

Asn Arg Arg Met Lys Trp Lys Lys Gly Gly Ala Arg Val Cys
65                  70                  75

<210> SEQ ID NO 35
<211> LENGTH: 78
<212> TYPE: PRT
<213> ORGANISM: Artificial
<220> FEATURE:
<223> OTHER INFORMATION: Synthetic TAT + penetratin (heterotetramer)

<400> SEQUENCE: 35

Tyr Arg Phe Tyr Gly Arg Lys Lys Arg Gln Arg Arg Gly Gly
1               5                   10                  15

Ala Arg Phe Tyr Gly Arg Lys Lys Arg Gln Arg Arg Gly Gly
                20                  25                  30

Ala Arg Phe Arg Gln Ile Lys Ile Trp Phe Gln Asn Arg Arg Met Lys
            35                  40                  45

Trp Lys Lys Gly Gly Ala Arg Phe Arg Gln Ile Lys Ile Trp Phe Gln
        50                  55                  60

Asn Arg Arg Met Lys Trp Lys Lys Gly Gly Ala Arg Val Cys
65                  70                  75

<210> SEQ ID NO 36
<211> LENGTH: 73
<212> TYPE: PRT
<213> ORGANISM: Artificial
<220> FEATURE:
<223> OTHER INFORMATION: Synthetic MPH + TAT + penetratin
      (heterotetramer)

<400> SEQUENCE: 36

Tyr Arg Phe Tyr Ala Arg Val Arg Arg Arg Gly Pro Arg Arg Gly Gly
1               5                   10                  15

Ala Arg Phe Tyr Ala Arg Val Arg Arg Arg Gly Pro Arg Arg Gly Gly
                20                  25                  30

Ala Arg Phe Tyr Gly Arg Lys Lys Arg Gln Arg Arg Gly Gly
            35                  40                  45
```

```
Ala Arg Phe Arg Gln Ile Lys Ile Trp Phe Gln Asn Arg Arg Met Lys
    50                  55                  60

Trp Lys Lys Gly Gly Ala Arg Val Cys
65                  70
```

<210> SEQ ID NO 37
<211> LENGTH: 100
<212> TYPE: PRT
<213> ORGANISM: Artificial
<220> FEATURE:
<223> OTHER INFORMATION: Synthetic MPH (homohexamer)

<400> SEQUENCE: 37

```
Tyr Arg Phe Tyr Ala Arg Val Arg Arg Gly Pro Arg Arg Gly Gly
1               5                   10                  15

Ala Arg Phe Tyr Ala Arg Val Arg Arg Gly Pro Arg Arg Gly Gly
                20                  25                  30

Ala Arg Phe Tyr Ala Arg Val Arg Arg Gly Pro Arg Arg Gly Gly
            35                  40                  45

Ala Arg Phe Tyr Ala Arg Val Arg Arg Gly Pro Arg Arg Gly Gly
    50                  55                  60

Ala Arg Phe Tyr Ala Arg Val Arg Arg Gly Pro Arg Arg Gly Gly
65                  70                  75                  80

Ala Arg Phe Tyr Ala Arg Val Arg Arg Gly Pro Arg Arg Gly Gly
                85                  90                  95

Ala Arg Val Cys
        100
```

<210> SEQ ID NO 38
<211> LENGTH: 100
<212> TYPE: PRT
<213> ORGANISM: Artificial
<220> FEATURE:
<223> OTHER INFORMATION: Synthetic TAT (homohexamer)

<400> SEQUENCE: 38

```
Tyr Arg Phe Tyr Gly Arg Lys Lys Arg Arg Gln Arg Arg Gly Gly
1               5                   10                  15

Ala Arg Phe Tyr Gly Arg Lys Lys Arg Arg Gln Arg Arg Gly Gly
                20                  25                  30

Ala Arg Phe Tyr Gly Arg Lys Lys Arg Arg Gln Arg Arg Gly Gly
            35                  40                  45

Ala Arg Phe Tyr Gly Arg Lys Lys Arg Arg Gln Arg Arg Tyr Gly
    50                  55                  60

Arg Lys Lys Arg Arg Gln Arg Arg Gly Gly Ala Arg Phe Tyr Gly
65                  70                  75                  80

Arg Lys Lys Arg Arg Gln Arg Arg Gly Gly Ala Arg Phe Gly Gly
                85                  90                  95

Ala Arg Val Cys
        100
```

<210> SEQ ID NO 39
<211> LENGTH: 130
<212> TYPE: PRT
<213> ORGANISM: Artificial
<220> FEATURE:
<223> OTHER INFORMATION: Synthetic penetratin (homohexamer)

<400> SEQUENCE: 39

```
Tyr Arg Phe Arg Gln Ile Lys Ile Trp Phe Gln Asn Arg Arg Met Lys
```

```
                1               5              10              15
Trp Lys Lys Gly Gly Ala Arg Phe Arg Gln Ile Lys Ile Trp Phe Gln
                    20                  25                  30

Asn Arg Arg Met Lys Trp Lys Lys Gly Gly Ala Arg Phe Arg Gln Ile
                    35                  40                  45

Lys Ile Trp Phe Gln Asn Arg Arg Met Lys Trp Lys Lys Gly Gly Ala
                    50                  55                  60

Arg Phe Arg Gln Ile Lys Ile Trp Phe Gln Asn Arg Arg Met Lys Trp
 65                  70                  75                  80

Lys Lys Gly Gly Ala Arg Phe Arg Gln Ile Lys Ile Trp Phe Gln Asn
                    85                  90                  95

Arg Arg Met Lys Trp Lys Lys Gly Gly Ala Arg Phe Arg Gln Ile Lys
                   100                 105                 110

Ile Trp Phe Gln Asn Arg Arg Met Lys Trp Lys Lys Gly Gly Ala Arg
                   115                 120                 125

Val Cys
    130

<210> SEQ ID NO 40
<211> LENGTH: 100
<212> TYPE: PRT
<213> ORGANISM: Artificial
<220> FEATURE:
<223> OTHER INFORMATION: Synthetic MPH + TAT + MPH (heterohexamer)

<400> SEQUENCE: 40

Tyr Arg Phe Tyr Ala Arg Val Arg Arg Gly Pro Arg Arg Gly Gly
 1               5                  10                  15

Ala Arg Phe Tyr Ala Arg Val Arg Arg Gly Pro Arg Arg Gly Gly
                    20                  25                  30

Ala Arg Phe Tyr Gly Arg Lys Lys Arg Arg Gln Arg Arg Gly Gly
                    35                  40                  45

Ala Arg Phe Tyr Gly Arg Lys Lys Arg Arg Gln Arg Arg Gly Gly
                    50                  55                  60

Ala Arg Phe Tyr Ala Arg Val Arg Arg Gly Pro Arg Arg Gly Gly
 65                  70                  75                  80

Ala Arg Phe Tyr Ala Arg Val Arg Arg Gly Pro Arg Arg Gly Gly
                    85                  90                  95

Ala Arg Val Cys
            100

<210> SEQ ID NO 41
<211> LENGTH: 110
<212> TYPE: PRT
<213> ORGANISM: Artificial
<220> FEATURE:
<223> OTHER INFORMATION: Synthetic MPH + TAT + penetratin
      (heterohexamer)

<400> SEQUENCE: 41

Tyr Arg Phe Tyr Ala Arg Val Arg Arg Gly Pro Arg Arg Gly Gly
 1               5                  10                  15

Ala Arg Phe Tyr Ala Arg Val Arg Arg Gly Pro Arg Arg Gly Gly
                    20                  25                  30

Ala Arg Phe Tyr Gly Arg Lys Lys Arg Arg Gln Arg Arg Gly Gly
                    35                  40                  45

Ala Arg Phe Tyr Gly Arg Lys Lys Arg Arg Gln Arg Arg Gly Gly
                    50                  55                  60
```

```
Ala Arg Phe Arg Gln Ile Lys Ile Trp Phe Gln Asn Arg Arg Met Lys
 65                  70                  75                  80

Trp Lys Lys Gly Gly Ala Arg Phe Arg Gln Ile Lys Ile Trp Phe Gln
                 85                  90                  95

Asn Arg Arg Met Lys Trp Lys Lys Gly Gly Ala Arg Val Cys
            100                 105                 110

<210> SEQ ID NO 42
<211> LENGTH: 110
<212> TYPE: PRT
<213> ORGANISM: Artificial
<220> FEATURE:
<223> OTHER INFORMATION: Synthetic MPH + penetratin + MPH
      (heterohexamer)

<400> SEQUENCE: 42

Tyr Arg Phe Tyr Ala Arg Val Arg Arg Gly Pro Arg Arg Gly Gly
 1               5                  10                  15

Ala Arg Phe Tyr Ala Arg Val Arg Arg Gly Pro Arg Arg Gly Gly
                20                  25                  30

Ala Arg Phe Arg Gln Ile Lys Ile Trp Phe Gln Asn Arg Arg Met Lys
                35                  40                  45

Trp Lys Lys Gly Gly Ala Arg Phe Arg Gln Ile Lys Ile Trp Phe Gln
 50                  55                  60

Asn Arg Arg Met Lys Trp Lys Lys Gly Gly Ala Arg Phe Tyr Ala Arg
 65                  70                  75                  80

Val Arg Arg Gly Pro Arg Arg Gly Gly Ala Arg Phe Tyr Ala Arg
                 85                  90                  95

Val Arg Arg Gly Pro Arg Arg Gly Gly Ala Arg Val Cys
            100                 105                 110

<210> SEQ ID NO 43
<211> LENGTH: 88
<212> TYPE: PRT
<213> ORGANISM: Artificial
<220> FEATURE:
<223> OTHER INFORMATION: Synthetic MPH - Ub

<400> SEQUENCE: 43

Tyr Ala Arg Val Arg Arg Gly Pro Arg Arg Gly Gly Gln Ile Phe
 1               5                  10                  15

Val Lys Thr Leu Thr Gly Lys Thr Ile Thr Leu Glu Val Glu Ser Ser
                20                  25                  30

Asp Thr Ile Asp Asn Val Lys Ser Lys Ile Gln Asp Lys Glu Gly Ile
                35                  40                  45

Pro Pro Asp Gln Gln Arg Leu Ile Phe Ala Gly Lys Gln Leu Glu Asp
     50                  55                  60

Gly Arg Thr Leu Ser Asp Tyr Asn Ile Gln Lys Glu Ser Thr Leu His
 65                  70                  75                  80

Leu Val Leu Arg Leu Arg Gly Gly
                 85

<210> SEQ ID NO 44
<211> LENGTH: 104
<212> TYPE: PRT
<213> ORGANISM: Artificial
<220> FEATURE:
<223> OTHER INFORMATION: Synthetic MPH(2) dimer a - Ub

<400> SEQUENCE: 44

Tyr Ala Arg Val Arg Arg Gly Pro Arg Arg Gly Gly Ala Arg Phe
```

```
                      1               5                  10                 15
Tyr Ala Arg Val Arg Arg Gly Pro Arg Gly Gly Gln Ile Phe
                      20                 25                 30

Val Lys Thr Leu Thr Gly Lys Thr Ile Thr Leu Glu Val Glu Ser Ser
            35                 40                 45

Asp Thr Ile Asp Asn Val Lys Ser Lys Ile Gln Asp Lys Glu Gly Ile
            50                 55                 60

Pro Pro Asp Gln Gln Arg Leu Ile Phe Ala Gly Lys Gln Leu Glu Asp
65                  70                 75                 80

Gly Arg Thr Leu Ser Asp Tyr Asn Ile Gln Lys Glu Ser Thr Leu His
                    85                 90                 95

Leu Val Leu Arg Leu Arg Gly Gly
                100
```

```
<210> SEQ ID NO 45
<211> LENGTH: 105
<212> TYPE: PRT
<213> ORGANISM: Artificial
<220> FEATURE:
<223> OTHER INFORMATION: Synthetic MPH(2) dimer b - Ub

<400> SEQUENCE: 45

Tyr Ala Arg Val Arg Arg Gly Pro Arg Gly Gly Gln Ile Phe
1                   5                  10                 15

Val Lys Thr Leu Thr Gly Lys Thr Ile Thr Leu Glu Val Glu Ser Ser
                    20                 25                 30

Asp Thr Ile Asp Asn Val Lys Ser Lys Ile Gln Asp Lys Glu Gly Ile
            35                 40                 45

Pro Pro Asp Gln Gln Arg Leu Ile Phe Ala Gly Lys Gln Leu Glu Asp
        50                 55                 60

Gly Arg Thr Leu Ser Asp Tyr Asn Ile Gln Lys Glu Ser Thr Leu His
65                  70                 75                 80

Leu Val Leu Arg Leu Arg Gly Val Tyr Ala Arg Val Arg Arg Gly
                    85                 90                 95

Pro Arg Gly Gly Ala Arg Val Cys
                100                105
```

```
<210> SEQ ID NO 46
<211> LENGTH: 136
<212> TYPE: PRT
<213> ORGANISM: Artificial
<220> FEATURE:
<223> OTHER INFORMATION: Synthetic MPH(4) tetramer - Ub

<400> SEQUENCE: 46

Tyr Ala Arg Val Arg Arg Gly Pro Arg Gly Gly Ala Arg Phe
1                   5                  10                 15

Tyr Ala Arg Val Arg Arg Gly Pro Arg Gly Gly Ala Arg Phe
                    20                 25                 30

Tyr Ala Arg Val Arg Arg Gly Pro Arg Gly Gly Ala Arg Phe
            35                 40                 45

Tyr Ala Arg Val Arg Arg Gly Pro Arg Gly Gly Gln Ile Phe
        50                 55                 60

Val Lys Thr Leu Thr Gly Lys Thr Ile Thr Leu Glu Val Glu Ser Ser
65                  70                 75                 80

Asp Thr Ile Asp Asn Val Lys Ser Lys Ile Gln Asp Lys Glu Gly Ile
                    85                 90                 95

Pro Pro Asp Gln Gln Arg Leu Ile Phe Ala Gly Lys Gln Leu Glu Asp
```

```
                   100                 105                 110
Gly Arg Thr Leu Ser Asp Tyr Asn Ile Gln Lys Glu Ser Thr Leu His
        115                 120                 125

Leu Val Leu Arg Leu Arg Gly Gly
    130             135

<210> SEQ ID NO 47
<211> LENGTH: 88
<212> TYPE: PRT
<213> ORGANISM: Artificial
<220> FEATURE:
<223> OTHER INFORMATION: Synthetic TAT - Ub

<400> SEQUENCE: 47

Tyr Gly Arg Lys Lys Arg Arg Gln Arg Arg Gly Gly Gln Ile Phe
1               5                   10                  15

Val Lys Thr Leu Thr Gly Lys Thr Ile Thr Leu Glu Val Glu Ser Ser
            20                  25                  30

Asp Thr Ile Asp Asn Val Lys Ser Lys Ile Gln Asp Lys Glu Gly Ile
        35                  40                  45

Pro Pro Asp Gln Gln Arg Leu Ile Phe Ala Gly Lys Gln Leu Glu Asp
    50                  55                  60

Gly Arg Thr Leu Ser Asp Tyr Asn Ile Gln Lys Glu Ser Thr Leu His
65                  70                  75                  80

Leu Val Leu Arg Leu Arg Gly Gly
                85

<210> SEQ ID NO 48
<211> LENGTH: 104
<212> TYPE: PRT
<213> ORGANISM: Artificial
<220> FEATURE:
<223> OTHER INFORMATION: Synthetic TAT(2) dimer a - Ub

<400> SEQUENCE: 48

Tyr Gly Arg Lys Lys Arg Arg Gln Arg Arg Gly Gly Ala Arg Phe
1               5                   10                  15

Tyr Gly Arg Lys Lys Arg Arg Gln Arg Arg Gly Gly Gln Ile Phe
            20                  25                  30

Val Lys Thr Leu Thr Gly Lys Thr Ile Thr Leu Glu Val Glu Ser Ser
        35                  40                  45

Asp Thr Ile Asp Asn Val Lys Ser Lys Ile Gln Asp Lys Glu Gly Ile
    50                  55                  60

Pro Pro Asp Gln Gln Arg Leu Ile Phe Ala Gly Lys Gln Leu Glu Asp
65                  70                  75                  80

Gly Arg Thr Leu Ser Asp Tyr Asn Ile Gln Lys Glu Ser Thr Leu His
                85                  90                  95

Leu Val Leu Arg Leu Arg Gly Gly
            100

<210> SEQ ID NO 49
<211> LENGTH: 99
<212> TYPE: PRT
<213> ORGANISM: Artificial
<220> FEATURE:
<223> OTHER INFORMATION: Synthetic TAT(2) dimer b -Ub

<400> SEQUENCE: 49

Tyr Gly Arg Lys Lys Arg Arg Gln Arg Arg Gly Gly Gln Ile Phe
1               5                   10                  15
```

```
Val Lys Thr Leu Thr Gly Lys Thr Ile Thr Leu Glu Val Glu Ser Ser
         20                  25                  30

Asp Thr Ile Asp Asn Val Lys Ser Lys Ile Gln Asp Lys Glu Gly Ile
             35                  40                  45

Pro Pro Asp Gln Gln Arg Leu Ile Phe Ala Gly Lys Gln Leu Glu Asp
         50                  55                  60

Gly Arg Thr Leu Ser Asp Tyr Asn Ile Gln Lys Glu Ser Thr Leu His
 65                  70                  75                  80

Leu Val Leu Arg Leu Arg Gly Val Tyr Gly Arg Lys Arg Arg Gln
                 85                  90                  95

Arg Arg Arg

<210> SEQ ID NO 50
<211> LENGTH: 136
<212> TYPE: PRT
<213> ORGANISM: Artificial
<220> FEATURE:
<223> OTHER INFORMATION: Synthetic TAT(4) tetramer - Ub

<400> SEQUENCE: 50

Tyr Gly Arg Lys Lys Arg Arg Gln Arg Arg Gly Gly Ala Arg Phe
 1               5                  10                  15

Tyr Gly Arg Lys Lys Arg Arg Gln Arg Arg Gly Gly Ala Arg Phe
                 20                  25                  30

Tyr Gly Arg Lys Lys Arg Arg Gln Arg Arg Gly Gly Ala Arg Phe
             35                  40                  45

Tyr Gly Arg Lys Lys Arg Arg Gln Arg Arg Gly Gly Gln Ile Phe
         50                  55                  60

Val Lys Thr Leu Thr Gly Lys Thr Ile Thr Leu Glu Val Glu Ser Ser
 65                  70                  75                  80

Asp Thr Ile Asp Asn Val Lys Ser Lys Ile Gln Asp Lys Glu Gly Ile
                 85                  90                  95

Pro Pro Asp Gln Gln Arg Leu Ile Phe Ala Gly Lys Gln Leu Glu Asp
             100                 105                 110

Gly Arg Thr Leu Ser Asp Tyr Asn Ile Gln Lys Glu Ser Thr Leu His
         115                 120                 125

Leu Val Leu Arg Leu Arg Gly Gly
         130                 135

<210> SEQ ID NO 51
<211> LENGTH: 93
<212> TYPE: PRT
<213> ORGANISM: Artificial
<220> FEATURE:
<223> OTHER INFORMATION: Synthetic penetratin - Ub

<400> SEQUENCE: 51

Arg Gln Ile Lys Ile Trp Phe Gln Asn Arg Arg Met Lys Trp Lys Lys
 1               5                  10                  15

Gly Gly Gln Ile Phe Val Lys Thr Leu Thr Gly Lys Thr Ile Thr Leu
                 20                  25                  30

Glu Val Glu Ser Ser Asp Thr Ile Asp Asn Val Lys Ser Lys Ile Gln
             35                  40                  45

Asp Lys Glu Gly Ile Pro Pro Asp Gln Gln Arg Leu Ile Phe Ala Gly
         50                  55                  60

Lys Gln Leu Glu Asp Gly Arg Thr Leu Ser Asp Tyr Asn Ile Gln Lys
 65                  70                  75                  80

Glu Ser Thr Leu His Leu Val Leu Arg Leu Arg Gly Gly
```

<210> SEQ ID NO 52
<211> LENGTH: 109
<212> TYPE: PRT
<213> ORGANISM: Artificial
<220> FEATURE:
<223> OTHER INFORMATION: Synthetic penetratin(2) dimer - Ub

<400> SEQUENCE: 52

Arg Gln Ile Lys Ile Trp Phe Gln Asn Arg Arg Met Lys Trp Lys Lys
1               5                   10                  15
Gly Gly Gln Ile Phe Val Lys Thr Leu Thr Gly Lys Thr Ile Thr Leu
            20                  25                  30
Glu Val Glu Ser Ser Asp Thr Ile Asp Asn Val Lys Ser Lys Ile Gln
        35                  40                  45
Asp Lys Glu Gly Ile Pro Pro Asp Gln Gln Arg Leu Ile Phe Ala Gly
    50                  55                  60
Lys Gln Leu Glu Asp Gly Arg Thr Leu Ser Asp Tyr Asn Ile Gln Lys
65                  70                  75                  80
Glu Ser Thr Leu His Leu Val Leu Arg Leu Arg Gly Val Arg Gln Ile
                85                  90                  95
Lys Ile Trp Phe Gln Asn Arg Arg Met Lys Trp Lys Lys
            100                 105

<210> SEQ ID NO 53
<211> LENGTH: 119
<212> TYPE: PRT
<213> ORGANISM: Artificial
<220> FEATURE:
<223> OTHER INFORMATION: Synthetic Pep-1(2) dimer - Ub

<400> SEQUENCE: 53

Lys Glu Thr Trp Trp Glu Thr Trp Trp Thr Glu Trp Ser Gln Pro Lys
1               5                   10                  15
Lys Lys Arg Lys Val Gly Gly Gln Ile Phe Val Lys Thr Leu Thr Gly
            20                  25                  30
Lys Thr Ile Thr Leu Glu Val Glu Ser Ser Asp Thr Ile Asp Asn Val
        35                  40                  45
Lys Ser Lys Ile Gln Asp Lys Glu Gly Ile Pro Pro Asp Gln Gln Arg
    50                  55                  60
Leu Ile Phe Ala Gly Lys Gln Leu Glu Asp Gly Arg Thr Leu Ser Asp
65                  70                  75                  80
Tyr Asn Ile Gln Lys Glu Ser Thr Leu His Leu Val Leu Arg Leu Arg
                85                  90                  95
Gly Val Lys Glu Thr Trp Trp Glu Thr Trp Trp Thr Glu Trp Ser Gln
            100                 105                 110
Pro Lys Lys Lys Arg Lys Val
        115

<210> SEQ ID NO 54
<211> LENGTH: 99
<212> TYPE: PRT
<213> ORGANISM: Artificial
<220> FEATURE:
<223> OTHER INFORMATION: Synthetic MPH + TAT - Ub

<400> SEQUENCE: 54

Tyr Ala Arg Val Arg Arg Gly Pro Arg Arg Gly Gly Gln Ile Phe
1               5                   10                  15

-continued

Val Lys Thr Leu Thr Gly Lys Thr Ile Thr Leu Glu Val Glu Ser Ser
            20                  25                  30

Asp Thr Ile Asp Asn Val Lys Ser Lys Ile Gln Asp Lys Glu Gly Ile
            35                  40                  45

Pro Pro Asp Gln Gln Arg Leu Ile Phe Ala Gly Lys Gln Leu Glu Asp
50                      55                  60

Gly Arg Thr Leu Ser Asp Tyr Asn Ile Gln Lys Glu Ser Thr Leu His
65                  70                  75                  80

Leu Val Leu Arg Leu Arg Gly Val Tyr Gly Arg Lys Arg Arg Gln
                85                  90                  95

Arg Arg Arg

<210> SEQ ID NO 55
<211> LENGTH: 98
<212> TYPE: PRT
<213> ORGANISM: Artificial
<220> FEATURE:
<223> OTHER INFORMATION: Synthetic Sim-2 + MPH - Ub

<400> SEQUENCE: 55

Ala Lys Ala Ala Arg Gln Ala Ala Arg Gly Gly Gly Gln Ile Phe Val
1               5                   10                  15

Lys Thr Leu Thr Gly Lys Thr Ile Thr Leu Glu Val Glu Ser Ser Asp
            20                  25                  30

Thr Ile Asp Asn Val Lys Ser Lys Ile Gln Asp Lys Glu Gly Ile Pro
            35                  40                  45

Pro Asp Gln Gln Arg Leu Ile Phe Ala Gly Lys Gln Leu Glu Asp Gly
50                  55                      60

Arg Thr Leu Ser Asp Tyr Asn Ile Gln Lys Glu Ser Thr Leu His Leu
65                  70                  75                  80

Val Leu Arg Leu Arg Gly Val Tyr Ala Arg Val Arg Arg Gly Pro
                85                  90                  95

Arg Arg

<210> SEQ ID NO 56
<211> LENGTH: 104
<212> TYPE: PRT
<213> ORGANISM: Artificial
<220> FEATURE:
<223> OTHER INFORMATION: Synthetic penetratin + MPH - Ub

<400> SEQUENCE: 56

Arg Gln Ile Lys Ile Trp Phe Gln Asn Arg Arg Met Lys Trp Lys Lys
1               5                   10                  15

Gly Gly Gln Ile Phe Val Lys Thr Leu Thr Gly Lys Thr Ile Thr Leu
            20                  25                  30

Glu Val Glu Ser Ser Asp Thr Ile Asp Asn Val Lys Ser Lys Ile Gln
            35                  40                  45

Asp Lys Glu Gly Ile Pro Pro Asp Gln Gln Arg Leu Ile Phe Ala Gly
            50                  55                  60

Lys Gln Leu Glu Asp Gly Arg Thr Leu Ser Asp Tyr Asn Ile Gln Lys
65                  70                  75                  80

Glu Ser Thr Leu His Leu Val Leu Arg Leu Arg Gly Val Tyr Ala Arg
                85                  90                  95

Val Arg Arg Arg Gly Pro Arg Arg
            100

<210> SEQ ID NO 57

```
<211> LENGTH: 129
<212> TYPE: PRT
<213> ORGANISM: Artificial
<220> FEATURE:
<223> OTHER INFORMATION: Synthetic penetratin + MPH(2) dimer - Ub

<400> SEQUENCE: 57

Arg Gln Ile Lys Ile Trp Phe Gln Asn Arg Arg Met Lys Trp Lys Lys
1               5                   10                  15

Gly Gly Gln Ile Phe Val Lys Thr Leu Thr Gly Lys Thr Ile Thr Leu
            20                  25                  30

Glu Val Glu Ser Ser Asp Thr Ile Asp Asn Val Lys Ser Lys Ile Gln
        35                  40                  45

Asp Lys Glu Gly Ile Pro Pro Asp Gln Gln Arg Leu Ile Phe Ala Gly
    50                  55                  60

Lys Gln Leu Glu Asp Gly Arg Thr Leu Ser Asp Tyr Asn Ile Gln Lys
65                  70                  75                  80

Glu Ser Thr Leu His Leu Val Leu Arg Leu Arg Gly Val Ser Arg Val
                85                  90                  95

Tyr Ala Arg Val Arg Arg Arg Gly Pro Arg Arg Gly Gly Ala Arg Phe
            100                 105                 110

Tyr Ala Arg Val Arg Arg Arg Gly Pro Arg Arg Gly Gly Ala Arg Val
        115                 120                 125

Cys

<210> SEQ ID NO 58
<211> LENGTH: 161
<212> TYPE: PRT
<213> ORGANISM: Artificial
<220> FEATURE:
<223> OTHER INFORMATION: Synthetic penetratin + MPH(4) tetramer - Ub

<400> SEQUENCE: 58

Arg Gln Ile Lys Ile Trp Phe Gln Asn Arg Arg Met Lys Trp Lys Lys
1               5                   10                  15

Gly Gly Gln Ile Phe Val Lys Thr Leu Thr Gly Lys Thr Ile Thr Leu
            20                  25                  30

Glu Val Glu Ser Ser Asp Thr Ile Asp Asn Val Lys Ser Lys Ile Gln
        35                  40                  45

Asp Lys Glu Gly Ile Pro Pro Asp Gln Gln Arg Leu Ile Phe Ala Gly
    50                  55                  60

Lys Gln Leu Glu Asp Gly Arg Thr Leu Ser Asp Tyr Asn Ile Gln Lys
65                  70                  75                  80

Glu Ser Thr Leu His Leu Val Leu Arg Leu Arg Gly Val Ser Arg Val
                85                  90                  95

Tyr Ala Arg Val Arg Arg Arg Gly Pro Arg Arg Gly Gly Ala Arg Phe
            100                 105                 110

Tyr Ala Arg Val Arg Arg Arg Gly Pro Arg Arg Gly Gly Ala Arg Phe
        115                 120                 125

Tyr Ala Arg Val Arg Arg Arg Gly Pro Arg Arg Gly Gly Ala Arg Phe
    130                 135                 140

Tyr Ala Arg Val Arg Arg Arg Gly Pro Arg Arg Gly Gly Ala Arg Val
145                 150                 155                 160

Cys

<210> SEQ ID NO 59
<211> LENGTH: 123
<212> TYPE: PRT
```

<213> ORGANISM: Artificial
<220> FEATURE:
<223> OTHER INFORMATION: Synthetic Sim-2-UB(v)-Hph-1(2)

<400> SEQUENCE: 59

Ala Lys Ala Ala Arg Gln Ala Ala Arg Gly Gly Gly Gln Ile Phe Val
1               5                   10                  15

Lys Thr Leu Thr Gly Lys Thr Ile Thr Leu Glu Val Glu Ser Ser Asp
                20                  25                  30

Thr Ile Asp Asn Val Lys Ser Lys Ile Gln Asp Lys Glu Gly Ile Pro
            35                  40                  45

Pro Asp Gln Gln Arg Leu Ile Phe Ala Gly Lys Gln Leu Glu Asp Gly
    50                  55                  60

Arg Thr Leu Ser Asp Tyr Asn Ile Gln Lys Glu Ser Thr Leu His Leu
65                  70                  75                  80

Val Leu Arg Leu Arg Gly Val Ser Arg Val Tyr Ala Arg Val Arg Arg
                85                  90                  95

Arg Gly Pro Arg Arg Gly Gly Ala Arg Phe Tyr Ala Arg Val Arg Arg
                100                 105                 110

Arg Gly Pro Arg Arg Gly Gly Ala Arg Val Cys
                115                 120

<210> SEQ ID NO 60
<211> LENGTH: 155
<212> TYPE: PRT
<213> ORGANISM: Artificial
<220> FEATURE:
<223> OTHER INFORMATION: Synthetic Sim-2-UB(v)-Hph-1(4)

<400> SEQUENCE: 60

Ala Lys Ala Ala Arg Gln Ala Ala Arg Gly Gly Gly Gln Ile Phe Val
1               5                   10                  15

Lys Thr Leu Thr Gly Lys Thr Ile Thr Leu Glu Val Glu Ser Ser Asp
                20                  25                  30

Thr Ile Asp Asn Val Lys Ser Lys Ile Gln Asp Lys Glu Gly Ile Pro
            35                  40                  45

Pro Asp Gln Gln Arg Leu Ile Phe Ala Gly Lys Gln Leu Glu Asp Gly
    50                  55                  60

Arg Thr Leu Ser Asp Tyr Asn Ile Gln Lys Glu Ser Thr Leu His Leu
65                  70                  75                  80

Val Leu Arg Leu Arg Gly Val Ser Arg Val Tyr Ala Arg Val Arg Arg
                85                  90                  95

Arg Gly Pro Arg Arg Gly Gly Ala Arg Phe Tyr Ala Arg Val Arg Arg
                100                 105                 110

Arg Gly Pro Arg Arg Gly Gly Ala Arg Phe Tyr Ala Arg Val Arg Arg
                115                 120                 125

Arg Gly Pro Arg Arg Gly Gly Ala Arg Phe Tyr Ala Arg Val Arg Arg
                130                 135                 140

Arg Gly Pro Arg Arg Gly Gly Ala Arg Val Cys
145                 150                 155

PHARMACEUTICAL COMPOSITIONS AND METHODS FOR DELIVERING NUCLEIC ACIDS INTO CELLS

CROSS-REFERENCE TO RELATED APPLICATION

This application claims the benefit of the filing date of U.S. Provisional Patent Application No. 60/990,124, filed Nov. 26, 2007, which is incorporated herein by reference in its entirety.

REFERENCE TO SEQUENCE LISTING SUBMITTED ELECTRONICALLY

The content of the sequence listing text file (File name: Sequence Listing ascii.txt; Size: 41,674 bytes; and Date of Creation: Nov. 19, 2008) filed herewith the application is incorporated herein by reference in its entirety.

BACKGROUND OF THE INVENTION

1. Field of the Invention

The present invention relates to methods of delivering nucleic acids into cells in vivo or in vitro using a nucleic acid binding molecule containing a multimeric and/or spacer-incorporated protein transduction domain (PTD). The invention also relates to novel compositions that contain a nucleic acid complexed or conjugated with a nucleic acid binding molecule. The invention further relates to a method of inhibiting expression of a target gene, as well as determining the function of a target gene.

2. Background Art

RNA interference (RNAi) refers to a process in which short RNA fragments interfere with messenger RNA (mRNA), an important mediator of gene expression, by inducing the degradation of mRNA, to block the synthesis of proteins as mRNA products. When the short RNA fragments base pair with an mRNA, a double-stranded RNA is formed that is degraded in cells. The selective effect of RNAi on gene expression makes it a valuable research tool when investigating the function of a specific gene. Also, RNAi has been frequently used in the development of new drugs which specifically suppress the expression of target genes.

Dependent on origin, short RNA fragments are classified as small interfering RNA (siRNA) when they are derived from exogenous sources (Elbashir, S. M., et al., *Nature* 411: 494-498 (2001)), and microRNA (miRNA) when they are produced from RNA-coding genes in the cell's own genome.

The use of siRNA can be largely divided into two categories: (1) siRNA or short hairpin RNA (shRNA), produced in vitro by chemical synthesis or biological synthesis, is delivered directly into cells; and (2) various DNA vectors capable of expressing siRNA are injected into cells, whereby the cells produce siRNA (see, e.g., U.S. Pat. No. 6,278,039; U.S. Application No. 2002/0006664; WO 99/32619; WO 01/29058; WO 01/68836; and WO 01/96584). Various application techniques based on these two categories can be used such that their advantages are effectively utilized. For the latter one, recent attempts have also been made to deliver DNA vectors, which can make siRNA, to down-regulate genes which are turned on in diseases such as cancer (Meyer, M. and Wagner, E., *Hum. Gene Ther.* 17(11):1062-1076 (2006)).

In RNAi, the efficiency of delivering nucleic acids into cells in vivo or in vitro determines the efficiency of RNAi. However, the efficiency of delivering siRNA or DNA vectors for siRNA into cells remains a major impediment for the practical application of the two techniques. This is because nucleic acids such as RNA or DNA are too large to permeate the cell membrane. In experiments, these nucleic acids can be introduced into cells without the need for physical or chemical means, even though the mechanism thereof is not clearly found. However, the delivery of nucleic acids is difficult to apply in practice because it has excessively low efficiency.

One method, which is most frequently used in in vitro experiments in laboratories, is to use liposome to aid delivery of nucleic acids. In the 1980s, cationic liposome was developed, which has greatly improved transfection efficiency compared to neutral liposome. However, this efficiency is high in in vitro experiments and is greatly decreased in vivo due to blood or body fluids. Also, liposome itself has strong toxicity, which makes it difficult to apply liposome in large amounts, thus limiting the application thereof in the human body.

Another method for delivering nucleic acids into cells uses viral vectors. The viral vector can be used as an effective carrier, but was found to have serious side-effects, such as cell carcinogenesis, in addition to the ethical problem of introducing foreign genes into human cells, and thus extensive clinic studies are strongly required to ensure safety. For this reason, in current circumstances, the in vivo introduction of viral vectors cannot be reliably used clinically or in industry despite many studies.

Other methods of physically delivering naked nucleic acids (i.e., nucleic acids without any other components to aid their delivery) directly in vivo, for example, by electroporation and hydrodynamic injection, have also been studied. The results of recent studies showed that the delivery of naked RNA into veins, abdominal cavities or eyeballs can knock down the expression of specific genes (Herweijer, H. and Wolff, J. A., *Gene Ther.* 10(6):453-458 (2003); Hagstrom, J. E. et al., *Mol. Ther.* 10(2):386-398 (2004)). However, the characteristics of these methods limit their practical applications.

In addition, studies focused on the use of nanoparticles including polyethylenimine (PEI) or the like, as delivery vectors, have been actively conducted.

Other than low efficiency in delivery, another impediment to using siRNA in practice is that it has a short in vivo half-life, which requires the use of increasing amounts thereof. Attempts have been made to modify the phosphate backbone of RNA into phosphorothioate or the like such that it has resistance to RNAse. Moreover, studies focused on increasing the half-life of RNA by modifying RNA with polyethyleneglycol (PEG), cholesterol or the like have also been conducted. However, despite such various attempts and studies, low nucleic acid delivery efficiency remains a major problem in the practical use of RNAi.

Recently, the use of a protein transduction domain (PTD) has been proposed. PTDs are low molecular-weight peptides that are useful for the delivery of biologically active molecules into cells (Viehl C. T., et al., *Ann. Surg. Oncol.* 12:517-525 (2005); Noguchi H., et al., *Nat. Med.* 10:305-309 (2004); and Fu A. L., et al., *Neurosci. Lett.* 368:258-62 (2004)). Various PTDs are known, but in most cases, the number of positively charged amino acids in a PTD is very high. The most commonly known PTD is Tat of HIV, and in addition, there are Antp, VP22, synthetic polyarginine and the like. Recently, MPH-1, Sim-2 and the like were discovered.

PTDs are known to perform the efficient delivery of molecules in vitro or in vivo regardless of the kind thereof or the cell type. Most PTDs can form a stable non-covalent bond with nucleic acids and deliver the nucleic acids into cells. The third helix of Antennapedia homeodomain has been shown to form stable non-covalent complexes with small oligonucleotides and to facilitate their internalization (Dom, G., et al., *Nucleic Acids Res.* 31:556-561 (2003)). Pep-3 has been reported to form stable complexes with peptide nucleic acid through non-covalent interactions, and promote their delivery into cells (Morris, M. C., et al., *Nucleic Acids Res.* 35 (2007)). MPG peptide, which contains a hydrophobic domain derived from the fusion sequence of HIV gp41 and a hydrophilic domain derived from the nuclear localization sequence of SV40 T-antigen, has been demonstrated to form non-covalent bond with antisense oligonucleotides to deliver the oligonucleotides into cultured mammalian cells (Morris, M. C. et al., *Nucleic Acids Res.* 25:2730-2736 (1997)). A dimer, trimer and tetramer of Tat peptide have been reported to form stable particles with plasmid DNA through non-covalent interactions, and promote their delivery into cells (Rudolph, C., et al., *J. Biol. Chem.* 278:11411-11418 (2003)).

PTDs can also form a stable covalent bond with nucleic acids to promote their delivery. Tat peptide covalently attached to liposomes promotes rapid delivery of DNA (Torchilin, V. P., et al., *Proc. Natl. Acad. Sci. USA* 98:8786-8791 (2001), and Torchilin, V. P., et al., *Proc. Natl. Acad. Sci. USA* 100:1972-1977 (2003)). The use of penetratin and transportan to deliver peptide nucleic acid molecules across plasma membranes, through a labile bond, such as a disulfide bond, has also been described (see U.S. Pat. No. 6,025,140).

A PTD forming a covalent bond with siRNA has been described. Tat peptide covalently attached to siRNA promotes nuclear delivery of siRNA (Chiu, Y., et al., *Chem. Biol.* 11(8):1165-1175 (2004)). Penetratin and transportan peptide covalently attached to siRNA promote efficient cellular delivery of siRNA (Davidson, T. J., et al., *J. Neurosci.* 24(45): 10040-10046 (2004); Muratovska, A. and Eccles, M. R., *FEBS* 558:63-68 (2004)).

Although high efficiency in delivery is achieved in some studies, the use of PDT in delivery of siRNA or DNA vectors for siRNA does not produce RNAi effects of stable and high efficiency. Also, there are reports that the use of PDT provides insignificant effects. siRNA covalently attached to Tat or penetratin peptide showed no RNAi effects in vivo (Moschos, S. A., et al., poster presentation at the Biochemical Society Focused Meeting, UK, (2007)).

As mentioned above, most PTDs are rich in positively charged amino acids, which can bind to the negatively charged phosphate backbone of nucleic acids. This binding between nucleic acids and PTDs is possible both when PTDs and nucleic acids form a non-covalent bond and when they form a covalent bond. Most studies employed only a single PTD unit. Even weak binding between the PTD and the nucleic acid can influence the structure of PTD which is important to maintain its delivery function. Thus, the delivery efficiency of a PTD can be greatly reduced. A PTD, which does not bind to nucleic acids, maintains the ability to be delivered into cells, but cannot be used to deliver nucleic acids. Also, a PTD that binds to nucleic acids, has a reduced ability to be delivered into cells. As a result, methods of delivering nucleic acids into cells using PTDs in prior studies are not effective or efficient.

Accordingly, the present inventors designed multimeric or spacer-incorporated PTD molecules to deliver nucleic acids into cells, whereby the multimeric or spacer-incorporated PTD molecules maintain the ability to be delivered into cells.

BRIEF SUMMARY OF THE INVENTION

One object of the invention is to effectively perform the delivery of nucleic acids into cells in vivo or in vitro using a nucleic acid binding molecule.

To achieve the above object, the present invention provides a complex or conjugate comprising a nucleic acid complexed or conjugated with a nucleic acid binding molecule containing one or more multimeric or spacer-incorporated PTDs. The spacer-incorporated PTDs may have a length corresponding to molecular weights of between 1-250 kd, 5-180 kd, 5-150 kd or 5-30 kd. The efficiency for delivering nucleic acid into cells will be greatly increased because the binding between the nucleic acid, and the nucleic acid binding molecule does not influence the structure of the PTD, thus maintaining its delivery function.

One other embodiment of the present invention is a single-stranded nucleic acid comprising a phosphate backbone complexed or conjugated to a nucleic acid binding molecule containing one or more multimeric or spacer-incorporated PTDs that comprise one or more PTD molecules.

Another embodiment is a double-stranded RNA complexed or conjugated to a nucleic acid binding molecule containing one or more multimeric or spacer-incorporated PTDs that comprise one or more PTD molecules.

An additional embodiment is a double-stranded nucleic acid complexed or conjugated to a nucleic acid binding molecule containing one or more multimeric or spacer-incorporated PTDs or spacer-incorporated proteins, that comprise one or more PTD molecules.

One embodiment is a double-stranded RNA complexed or conjugated to a nucleic acid binding molecule containing one or more multimeric PTDs that comprise five or more PTD molecules.

The invention also encompasses a composition comprising a single-stranded nucleic acid comprising a phosphate backbone complexed or conjugated to a nucleic acid binding molecule containing one or more multimeric or spacer-incorporated PTDs that comprise one or more PTD molecules.

An additional embodiment is a composition comprising a double-stranded RNA complexed or conjugated to a nucleic acid binding molecule containing one or more multimeric or spacer-incorporated PTDs that comprise one or more PTD molecules.

An additional embodiment is a composition comprising a double-stranded nucleic acid complexed or conjugated to a nucleic acid binding molecule containing one or more multimeric or spacer-incorporated PTDs that comprise one or more PTD molecules.

The invention also encompasses a nucleic acid binding molecule comprising one or more multimeric or spacer-incorporated PTDs that comprise one or more PTD molecules.

The invention also encompasses methods of producing any one of the above nucleic acid molecules complexed or conjugated to one or more nucleic acid binding molecules.

This invention also encompasses methods of facilitating delivery of any one of the above nucleic acid molecules complexed or conjugated to one or more nucleic acid binding molecules.

This invention also encompasses methods of determining the function of a target gene in a cell using a nucleic acid complexed or conjugated to one or more nucleic acid binding molecules.

This invention also encompasses methods of inhibiting expression of a target gene in a cell using a nucleic acid complexed or conjugated to one or more nucleic acid binding molecules.

For all of the above embodiments, a nucleic acid binding molecule can further contain one or more nucleic acid binding regions.

BRIEF DESCRIPTION OF THE DRAWINGS/FIGURES

FIG. 1 shows the relationship between nucleic acids and nucleic acid binding molecules. FIG. 1A shows a nucleic acid binding molecule with a nucleic acid binding region wherein the PTD is not complexed with a nucleic acid. FIG. 1B shows a nucleic acid binding molecule with a nucleic acid binding region, which is a combination of PTD and other substances complexed with a nucleic acid. FIG. 1C shows a nucleic acid binding molecule with a nucleic acid binding region which is PTD complexed with a nucleic acid. FIG. 1D shows a nucleic acid binding molecule with a nucleic acid binding region conjugated with a nucleic acid. FIG. 1E shows a nucleic acid binding molecule with a nucleic acid binding region complexed with a nucleic acid. The nucleic acid binding region comprises a multimeric PTD and a spacer either within or at the end of the multimeric PTD. The spacer has a steric hindrance effect.

FIG. 2 shows the process to prepare the vectors for the expression of recombinant multimeric PTDs. FIG. 2A describes the process to prepare the vectors for the expression of recombinant proteins of Sim-2UB(v)PTD(2), Sim-2UB(v)PTD(4), AntpUB(v)PTD(2) and AntpUB(v)PTD(4). FIG. 2B describes the process to prepare the vectors for the expression of N-terminal ubiquitin fusion proteins of Sim-2UB(v)PTD(2), Sim-2UB(v)PTD(4), AntpUB(v)PTD(2) and AntpUB(v)PTD(4).

FIG. 2C describes the process to prepare the vectors for the expression of N-terminal ubiquitin fusion proteins of PTD(2)UB and PTD(4)UB. PTDs in FIGS. 2A, 2B 2C and 2D represent Hph-1.

FIG. 2D describes the process to prepare the vectors for the expression of a fusion protein of a MPH-1-PTD octamer with ubiquitin.

FIG. 2E describes the process to prepare the vectors for the expression of a fusion protein of a MPH-1-PTD tetramer and hexamer with ubiquitin.

Figure 7:
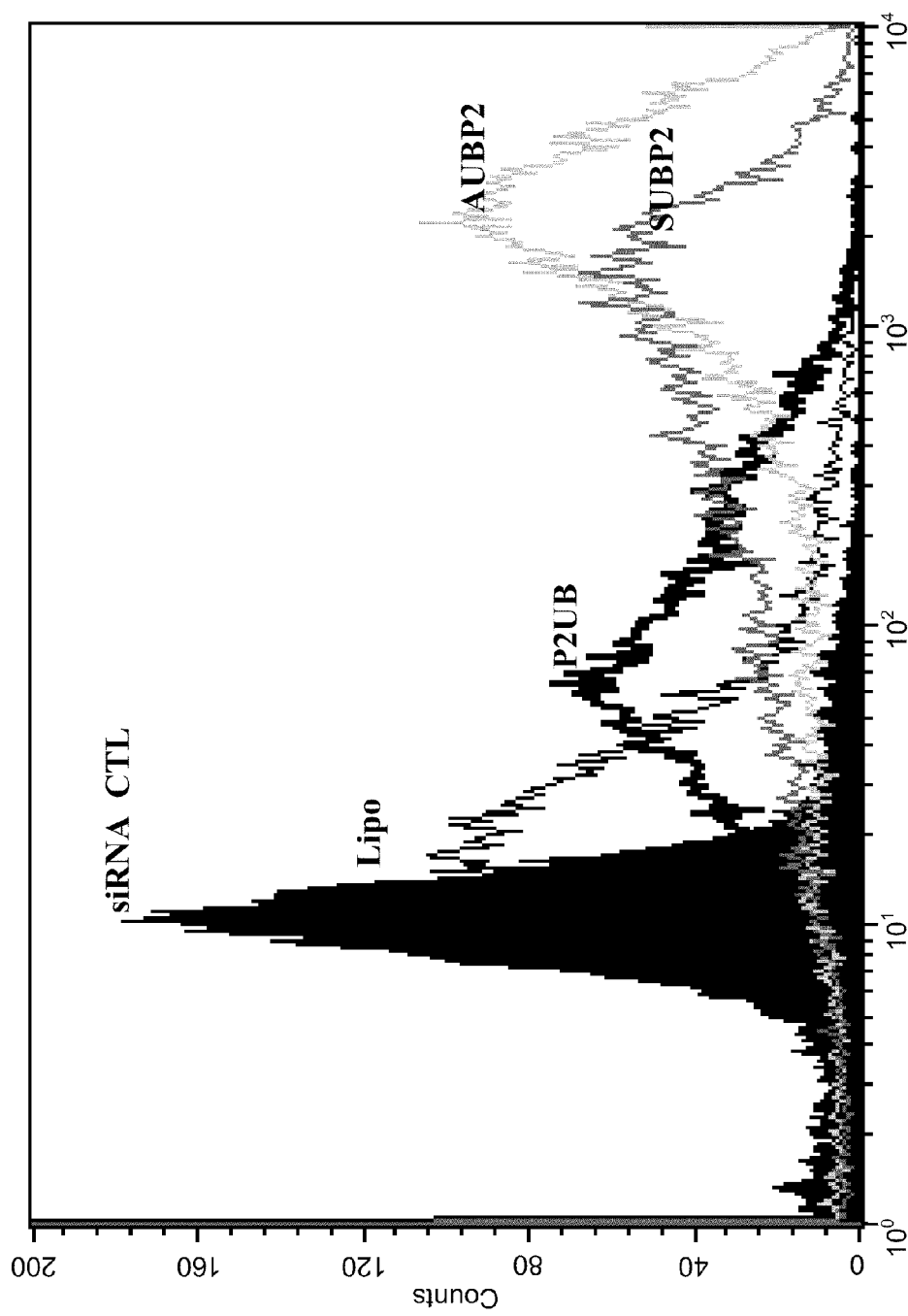

FIG. 7 shows the delivery-efficiency of siRNA by spacer-incorporated proteins. One strand of the siRNA was labeled with carboxyfluorescein (FAM). The siRNA were transduced alone (siRNA CTL), complexed with AUBP2 (AntpUB(v)PTD(2)), SUBP2 (Sim-2UB(v)PTD(2)), P2UB(PTD(2)UB) or liposome (Lipo). The transduced cells were analyzed by FACS.

Figure 8:
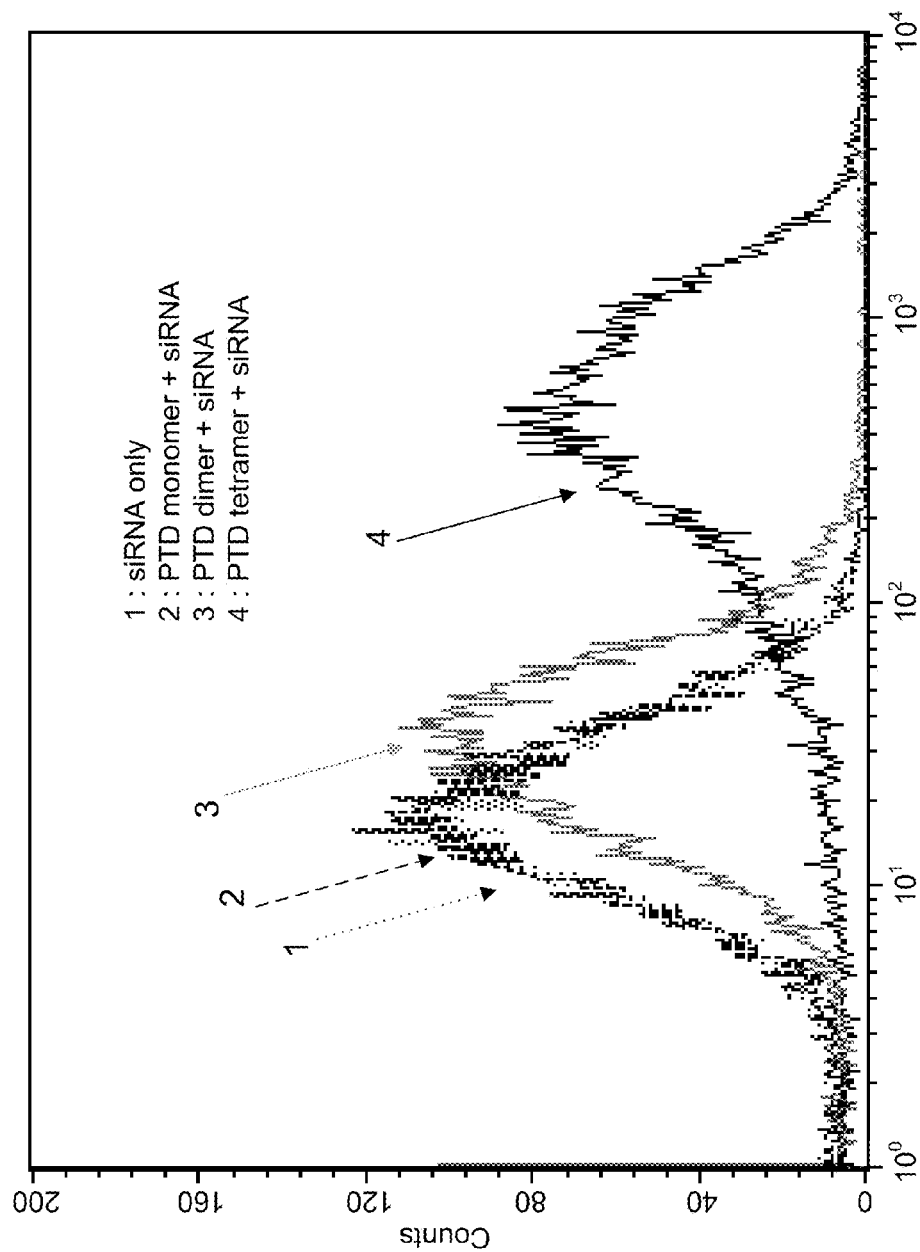

FIG. 8 shows the relationship between siRNA delivery and the number of PTDs in a multimeric PTD. The transduced cells were analyzed by FACS. FIG. 8 shows the height of fluorescence intensity for the 530/30 filter (FL-1H).

Figure 9:
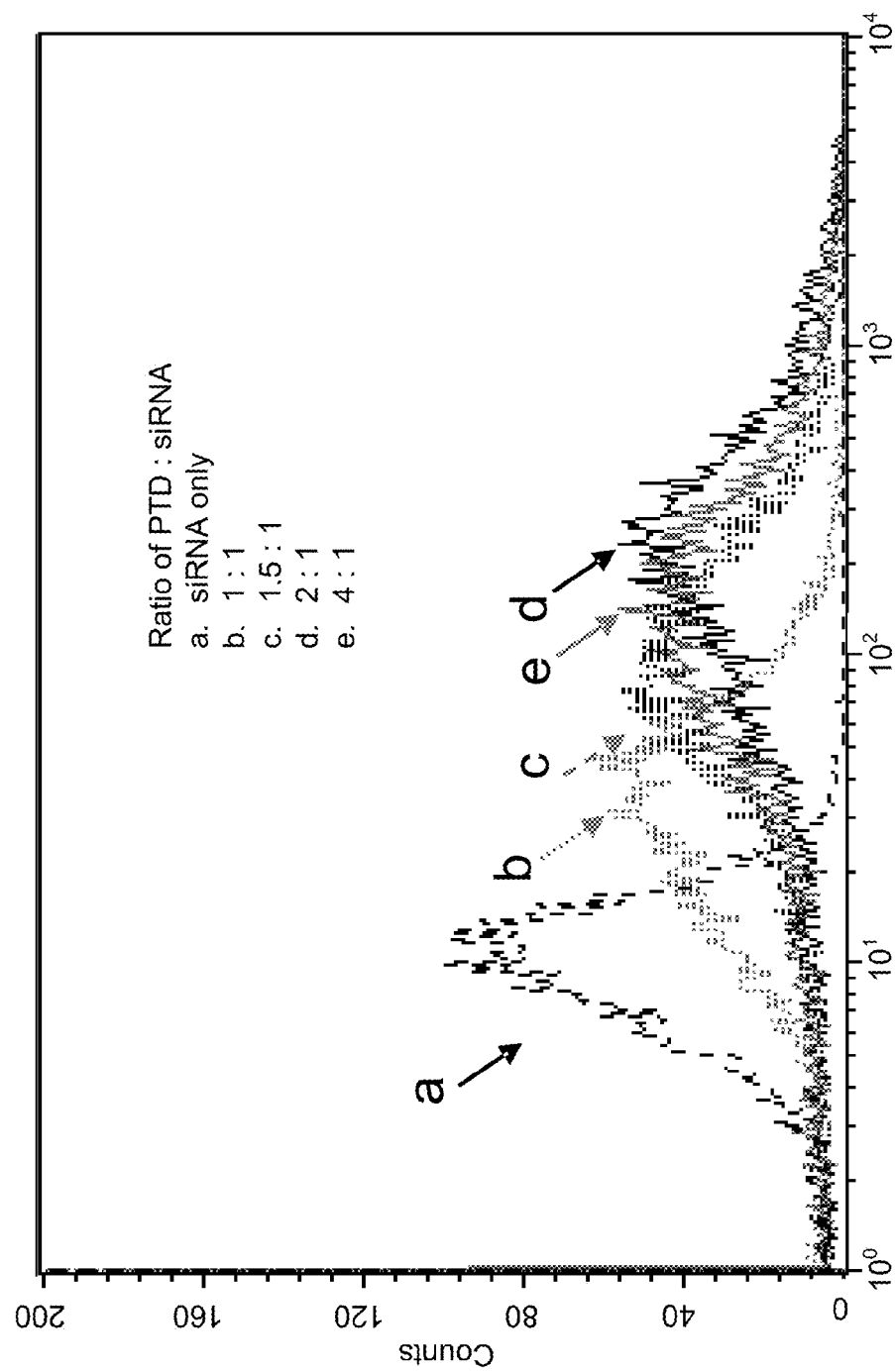

FIG. 9 shows the effect of PTD to siRNA ratio on the relative efficiency of delivery into cells. siRNA was complexed or conjugated with multimeric or spacer-incorporated PTDs. The transduced cells were analyzed by FACS. FIG. 9 shows the height of fluorescence intensity for the 530/30 filter (FL-1H).

Figure 10:
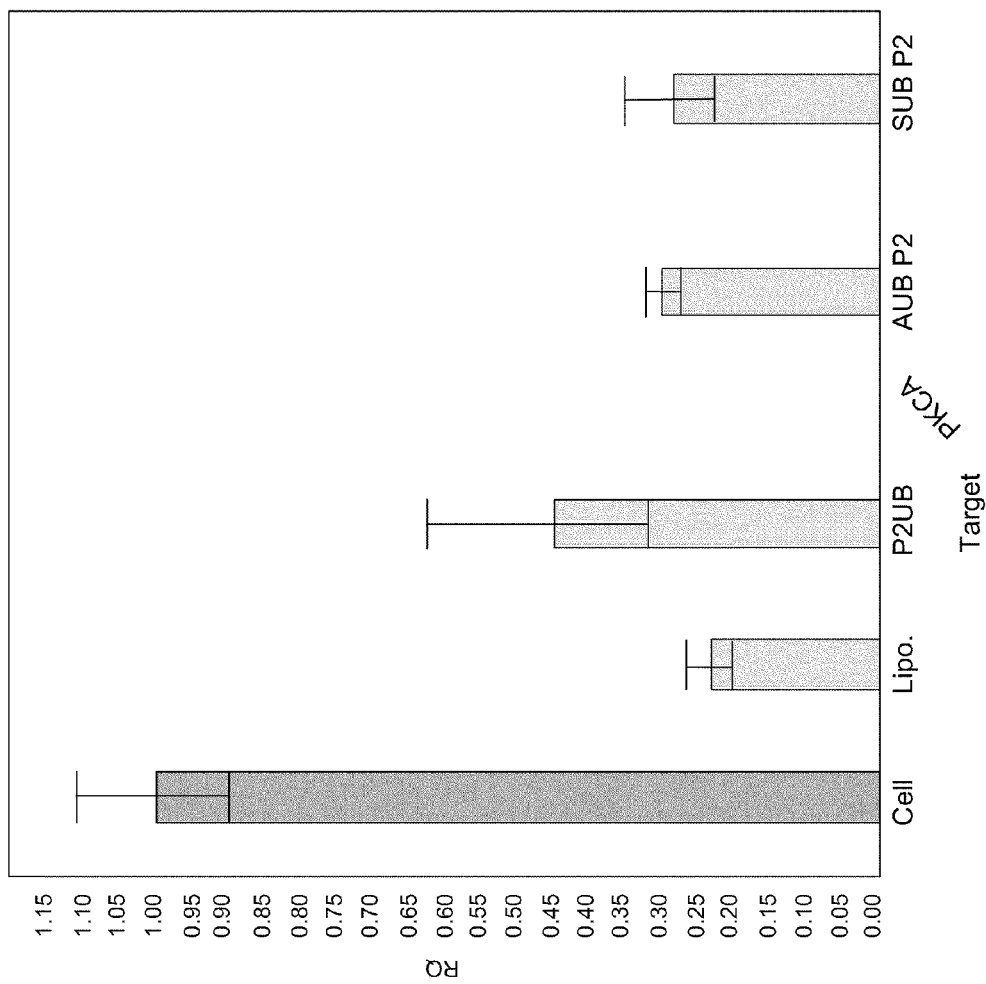

FIG. 10 shows that siRNA delivered with spacer-incorporated proteins retain the ability to inhibit the transcription of the target gene, PKCA.

Figure 11:
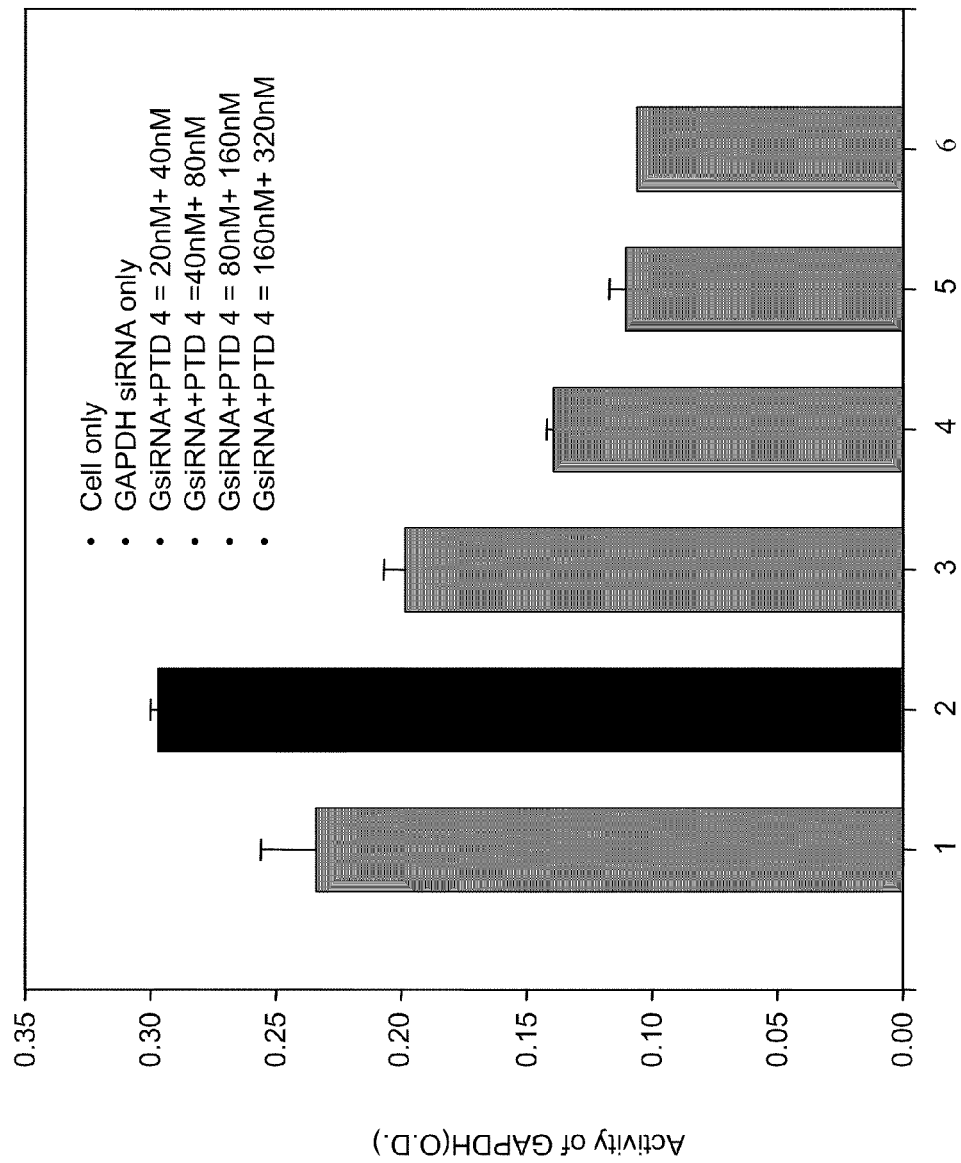

FIG. 11 shows that siRNA delivered with multimeric PTDs retain the ability to inhibit the activity of the target gene, GAPDH.

Figure 12:
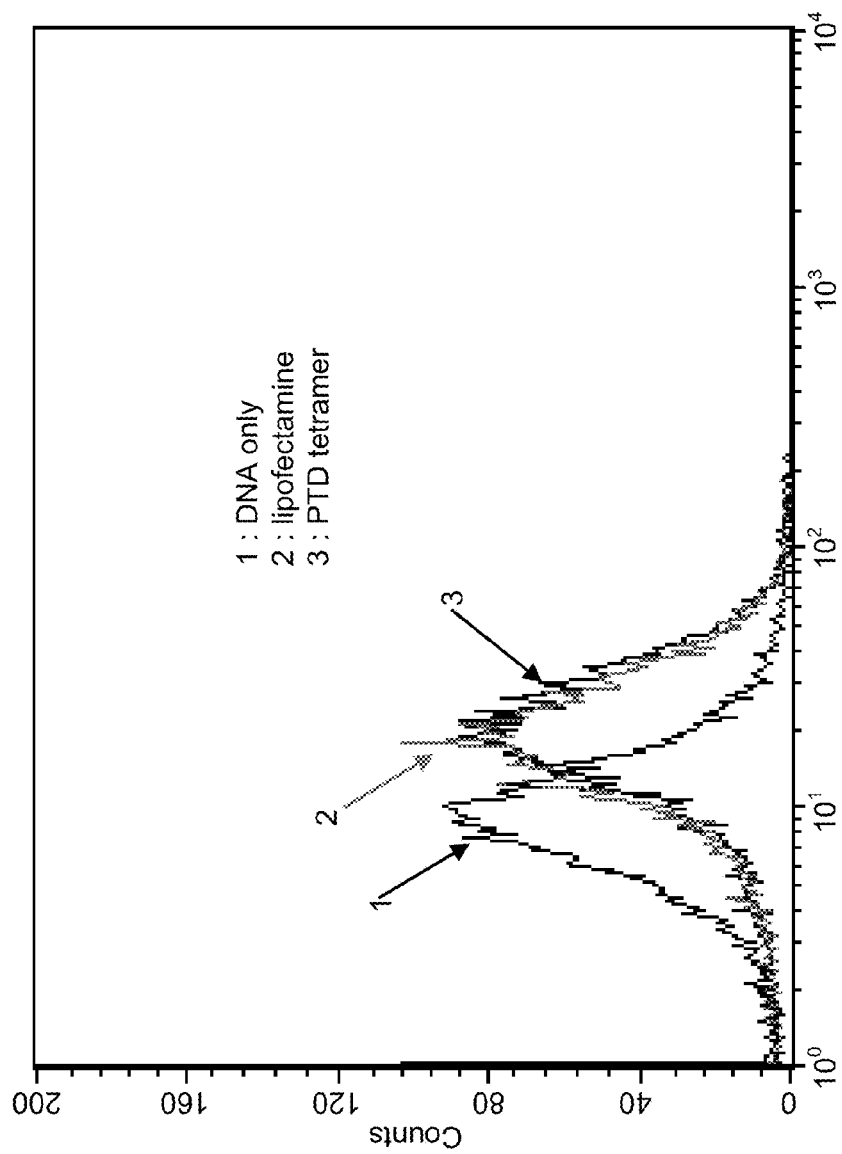

FIG. 12 shows that PTD tetramer can transduce plasmid DNA encoding EGFP into cells. The efficiency of delivery was analyzed by measuring the fluorescence of EGFP using FACS. FIG. 12 shows the height of fluorescence intensity for the 530/30 filter (FL-1H).

DETAILED DESCRIPTION OF THE INVENTION

The present invention encompasses methods of effectively delivering nucleic acids into cells in vivo or in vitro using one or more nucleic acid binding molecules. A nucleic acid binding molecule may be defined as a molecule which comprises a multimeric and/or spacer-incorporated PTD, and has the ability to bind to nucleic acids and deliver nucleic acids into cells. The nucleic acids delivered into cells may or may not be biologically active.

One embodiment of the present invention is a single-stranded nucleic acid comprising a phosphate backbone complexed or conjugated to a nucleic acid binding molecule containing one or more multimeric and/or spacer-incorporated PTDs that comprise one or more PTD molecules.

A preferred embodiment of the present invention is a single-stranded nucleic acid comprising a phosphate backbone complexed or conjugated to a nucleic acid binding molecule comprising a multimeric and/or spacer-incorporated PTD which comprises three or more PTD molecules.

The single-stranded nucleic acid comprising a phosphate backbone can be shRNA, antisense RNA, or cDNA (complementary DNA).

As used herein, the term "short hairpin RNA" or "shRNA" refers to an RNA molecule with a short loop and 19 to 27 base pairs in the stem. shRNA can selectively silence expression of genes that are homologous to the sequence in the double-stranded stem. Mammalian cells can convert shRNA into siRNA to mediate selective gene silencing (Paddison et al., *Genes and Dev.* 16(8):948-58 (2002)). Since shRNA is a single-stranded RNA that folds on itself to form a double-stranded structure (hairpin stem-loop structure), it can be considered a single-stranded as well as a double-stranded nucleic acid.

As used herein, the term "peptide nucleic acid" or "PNA" refers to a class of synthetic nucleobase oligomers that can sequence-specifically hybridize to nucleic acids and other polynucleobase strands. The PNA backbone is composed of repeating N-(2-aminoethyl)-glycine units linked by peptide bonds, instead of the deoxyribose and ribose sugar backbone with charged phosphate groups in DNA and RNA. Hybridization between nucleobases of polynucleobase strands typically follows well-established rules for hydrogen bonding. For Watson-Crick base pairing, typically adenine (A) base pairs with thymine (T) and cytosine (C) base pairs with guanine (G). Various other base-pairing motifs are well known in the nucleic acid arts.

Another embodiment of the invention is a double-stranded RNA complexed or conjugated to a nucleic acid binding molecule containing one or more multimeric and/or spacer-incorporated PTDs that comprise one or more PTD molecules.

A preferred embodiment is a double-stranded RNA complexed or conjugated to a nucleic acid binding molecule comprising a multimeric and/or spacer-incorporated PTD which comprises two or more PTD molecules.

The multimeric and/or spacer-incorporated PTD can comprise one or more spacers within or at the C- or N-terminus of the PTD(s). The spacer can be a protein or domain of a protein that cannot be complexed with nucleic acids. The spacer-incorporated PTDs may have a length corresponding to molecular weights of between 1-250 kd, 5-180 kd, 5-150 kd or 5-30 kd. For example, the Fc domain of an antibody, the whole antibody, albumin, adducin (alpha), adducin (beta), alpha-synuclein, AlphaA crystallin (Heat-shock protein beta-4; HspB4), AlphaB crystallin (heat-shock protein beta-5; Hsp5), apolipoprotein A-1 (Apo-A1), beta-galactosidase, clathrin coat assembly protein AP50, cytochrome-c-oxidase, green fluorescence protein (GFP), GTP binding protein Rheb, hemagglutinin, Ras GTPase, Rho-GTPase-activating protein (p50-rhoGAP), small proline-rich protein 2E (SPR-2E), tubulin alpha-1, tubulin beta-1, ubiquitin-like I-activating enzyme E1A, or ubiquitin-like I-activating enzyme E1B can be used as the spacer. A preferred spacer is ubiquitin (UB).

One embodiment of the invention is a nucleic acid binding molecule comprising a spacer-incorporated PTD, wherein the spacer-incorporated PTD contains one, two, three, four, five, six, seven, eight, nine, or ten PTDs and one or more spacers (for example, SEQ ID NOs: 1-60). Thus, the spacer-incorporated PTDs may comprise 1-20, 2-15, 2-10, 1-5, 2-8, 2-5, or 2-4 PTDs and one or more spacers. A spacer is an amino acid sequence that does not bind nucleic acid sequence.

The double-stranded RNA includes, but is not limited to, siRNA, crosslinked siRNA derivatives, shRNA, miRNA or engineered RNA precursors. The double-stranded RNA can be chemically synthesized, transcribed in vitro from a DNA template, or transcribed in vivo from an engineered RNA precursor.

As used herein, the term "short interfering RNA" or "siRNA" refers to any double-stranded RNA molecule comprising self-complementary sense and antisense regions, wherein the antisense region comprises a nucleotide sequence that is complementary to a nucleotide sequence in a target nucleic acid molecule for downregulating expression, or a portion thereof, and the sense region comprises a nucleotide sequence corresponding to the target nucleic acid sequence or portion thereof. The sense region is substantially identical in sequence to the target nucleic acid sequence or portion.

In a preferred embodiment, the siRNA of the present invention comprises a double-stranded RNA of 16-30 nucleotides, and, even more preferably, comprises a 21-nucleotide sense and a 21-nucleotide antisense strand paired so as to have a 19-nucleotide duplex region and a 2-nucleotide overhang at each of the 5' and 3' ends. Even more preferably, the 2-nucleotide 3' overhang comprises 2' deoxynucleotides (e.g., TT, for improved nuclease resistance).

As used herein, the term "microRNA" or "miRNA" refers to very small non-coding RNA produced from RNA-coding genes in the cell's own genome, of approximately 22 nucleotides in length, that appears to be involved in various aspects of mRNA regulation and degradation (Zeng et al., *Proc. Natl. Acad. Sci. USA*, 100(17):9779-84 (2003)).

Crosslinked siRNA derivatives are as described in U.S. patent application Ser. No. 10/672,069, which is incorporated herein by reference in its entirety. Crosslinking can be employed to alter the pharmacokinetics of the composition, for example, to increase the half-life in the body. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivate has at its 3' terminus a biotin molecule (e.g., a photocleavable biotin), a peptide, a peptidomimetic, a nanoparticle, organic compounds (e.g., a dye such as a fluorescent dye), or a dendrimer. Modifying siRNA derivatives in this way may improve cellular uptake or enhance cellular targeting activities of the resulting siRNA derivative as compared to the corresponding siRNA, and are useful for tracing the siRNA derivative in the cell, or improving the stability of the siRNA derivative compared to the corresponding siRNA. As such, one skilled in the art can screen crosslinked siRNA derivatives that are modified with various methods to determine whether the crosslinked siRNA derivatives possesses improved properties while maintaining the ability to mediate RNAi as are generally known in the art.

As used herein, the term "engineered," as in an engineered RNA precursor, indicates that the precursor is not found in nature, in that all or a portion of the nucleic acid sequence of the precursor is created or selected by man. Once created or selected, the sequence can be replicated, translated, transcribed, or otherwise processed by mechanisms within a cell. Thus, an RNA precursor produced within a cell from an engineered nucleic acid molecule, e.g., a transgene, is an engineered RNA precursor. Engineered RNA precursors are artificial constructs that are similar to naturally occurring precursors of small temporal RNA (stRNA) that are processed in the body to form siRNA. The engineered RNA precursors can be synthesized by standard methods known in the art, e.g., by use of an automated DNA synthesizer (such as are commercially available from Biosearch, Applied Biosystems, etc.) or encoded by nucleic acid molecules.

An additional embodiment is a double-stranded nucleic acid complexed or conjugated to a nucleic acid binding molecule containing one or more multimeric and/or spacer-incorporated PTDs that comprise one or more PTD molecules.

One embodiment is a double-stranded nucleic acid complexed or conjugated to a nucleic acid binding molecule comprising a multimeric PTD that comprises five or more PTD molecules.

The double-stranded nucleic acid includes, but is not limited to, double-stranded DNA vectors capable of expressing siRNA, double-stranded RNA, hybrid double-stranded nucleic acid, and circular RNA.

As used herein, the term "DNA vector" refers to a replicable nucleic acid construct used to express RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (siRNA, or shRNA which can be processed to an siRNA), and (3) appropriate transcription initiation and termination sequences. The choice of promoter and other regulatory elements generally varies according to the intended host cell. DNA vectors may be a circular or linearized plasmid, or other linear DNA which may also be non-infectious and nonintegrating (i.e., does not integrate into the genome of vertebrate cells). A linearized plasmid is a plasmid that was previously circular but has been linearized, for example, by digestion with a restriction endonuclease. Linear DNA may be advantageous in certain situations as discussed, e.g., in Cherng, J. Y., et al., *J. Control. Release* 60:343-53 (1999), and Chen, Z. Y., et al., *Mol. Ther.* 3:403-10 (2001), both of which are incorporated herein by reference. In the DNA vectors, regulatory elements controlling transcription can be generally derived from mammalian, microbial, viral or insect genes. The ability to replicate in a host, usually conferred by an origin of replication, and a selection gene to facilitate recognition of transformants may additionally be incorporated. Vectors derived from viruses, such as retroviruses, adenoviruses, and the like, may be employed.

As used herein, the term "hybrid double-stranded nucleic acid" refers to a double-stranded nucleic acid that has a similar function to double-stranded RNA. A hybrid double-stranded nucleic acid may be comprised of an RNA strand and a DNA strand.

Preferably, the RNA strand is the antisense strand and binds to the target mRNA. The hybrid double-stranded nucleic acid created by the hybridization of the DNA and RNA strands has a hybridized complementary portion and preferably at least one 3' overhanging end.

As used herein, the term "circular RNA" refers to a RNA molecule which contains two loop motifs, wherein one or both loop portions of the circular RNA is biodegradable. For example, a circular RNA of the invention is designed such that degradation of the loop portions in vivo can generate a double-stranded siRNA with 3'-terminal overhangs, such as 3'-terminal nucleotide overhangs comprising about 2 nucleotides.

One embodiment is a double-stranded RNA complexed or conjugated to a nucleic acid binding molecule comprising a multimeric PTD which comprises five or more PTD molecules.

Protein Transduction Domain (PTD)

The PTD is known to effectively allow delivery or uptake of proteins, peptides, nucleic acid and chemical compounds of interest in vivo and in vitro into cells.

For use as a multimeric and/or spacer-incorporated PTD in the present invention, the present inventors constructed several peptides produced by a recombinant protein producing process or a chemical synthetic process. It is to be understood that other kinds of PTD can be used depending on the desired delivery area and the kind of linker used. The PTD consists of 3-30 amino acids, preferably 5-15 amino acids, at least 10-30% of which are preferably arginine residues. However, PTDs without any arginine residues are also contemplated.

The multimeric and/or spacer-incorporated PTD can be a homo-multimer, including for example, homodimers, homotetramers, homohexamers and other homomultimers or a hetero-multimer, including for example, heterodimers, heterotetramers, heterohexamers and other heteromultimers. Embodiments of the invention include, but are not limited to, homo- or hetero-multimeric and/or spacer-incorporated PTDs that comprise combinations of one or more of the following:

```
Mouse transcription factor (MPH-1) or
human transcription factor (HPH-1)
YARVRRRGPRR;                              (SEQ ID NO:1)

Tat-PTD
(YGRKKRRQRRR);                            (SEQ ID NO:2)

Antp or penetratin
(RQIKIWFQNIRRMKWKK);                      (SEQ ID NO:3)

transportan
(CLIKKALAALAKLNIKLLYGASNLTWG);            (SEQ ID NO:4)

HSV-1 structural protein Vp22
(DAATATRGRSAASRPTERPRAPARSASRPRRPVE);     (SEQ ID NO:5)

polyarginine R7
(RRRRRRR);                                (SEQ ID NO:6)

membrane translocating sequence (MTS)
(AAVALLPAVLLALLAPAAADQNQLMP);             (SEQ ID NO:8)
``` short amphipathic peptide carriers including:

```
Pep-1
(KETWWETWWTEWSQPKKKKRKV),                 (SEQ ID NO:9)

Pep-2
(KETWFETWFTEWSQPKKKRKV),                  (SEQ ID NO:10)
and

Pep-3
(YGFKKFRKPWTWWETWWTE);                    (SEQ ID NO:11)

Sim-2
(AKAARQAAR);                              (SEQ ID NO:12)

MPG
(GALFLGFLGAAGSTMGAWSQPKKKRKV);            (SEQ ID NO:13)

KALA
(WEAKLAKALAKALAKHLAKALAKALKACEA);         (SEQ ID NO:14)
``` and branched polylysine (as described in U.S. Application No. 2006/0041058 and

Eom, K. D. et al., *J. Nanosci. Nanotechnol.* 6(11):3532-3538 (2006)). Sequences of the present invention (SEQ ID NOs: 15-20, 21, 31-42, 45, 57-60) wherein the C-terminal Cys is in parenthesis (as shown in Tables 1 and 2) are indicative that the Cys is optional. Thus, sequences with the C-terminal Cys removed are also contemplated and embodiments of the invention. A C-terminal cysteine may be used for conjugating to a siRNA. Conversely, sequences of the present invention not shown with a C-terminal Cys (SEQ ID NOs: 1-14, 22-30, 43, 44 and 46-56) may include a Cys at the C-terminus when conjugated to a siRNA.

Specific examples of the PTD multimers and/or spacer-incorporated PTDs of the present invention are listed in Tables 1 and 2.

TABLE 1

Examples of the PTD multimers of the present invention

| Multimer type | PTDs used | Sequence | SEQ ID NO. |
|---|---|---|---|
| Homodimer | MPH | YARVRRRGPRR GG YARVRRRGPRR | 7 |
| | TAT | YGRKKRRQRRR GG YGRKKRRQRRR | 22 |
| | Penetratin | RQIKIWFQNRRMKWKK GG RQIKIWFQNRRMKWKK | 23 |
| | Pep-1 | KETWWETWWTEWSQPKKKRKV GG KETWWETWWTEWSQPKKKRKV | 24 |
| Heterodimer | MPH + TAT | YARVRRRGPRR GG YGRKKRRQRRR | 25 |
| | MPH + penetratin | YARVRRRGPRR GG RQIKIWFQNRRMKWKK | 26 |
| | MPH + Pep-1 | YARVRRRGPRR GG KETWWETWWTEWSQPKKKRKV | 27 |
| | TAT + penetratin | YARVRRRGPRR GG RQIKTWFQNRRMKWKK | 28 |
| | TAT + Pep-1 | YARVRRRGPRR GG KETWWETWWTEWSQPKKKRKV | 29 |
| | Penetratin + Pep-1 | RQIKIWFQNRRMKWKK GG KETWWETWWTEWSQPKKKRKV | 30 |
| Homotetramer | MPH | YRF YARVRRRGPRR GGARF YARVRRRGPRR GGARF YARVRRRGPRR GGARF YARVRRRGPRR GGARV(C) | 20 |
| | TAT | YRF YGRKKRRQRRR GGARF YGRKKRRQRRR GGARF YGRKKRRQRRR GGARF YGRKKRRQRRR GGARV(C) | 31 |
| | Penetratin | YRF RQIKIWFQNRRMKWKK GGARF RQIKIWFQNRRMKWKK GGARF RQIKIWFQNRRMKWKK GGARF RQIKIWFQNRRMKWKK GGARV(C) | 32 |
| Heterotetramer | MPH + TAT | YRF YARVRRRGPRR GGARF YARVRRRGPRR GGARF YGRKKRRQRRR GGARF YGRKKRRQRRR GGARV(C) | 33 |
| | MPH + penetratin | YRF YARVRRRGPRR GGARF YARVRRRGPRR GGARF RQIKIWFQNRRMKWKK GGARF RQIKIWFQNRRMKWKK GGARV(C) | 34 |
| | TAT + penetratin | YRF YGRKKRRQRRR GGARF YGRKKRRQRRR GGARF RQIKIWFQNRRMKWKK GGARF RQIKIWFQNRRMKWKK GGARV(C) | 35 |
| | MPH + TAT + penetratin | YRF YARVRRRGPRR GGARF YARVRRRGPRR GGARF YGRKKRRQRRR GGARF RQIKIWFQNRRMKWKK GGARV(C) | 36 |
| Other homomultimer (hexamer) | MPH | YRF YARVRRRGPRR GGARF YARVRRRGPRR GGARF YARVRRRGPRR GGARF YARVRRRGPRR GGARF YARVRRRGPRR GGARF YARVRRRGPRR GGARV(C) | 37 |
| | TAT | YRF YGRKKRRQRRR GGARF YGRKKRRQRRR GGARF YGRKKRRQRRR YGRKKRRQRRR GGARF YGRKKRRQRRR GGARF GGARV(C) | 38 |
| | penetratin | YRF RQIKIWFQNRRMKWKK GGARF RQIKIWFQNRRMKWKK GGARF RQIKIWFQNRRMKWKK GGARF RQIKIWFQNRRMKWKK GGARF RQIKIWFQNRRMKWKK GGARV(C) | 39 |
| Other heteromultimer | MPH + TAT + MPH (hexamer) | YRF YARVRRRGPRR GGARF YARVRRRGPRR GGARF YARVRRRGPRR GGARF YGRKKRRQRRR GGARF YARVRRRGPRR GGARF YARVRRRGPRR GGARV(C) | 40 |
| | MPH + TAT + penetratin (hexamer) | YRF YARVRPRGPRR GGARF YARVRRRGPRR GGARF YGRKKRRQRRR GGARF YGRKKRRQRRR GGARF RQIKIWFQNRRMKWKK GGARF RQIKIWFQNRRMKWKK GGARV(C) | 41 |
| | MPH + penetratin + MPH | YRF YARVRRRGPRR GGARF YARVRRRGPRR GGARF RQIKIWFQNRRMKWKK GGARF RQIKIWFQNRRMKWKK GGARF YARVRRRGPRR GGARF YARVRRRGPRR GGAR(C) | 42 |

TABLE 2

Examples of spacer-incorporated PTDs comprising a spacer at either end or within.

| PTDs used | Sequence | SEQ ID NO. |
|---|---|---|
| MPH - UB* | YARVRRRGPRRGGQIFVKTLTGKTITLEVESSDTIDNVKSKIQDKEGIPPDQQRLIFAGKQLEDGRTLSDYNIQKESTLHLVLRLRGG | 43 |
| MPH(2) - a - UB | YARVRRRGPRRGGARFYARVRRRGPRRGGQIFVKTLTGKTITLEVESSDTIDNVKSKIQDKEGIPPDQQRLIFAGKQLEDGRTLSDYNIQKESTLHLVLRLRGG | 44 |
| MPH(2) - b - UB(v) | YARVRRRGPRRGGQIFVKTLTGKTITLEVESSDTIDNVKSKIQDKEGIPPDQQRLIFAGKQLEDGRTLSDYNIQKESTLHLVLRLRGVYARVRRRGPRRGGARV(C) | 45 |
| MPH(4) - UB | YARVRRRGPRRGGARFYARVRRRGPRRGGARFYARVRRRGPRRGGARFYARVRRRGPRRGG QIFVKTLTGKTITLEVESSDTIDNVKSKIQDKEGIPPDQQRLIFAGKQLEDGRTLSDYNIQKESTLHLVLRLRGG | 46 |
| TAT - UB | YGRKKRRQRRRGGQIFVKTLTGKTITLEVESSDTIDNVKSKIQDKEGIPPDQQRLIFAGKQLEDGRTLSDYNIQKESTLHLVLRLRGG | 47 |
| TAT(2) - a - UB | YGRKKRRQRRRGGARFYGRKKRRQRRRGGQIFVKTLTGKTITLEVESSDTIDNVKSKIQDKEGIPPDQQRLIFAGKQLEDGRTLSDYNIQKESTLHLVLRLRGG | 48 |

TABLE 2-continued

Examples of spacer-incorporated PTDs comprising a spacer at either end or within.

| PTDs used | Sequence | SEQ ID NO. |
|---|---|---|
| TAT(2) - b - UB(v) | YGRKKRRQRRRGGQIFVKTLTGKTITLEVESSDTIDNVKSKIQDKEGIPPDQQRLIFAGKQLEDGR TLSDYNIQKESTLHLVLRLRGVYGRKKRRQRRR | 49 |
| TAT(4) - UB | YGRKKRRQRRRGGARFYGRKKRRQRRRGGARFYGRKKRRQRRRGGARFYGRKKRRQRRRGG QIFVKTLTGKTITLEVESSDTIDNVKSKIQDKEGIPPDQQRLIFAGKQLEDGRTLSDYNIQKESTLH LVLRLRGG | 50 |
| Penetratin - UB | RQIKIWFQNRRMKWKKGGQIFVKTLTGKTITLEVESSDTIDNVKSKIQDKEGIPPDQQRLIFAGK QLEDGRTLSDYNIQKESTLHLVLRLRGG | 51 |
| Penetratin(2) - UB (v) | RQIKIWFQNRRMKWKK GG QIFVKTLTGKTITLEVESSDTIDNVKSKIQDKEGIPPDQQRLIFAGK QLEDGRTLSDYNIQKESTLHLVLRLRGVRQIKIWFQNRRMKWKK | 52 |
| Pep-1(2) - UB(v) | KETWWETWWTEWSQPKKKRKVGGQIFVKTLTGKTITLEVESSDTIDNVKSKIQDKEGIPPDQQR LIFAGKQLEDGRTLSDYNIQKESTLHLVLRLRGV KETWWETWWTEWSQPKKKRKV | 53 |
| MPH - UB(v) + TAT | YARVRRRGPRRGGQIFVKTLTGKTITLEVESSDTIDNVKSKIQDKEGIPPDQQRLIFAGKQLEDGR TLSDYNIQKESTLHLVLRLRGVYGRKKRRQRRR | 54 |
| Sim-2 - UB(v) + MPH | AKAARQAARGGGQIFVKTLTGKTITLEVESSDTIDNVKSKIQDKEGIPPDQQRLIFAGKQLEDGR TLSDYNIQKESTLHLVLRLRGVYARVRRRGPRR | 55 |
| Penetratin - UB(v) + MPH | RQIKIWFQNRRMKWKKGGQIFVKTLTGKTITLEVESSDIDNVKSKIQDKEGIPPDQQRLIFAGK QLEDGRTLSDYNIQKESTLHLVLRLRGVYARVRRRGPRR | 56 |
| Penetratin - UB(v) + MPH(2) | RQIKIWFQNRRMKWKKGGQIFVKTLTGKTITLEVESSDTIDNVKSKIQDKEGIPPDQQRLIFAGK QLEDGRTLSDYNIQKESTLHLVLRLRGVSRVYARVRRRGPRRGGARFYARVRRRGPRRGGARV (C) | 57 |
| Penetratin - UB(v) + MPH(4) | RQIKIWFQNRRMKWKKGGQIFVKTLTGKTITLEVESSDTIDNVKSKIQDKEGIPPDQQRLIFAGK QLEDGRTLSDYNIQKESTLHLVLRLRGVSRVYARVRRRGPRRGGARFYARVRRRGPRRGGARF YARVRRRGPRRGGARFYARVRRRGPRRGGARV(C) | 58 |
| Sim-2 - UB(v) + PTD (Hph-1)-(2) | AKAARQAARGGGQIFVKTLTGKTITLEVESSDTIDNVKSKIQDKEGIPPDQQRLIFAGKQLEDGR TLSDYNIQKESTLHLVLRLRGVSRVYARVRRRGPRRGGARFYARVRRRGPRRGGARV(C) | 59 |
| Sim-2 - UB(v) + PTD (Hph-1)-(4) | AKAARQAARGGGQIFVKTLTGKTITLEVESSDTIDNVKSKIQDKEGIPPDQQRLIFAGKQLEDGR TLSDYNIQKESTLHLVLRLRGVSRVYARVRRRGPRRGGARFYARVRRRGPRRGGARFYARVRR RGPRRGGARFYARVRRRGPRRGGARV(C) | 60 |

*UB(v) is the mutant form of UBiquitin, wherein the Gly residue of the carboxyl terminus is substituted by Val. The sequences (SEQ ID NOs: 20, 31-42, 45, 57-60) that end with (C) mean that the Cys is optional. Sequences with the C-terminal Cys removed are also contemplated and embodiments of the invention.

Substantially similar variants of these PTDs are also contemplated, e.g., a variant that is at least 65% identical thereto. Of course, the percent identity can be higher, e.g., 65%, 67%, 69%, 70%, 73%, 75%, 77%, 83%, 85%, 87%, 90%, 91%, 92%, 93%, 94%, 95%, 96%, 97%, 98%, or 99% identity. In general, the substitutions are conservative substitutions. The methods of making such PTD variants are routine in the art.

The PTDs or the variants thereof can also have substitutions, deletions or additions. Alterations may produce conservative or non-conservative amino acid substitutions, deletions or additions. In some embodiments the substitution, deletion or insertion is of 1, 2, 3, 4 or 5 amino acids. The skilled artisan is fully aware of amino acid substitutions that are either less likely or not likely to significantly effect protein function (e.g., replacing one aliphatic amino acid with a second aliphatic amino acid). For example, guidance concerning how to make phenotypically silent amino acid substitutions is provided in Bowie, J. U. et al., "Deciphering the Message in Protein Sequences: Tolerance to Amino Acid Substitutions," Science 247:1306-1310 (1990).

The PTDs or the variants thereof can also have modified backbones, e.g., oligocarbamate or oligourea backbones (see, e.g., Wang et al., J. Am. Chem. Soc. 119:6444-6445 (1997);
Tamilarasu et al., J. Am. Chem. Soc. 121:1597-1598 (1999); Tamilarasu et al., Bioorg. Of Med. Chem. Lett. 11:505-507 (2001)).

Nucleic Acid Binding Region

In all above mentioned embodiments, the nucleic acid binding molecule can further comprise one or more nucleic acid binding regions. A "nucleic acid binding region" is defined as a region capable of binding to nucleic acid. Cationic substances capable of electrostatically binding to a nucleic acid, for example, polylysine, polyarginine, any other polymer of amino acids having basic side chains, or polyethylenimine (PEI), or the like, may be used. Cationic substances are believed to bind nucleic acid in a sequence-independent manner through electrostatic interactions between the cationic substances and the anionic nucleic acid phosphate backbone. It would be understood by a person skilled in the art that the strength of the interaction between a cationic substance and DNA will reflect, among other things, the overall net charge of the cationic substance.

Suitable cationic substances include polylysine, for example, having from 10 to 20 lysine residues, or from 15 to 17 residues, especially 16 residues, i.e., $K_{16}$. Poly-L-lysine and poly-D-lysine that have a molecular weight of 3.4 kDa (with an average of 16 positive charges per molecule) are preferred. Other suitable polymers include PEI which has a molecular weight of 2 kDa (with an average of 12 positive charges per molecule at neutral pH). A PTD itself is a highly positively charged molecule, and can likewise be used as well. The term "nucleic acid binding region" is intended to encompass any substance capable of binding to nucleic acid with the same mechanism as the above-described substances.

When a nucleic acid binding region, in addition to a multimeric and/or spacer-incorporated PTD, is part of a nucleic acid binding molecule, the nucleic acid binding region can bind to the nucleic acid such that the probability for PTD to bind to the nucleic acid can be decreased. Thus, the probability of the PTD to maintain its original structure can be increased, to maintain the ability of PTD to be delivered into cells. The ability of a PTD to be delivered into cells does not require the PTD to directly bind to a cargo. The delivery effect of a PTD is maintained even when the nucleic acid binding region is present and prevents the PTD from binding directly to a nucleic acid (FIG. 1A).

Accordingly, when a PTD is used as a nucleic acid binding region, and a multimeric and/or spacer-incorporated PTD is used as a nucleic acid carrier to deliver a nucleic acid into cells, the efficiency thereof for delivering the nucleic acid into cells will be greatly increased (FIG. 1B).

Methods of Production

The invention also encompasses methods of producing any one of the above nucleic acid molecules complexed or conjugated to a nucleic acid binding molecule comprising a multimeric and/or spacer-incorporated PTD with or without a nucleic acid binding region.

The multimeric and/or spacer-incorporated PTD can be produced by a chemical synthetic process or by a recombinant protein producing process. To produce a tetramer or a hexamer, conjugation of dimers through covalent bonds such as a disulfide bond can be utilized. In a preferred embodiment, a cysteine residue is located at the terminal end of two PTD dimers. Then the induction of a disulfide bond is performed using an air oxidation method with slow stirring at low temperature at pH 8-11. A hexamer can be prepared in this manner by combining a dimer and a tetramer.

The binding between a nucleic acid and a nucleic acid binding molecule can be a non-covalent bond when the binding is through electrostatic interaction. When a nucleic acid and a nucleic acid binding molecule are mixed at a certain ratio, a complex is formed. A ratio of nucleic acid to nucleic acid binding molecule between 1:1 to 1:20, 1:1 to 1:3, or 1:2, can be used to produce the complex.

The binding between a nucleic acid and a nucleic acid binding molecule can also occur via a covalent bond such as a disulfide bond or an amide bond. Any suitable bond (e.g., ester bonds, carbamate bonds, sulfonate bonds, thioester bonds, thioether bonds, etc.) may be created according to methods generally and well known in the art. To form a disulfide bond between the nucleic acid and the nucleic acid binding molecule, the two molecules may be derivatized to bear thiol groups, one of which can bear a leaving group. The modified nucleic acid is then incubated together with the nucleic acid binding molecule that is prepared for linkage, for a sufficient time (and under such appropriate conditions of temperature, pH, molar ratio, etc.) as to generate a disulfide bond between the nucleic acid and the nucleic acid binding molecule. Numerous methods and strategies of forming a covalent bond will be readily apparent to one of ordinary skill in the art, as will the conditions required for efficient binding.

This invention also encompasses methods of facilitating delivery of any one of the above nucleic acid molecules complexed or conjugated to a nucleic acid binding molecule into a cell, comprising: (i) producing a nucleic acid complexed or conjugated with a nucleic acid binding molecule that comprises a multimeric and/or spacer-incorporated PTD; (ii) adding the nucleic acid complexed or conjugated with the nucleic acid binding molecule into a cell culture medium; and (iii) incubating the cell in the cell culture medium prepared in step (ii).

The step of incubating the cell in the cell culture medium is defined as incubating the cell for such a period of time, and under such conditions of concentration, temperature, pH, etc., as to result in delivery of the nucleic acid into the cell. Specific protocols using the present invention will vary according to a number of factors (such as cell type, size of nucleic acid, PTD used, etc.), but will be readily apparent to one of ordinary skill in the art.

Biological Uses

This invention also encompasses methods of determining the function of a target gene in a cell using a nucleic acid complexed or conjugated to a nucleic acid binding molecule that comprises a multimeric and/or spacer-incorporated PTD, comprising: (i) adding the nucleic acid complexed or conjugated to the nucleic acid binding molecule into a cell culture medium; (ii) incubating the cell in the cell culture medium prepared in step (i), so that the nucleic acid is delivered into the cell in an amount sufficient to inhibit expression of the target gene; (iii) maintaining the cell, in which the corresponding mRNA of the target gene is degraded; and (iv) observing and comparing the phenotype of the cell to that of an appropriate control cell, thereby obtaining information regarding the function of the target gene in the cell.

A number of options are available to detect inhibition of expression of the target gene. Suitable assays include, e.g., examination of levels of protein encoded by the target gene or levels of mRNA transcribed from the target gene using techniques known to those of skill in the art such as dot blots, northern blots, in situ hybridization, ELISA, immunoprecipitation, enzyme function, as well as other assays known to those of skill in the art. A number of methods are available for detecting the target gene mRNA levels. Such methods include, for example, dot blot analysis, in-situ hybridization, RT-PCR, quantitative reverse-transcription PCR, Northern blots, and nucleic acid probe array methods. Similarly, various methods can be utilized to detect changes in protein levels. Exemplary methods include, but are not limited to, Western blot analysis, performing immunological analyses utilizing an antibody that specifically binds to the protein followed by detection of complex formed between the antibody and protein, and activity assays, provided the protein has a detectable activity. In general, protein or mRNA levels in the cell incubated with the nucleic acid complexed or conjugated to the nucleic acid binding molecules are compared to a control cell which is not incubated with the nucleic acid complexed or conjugated to the nucleic acid binding molecules to determine whether the nucleic acid is delivered into the cell and inhibits expression of the target gene.

The phenotype of the cell can be observed to detect a phenotypical change that is correlated with inhibition of expression of the target gene. Such phenotypical changes can include, for instance, apoptosis, morphological changes, changes in cell proliferation, as well as other cellular activities. If interference with expression of a particular gene leads to decrease or increase in one or more of these cellular activities, the target gene's function can be assigned to one or more of these cellular pathways. The present invention is also directed to therapeutic methods to block or activate expression of the target gene.

A "target gene" is a gene whose expression is to be selectively inhibited or "silenced". This silencing is achieved by promoting the degradation of the mRNA of the target gene that is induced by the binding between a shRNA, antisense RNA, miRNA, siRNA, an engineered RNA precursor, hybrid double-stranded nucleic acid or circular RNA and the mRNA of the target gene. One portion or segment of these molecules is an anti-sense strand that is substantially complementary to a portion, e.g., about 16 to about 40 or more nucleotides, of the mRNA of the target gene. Any gene previously identified by genetics or by sequencing may represent a target. Target genes may include developmental genes and regulatory genes as well as metabolic or structural genes or genes encoding enzymes. The target gene of the present invention may be a gene that is endogenous to the cell, as in the case of a regulatory gene or a gene coding for a native protein; alternatively, the target gene may be heterologous or exogenous in relation to the cell, as in the case of a viral or bacterial gene, transposon, or transgene.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The present invention is not limited to methods of determining the function of a single target gene, but also encompasses methods of determining the function of genome-wide genes. Approaches to design RNAi libraries in functional genomic are described in Huesken, D. et al., *Nat. Biotechnol.* 23(8): 995-1001 (2005), Vanhecke, D. and Janitz, M. *Drug Discov. Today* 10(3): 205-12 (2005), and Janitz, M. et al., *Handb. Exp. Pharmacol.* 97-104 (2006).

Therapeutic Uses

The present invention also encompasses therapeutic methods of inhibiting expression of a target gene in a cell using a nucleic acid complexed or conjugated to a nucleic acid binding molecule. Thus, one embodiment of the present invention encompasses methods of treating a wide range of diseases and disorders amenable to treatment by modification of gene expression. The present invention can be effectively employed to prevent, modulate the occurrence or severity of, or treat (alleviate one or more symptom(s) to a detectable or measurable extent) of a disease state or other adverse condition in a patient. Within these and related therapeutic compositions and methods, the use of crosslinked siRNA derivatives will often improve properties of the modified siRNA in comparison to properties of native siRNA molecules, for example by providing increased resistance to nuclease degradation in vivo, and/or through improved cellular uptake. As can be readily determined according to the disclosure herein, crosslinked siRNA derivatives having multiple chemical modifications will retain their RNA interference (RNAi) activity. Thus, the present invention provides useful reagents and methods for a variety of therapeutic, diagnostic, target validation, genomic discovery, genetic engineering, and pharmacogenomic applications.

The present invention satisfies additional objects and advantages by providing nucleic acids or fragments thereof that modulate expression of genes associated with a particular disease state or other adverse condition in a subject. Typically, the nucleic acid will target a gene that is expressed at an elevated level as a causal or contributing factor associated with the subject disease state or adverse condition. In this context, the expression of the gene will be effectively down-regulated to levels that will prevent, alleviate, or reduce the severity or recurrence of one or more associated disease symptoms. Alternatively, for various distinct disease models where expression of the target gene is not necessarily elevated as a consequence or sequel of disease or other adverse condition, down regulation of the target gene will nonetheless result in a therapeutic result by lowering gene expression (i.e., to reduce levels of a selected mRNA and/or protein product of the target gene).

Alternatively, the present invention may be targeted to lower expression of one gene, which can result in upregulation of a "downstream" gene whose expression is negatively regulated by a product or activity of the target gene. Comparable methods are provided that target expression of one or more different genes associated with a selected disease condition in animal subjects, including any of a large number of genes whose expression is known to be aberrantly increased as a causal or contributing factor associated with the selected disease condition. The present invention can be administered in conjunction with other standard therapeutic agents for a targeted disease condition.

By "modulate gene expression" is meant that the expression of a target gene is upregulated or downregulated, which can include upregulation or downregulation of mRNA levels present in a cell, or of mRNA translation, or of synthesis of protein or protein subunits, encoded by the target gene. Modulation of gene expression can be determined also by the presence, quantity, or activity of one or more proteins or protein subunits encoded by the target gene that is up regulated or down regulated, such that expression, level, or activity of the subject protein or subunit is greater than or less than that which is observed in the absence of the modulator (e.g., a siRNA). For example, the term "modulate" can mean "inhibit" or "lower", but the use of the word "modulate" is not limited to this definition.

By "inhibit", "down-regulate", or "reduce" expression, it is meant that the expression of the gene, or level of RNA molecules or equivalent RNA molecules encoding one or more proteins or protein subunits, or level or activity of one or more proteins or protein subunits encoded by a target gene, is reduced below that observed in the absence of the nucleic acid molecules of the invention. In one embodiment, inhibition, down-regulation or reduction is below the level observed in the presence of an inactive or attenuated molecule. In another embodiment, inhibition, down-regulation, or reduction is below that level observed in the presence of, for example, a nucleic acid with a scrambled sequence or with mismatches. In another embodiment, inhibition, down-regulation, or reduction of gene expression with a nucleic acid of the instant invention is greater in the presence of the nucleic acid than in its absence.

The phrase "inhibiting expression of a target gene" refers to the ability of the molecules of the invention to down-regulate the target gene. To examine the extent of down-regulation, samples or assays of the organism of interest or cells in culture expressing a particular construct are compared to control samples lacking expression of the construct. Control samples (lacking construct expression) are assigned a relative value of 100%. Inhibition of expression of a target gene is achieved when the test value relative to the control is about 90%, often 50%, and in certain embodiments 25% to 0%. Suitable assays include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

By "subject" is meant an organism, tissue, or cell, which may include an organism as the subject or as a donor or recipient of explanted cells or the cells that are themselves subjects for nucleic acid delivery. "Subject" therefore may refer to an organism, organ, tissue, or cell, including in vitro or ex vivo organs, tissue or cellular subjects, to which the nucleic acid molecules of the invention can be administered and enhanced by polynucleotide delivery-enhancing polypeptides described herein. Exemplary subjects include mammalian individuals or cells, for example, human patients or cells.

Within exemplary embodiments, the compositions and methods of the invention are useful as therapeutic tools to regulate expression of tumor necrosis factor-$\alpha$ (TNF-$\alpha$) to treat or prevent symptoms of rheumatoid arthritis (RA). In this context, the invention further provides compounds, compositions, and methods useful for modulating expression and activity of TNF-$\alpha$ by RNAi using double-stranded RNA. In more detailed embodiments, the invention provides double-stranded RNA, such as siRNA, miRNA, and shRNA, and related methods, that are effective for modulating expression of TNF-$\alpha$ and/or TNF-$\alpha$ genes to prevent or alleviate symptoms of RA in mammalian subjects.

The present invention may be administered in any form, for example transdermally or by local injection (e.g., local injection at sites of psoriatic plaques to treat psoriasis, or into the joints of patients afflicted with psoriatic arthritis or RA). In more detailed embodiments, the invention provides formulations and methods to administer therapeutically effective amounts of double-stranded RNA directed against a mRNA of TNF-$\alpha$, which effectively down-regulate the TNF-$\alpha$ RNA and thereby reduce or prevent one or more TNF-$\alpha$-associated inflammatory condition(s).

In another embodiment, the present invention also encompasses methods of treating cancer by silencing genes differentially upregulated in tumor cells or genes involved in cell division.

The molecules of the present invention can be administered to cells by a variety of methods known to those of skill in the art, including, but not restricted to, administration within formulations that comprise a nucleic acid complexed or conjugated to a nucleic acid binding molecule alone, or that further comprise one or more additional components, such as a pharmaceutically acceptable carrier, diluent, excipient, adjuvant, emulsifier, buffer, stabilizer, preservative, and the like. In certain embodiments, the nucleic acid complexed or conjugated to the nucleic acid binding molecule can be encapsulated in liposomes, or incorporated into other vehicles, such as hydrogels, cyclodextrins, biodegradable nanocapsules, bioadhesive microspheres, or proteinaceous vectors (see e.g., International PCT Publication No. WO 00/53722). Alternatively, a nucleic acid/nucleic acid binding molecule/vehicle combination can be locally delivered by direct injection or by use of an infusion pump. Direct injection, whether subcutaneous, intramuscular, or intradermal, can take place using standard needle and syringe methodologies, or by needle-free technologies such as those described in Conry et al., Clin. Cancer Res. 5:2330-2337 (1999) and International PCT Publication No. WO 99/31262. The compositions of the present invention may also be formulated and used as tablets, capsules or elixirs for oral administration, suppositories for rectal administration, sterile solutions, suspensions for injectable administration, and the other compositions known in the art.

A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity.

By "systemic administration" is meant in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular. Each of these administration routes expose the desired negatively charged nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS (Jolliet-Riant and Tillement, Fundam. Clin. Pharmacol. 13:16-26 (1999)); biodegradable polymers, such as poly (DL-lactide-coglycolide) microspheres for sustained release delivery after intracerebral implantation (Emerich, D. F. et al., Cell Transplant 8:47-58 (1999)); and loaded nanoparticles, such as those made of polybutylcyanoacrylate, which can deliver drugs across the blood brain barrier and can alter neuronal uptake mechanisms (Schroeder, U. et al., Prog. Neuropsychopharmacol. Biol. Psychiatry 23(5):941-949 (1999)). Other non-limiting examples of delivery strategies for the nucleic acid molecules of the instant invention include material described in Boado et al., J. Pharm. Sci. 87:1308-1315 (1998); Tyler et al., FEBS Lett. 421:280-284 (1999); Pardridge et al., PNAS USA 92:5592-5596 (1995); Boado, Adv. Drug Delivery Rev. 15:73-107 (1995); Aldrian-Herrada et al., Nucleic Acids Res. 26:4910-4916 (1998); and Tyler et al., PNAS USA 96:7053-7058 (1999).

The present invention also includes compositions prepared for storage or administration, which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). For example, preservatives, stabilizers, dyes and flavoring agents may be provided. These include sodium benzoate, sorbic acid and esters of p-hydroxybenzoic acid. In addition, antioxidants and suspending agents may be used.

A "pharmaceutically effective dose" is that dose required to prevent, inhibit the occurrence of, or treat (alleviate a symptom to some extent, preferably all of the symptoms of) a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. The data obtained from the cell culture assays and animal studies can be used in formulating a range of dosages for use in humans. The dosage of such compounds lies preferably within a range of circulating concentrations that include the $ED_{50}$ with little or no toxicity. The dosage may vary within this range depending upon the dosage form employed and the route of administration utilized. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a pharmaceutically effective dose of the present invention depends on the nucleic acid selected. For instance, if a plasmid encoding shRNA is selected, single dose amounts in the range of approximately 1 μg to 1000 mg may be administered; in some embodiments, 10, 30, 100 or 1000 μg can be administered. In some embodiments, 1-5 g of the compositions can be administered. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject can include a single treatment or, preferably, can include a series of treatments.

For oral administration, the present invention may be presented as capsules or tablets, powders, granules, or a suspension. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. The composition may be further presented in convenient unit-dosage form, and may be prepared using a controlled-release formulation, buffering agents, and/or enteric coatings.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

The pharmaceutical compositions can be in the form of a sterile injectable aqueous or oleaginous suspension. This suspension can be formulated according to known techniques using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The present invention can also be administered in the form of suppositories, e.g., for rectal administration of the drug. These compositions can be prepared by mixing the drug with a suitable non-irritating excipient that is solid at room temperature but liquid at rectal temperature and will therefore melt in the rectum to release the drug. Such materials include cocoa butter and polyethylene glycols.

For administration by inhalation, the present invention may be delivered in the form of an aerosol spray from a pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The present invention can also be administered by any method suitable for administration of nucleic acid agents, e.g., using gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol. 88(2):205-210 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

DEFINITIONS

For convenience, certain terms used in the specification, examples, and appended claims are collected here. Unless otherwise defined, all technical and scientific terms used herein have the same meaning as commonly understood by one of ordinary skill in the art to which this invention pertains.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Sugar, base and phosphate modifications can be introduced into nucleic acid molecules to prevent degradation of the nucleic acid by serum ribonucleases, therefore increasing their potency. For example, oligonucleotides can be modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (see Usman and Cedergren, TIBS 17:34 (1992); Usman et al., Nucleic Acids Symp. Ser. 31:163 (1994); and Burgin et al., Biochemistry 35:14090 (1996)). Sugar modification of nucleic acid molecules has been extensively described in the art. See International Publication No. WO 91/03162; International Publication PCT No. WO 92/07065; International Publication PCT No. WO 93/15187; International PCT publication No. WO 97/26270; International PCT Publication No. WO 98/13526; U.S. Pat. Nos. 5,334,711;5,627,053;5,716,824; 6,300,074; Perrault et al., Nature 344:565-568 (1990); Pieken et al., Science 253: 314-317 (1991); Usman and Cedergren, Trends in Biochem. Sci. 17:334-339 (1992); Beigelman et al., J. Biol. Chem. 270:25702 (1995); Karpeisky et al., Tetrahedron Lett. 39:1131 (1998); Earnshaw and Gait, Biopolymers (Nucleic Acid Sciences) 48:39-55 (1998); Verma and Eckstein, Annu. Rev. Biochem. 67:99-134 (1998); and Burlina et al., Bioorg. Med. Chem. 5:1999-2010 (1997). All of the above references describe general methods and strategies to determine the location of incorporation of sugar, base and/or phosphate modifications and the like into nucleic acid molecules without modulating catalysis.

In view of such teachings, similar modifications can be used as described herein to modify the nucleic acid of the instant invention so long as the ability to promote RNAi in cells is not significantly inhibited. While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

The nucleic acids of the present invention can also be labeled using any method known in the art; for instance, the nucleic acids can be labeled with a fluorophore, e.g., Cy3, fluorescein, or rhodamine. The labeling can be carried out using a kit, e.g., the SILENCER™ siRNA labeling kit (Ambion). Additionally, the nucleic acid can be radiolabeled, e.g., using $^3$H, $^{32}$P, or other appropriate isotope.

By "RNA" is meant a molecule comprising at least one ribonucleotide residue. By "ribonucleotide" is meant a nucleotide with a hydroxyl group at the 2' position of a β-D-ribofuranose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or internally, for example at one or more nucleotides of the RNA. Nucleotides in the RNA molecules of the present invention can also comprise non-standard nucleotides, such as non-naturally occurring nucleotides or chemically synthesized nucleotides or deoxynucleotides. These altered RNA molecules can be referred to as RNA analogs or analogs of naturally-occurring RNA.

By "sense region" is meant a nucleotide sequence of a nucleic acid having complementarity to an antisense region of the nucleic acid. In addition, the sense region of a nucleic acid can comprise a nucleic acid sequence having homology with a target nucleic acid sequence.

By "antisense region" is meant a nucleotide sequence of a nucleic acid having complementarity to a sense region of the nucleic acid. In addition, the antisense region of a nucleic acid can comprise a nucleic acid sequence having homology with a target nucleic acid sequence.

As used herein, the term "complexed" refers to the interaction between two molecules that is mediated through a non-covalent bond. There are four main types of non-covalent bonds: hydrogen bonds, ionic interactions, Van der Waals interactions, and hydrophobic bonds. The positively charged PDT can form a non-covalent electrostatic complex with negatively charged nucleic acids as aggregates, nanoparticles or a soluble complex.

As used herein, the term "conjugated" refers to the interaction between two molecules that is mediated through a covalent bond. Covalent bonds are generally stable.

Examples of a covalent bond include, but are not limited to, a disulfide bond, or an amide bond. However, it will be apparent to those skilled in the art that a wide variety of functional groups may be used so that a wide variety of covalent bonds may be applicable (e.g., ester bonds, carbamate bonds, sulfonate bonds, thioester bonds, or thioether bonds). The covalent bond can be present at the 3'-end, 5'-end, or both the 3'-end and 5'-end, of either the sense strand, the antisense strand, or both strands of the chemically-modified nucleic acid molecule.

As used herein, the term "multimeric PTD" refers to a peptide chain which contains more than one domain and linker between the domains. The domains in the multimeric peptides of the invention can be the same to form homo-multimers or different from each other to form hetero-multimers. The homo- or hetero-multimers can comprise dimers, trimers, tetramers, pentamers, hexamers or higher multimers. Typically, the linker consists of one to five amino acids followed by amino acid residues such as cysteine residues, that allow cross-linking to other monomers. Although cysteine residues are preferred since they are able to form disulfide bridges between two peptide molecules, other means of multimerising peptide chains are known to the person skilled in the art. For example, in place of cysteine residues, amino acid residues or other chemical entities such as artificial amino acids may be included which are capable of being chemically cross-linked (e.g., sugar residues; Marcaurelle et al., *Tetrahedron Lett.* 39:8417-8420 (1998), incorporated herein by reference).

A "target gene" is a gene whose expression is to be selectively inhibited or silenced. This silencing can be achieved by promoting the degradation of the mRNA of the target gene or by inhibiting translation of the mRNA of the target gene. The degradation or translational inhibition can be induced by the binding between a shRNA, antisense RNA, miRNA, siRNA, an engineered RNA precursor, hybrid double-stranded nucleic acid or circular RNA and the mRNA of the target gene. One portion or segment of these mentioned molecules is an anti-sense strand that is substantially complementary to a portion, e.g., about 16 to about 40 nucleotides, of the mRNA of the target gene. Any gene previously identified by genetics or by sequencing may represent a target. Target genes may include developmental genes and regulatory genes as well as metabolic or structural genes or genes encoding enzymes. The target gene may be expressed in those cells in which a phenotype is being investigated or in an organism in a manner that directly or indirectly impacts a phenotypic characteristic. The target gene of the present invention may be a gene that is endogenous to the cell, as in the case of a regulatory gene or a gene coding for a native protein; alternatively, the target gene may be heterologous or exogenous in relation to the cell, as in the case of a viral or bacterial gene, transposon, or transgene. In either case, uninhibited expression of the target gene may result in a disease or a condition.

The phrase "substantially identical," in the context of two nucleic acids, refers to two or more sequences or subsequences that have at least 75%, preferably at least 80% or 85%, more preferably at least 90%, 95%, 96%, 97%, 98% or 99% nucleotide identity, when compared and aligned for maximum correspondence, as measured using a sequence comparison algorithm such as those described below for example, or by visual inspection. Preferably, the substantial identity exists over a region of the sequences that is at least about 16-40 nucleotides in length, or 40-60 nucleotides in length, in other instances over a region at least 60-80 nucleotides in length, in still other instances at least 90-100 nucleotides in length, and in yet other instances the sequences are substantially identical over the full length of the sequences being compared, such as the coding region of a nucleotide.

As used herein, the term "substantially complementary" is defined as two sequences that are sufficiently complementary to hybridize under specified hybridization conditions. A variety of hybridization conditions may be used in the present invention, including high, moderate and low stringency conditions. High stringency conditions are known in the art; see for example Maniatis et al., *Molecular Cloning: A Laboratory Manual*, 2nd Edition (1989), and Ausubel et al., *Short Protocols in Molecular Biology* (1989), both of which are hereby incorporated by reference. Generally, high stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target sequence hybridize to the target sequence at equilibrium (as the target sequences are present in excess, at Tm, 50% of the probes are occupied at equilibrium). High stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). High stringent conditions may also be achieved with the addition of destabilizing agents such as formamide. Moderate or low stringency conditions may also be used, as are known in the art.

The present invention is described in the following Examples, which are set forth to aid in the understanding of the invention, and should not be construed to limit in any way the scope of the invention as defined in the claims which follow thereafter.

EXAMPLES

Example 1

Chemical Synthesis of a Multimeric PTD

Peptides were synthesized according to the standard stepwise fluoren-9-yl methoxycarbonyl (Fmoc) solid-phase method using 2-Chlorotrityl Resin with Peptide Auto Synthesizer (Symphony, PTI, Tucson, Ariz.). Fmoc amino acids were stored in 0.2 M 1-Methyl-2-pyrrolidone (NMP) solution. Coupling reagents (DIC, HOBt) were pre-dissolved in the 0.2 M NMP solution. All Fmoc amino acids were in 5-fold excess of the coupling reagents. The coupling time was 30 min. Fmoc deprotections were performed with 20% piperidine in the NMP solution. Peptide cleavage from the resin of the amino acid side chains was carried out with trifluoroacetic acid (TFA)/$H_2O$ (95:5 v/v) for 3 h. The resin was washed with TFA, and the filtrates were partially evaporated. The crude products were precipitated with diethyl ether, collected by centrifugation, dissolved in $H_2O$ and lyophilized. The peptides were analyzed and purified using RP-HPLC on a Shimadzu Shim-pack $C_{18}$ column (250×4.6 mm, 5 μm, 100 Å, flow rate 1 ml/min) on a SCL-10A VP Shimadzu apparatus equipped with UV detector (230 nm).

The amino acid sequences of the multimeric PTDs thus prepared were as follows:

```
Chemically synthesized MPH-1-PTD monomer:
                                  (SEQ ID NO: 15)
YARVRRRGPRR(C);

Chemically synthesized MPH-1-PTD dimer a:
                                  (SEQ ID NO: 16)
YARVRRRGPRRGGYARVRRRGPRRGG(C);

Chemically synthesized MPH-1-PTD dimer b:
                                  (SEQ ID NO: 17)
CGGYARVRRRGPRRGGYARVRRRGPRRGG(C);
and Chemically synthesized MPH-1-PTD trimer:
                                  (SEQ ID NO: 18)
YARVRRRGPRRGYARVRRRGPRRGYARVRRRGPRRG(C).
```

Example 2

Recombinant Multimeric and/or Spacer-Incorporated PTD—Soluble Expression

Although the chemical synthesis of a multimeric PTD is a relatively simple process, the preparation of large multimeric PTDs by chemical synthesis may be limited by technical and economic restraints. For this reason, oligomers of up to a dimer were prepared through chemical synthesis in combination with recombinant protein technology, and oligomers larger than a tetramer and the spacer-incorporated PTD were prepared as recombinant proteins. The vectors prepared for the expression of the recombinant proteins of the present invention are shown in FIG. 2.

Because PTDs are short peptides with a strong positive charge, they tend to be degraded easily when they are expressed alone. Thus, various PTDs and spacer-incorporated PTDs were constructed by preparing a fusion protein with ubiquitin (UB), purifying the prepared fusion protein and then cleaving the purified fusion protein with ubiquitin protease (UBP) (shown in FIG. 3).

The multimeric and/or spacer-incorporated PTDs comprising a spacer were prepared as N-terminal UB fusion proteins or non-fusion proteins. Because UB used as spacer can be cleaved by UBP, the carboxyl-terminal residue Gly of the UB spacer was substituted with Val to prevent cleavage by UBP. This mutated domain was represented as UB(v) (shown in FIG. 2). When UB is located at the C-terminus like PTD(2) UB, wild-type UB was used because a C-terminal UB cannot be cleaved by UBP.

Figure 3:
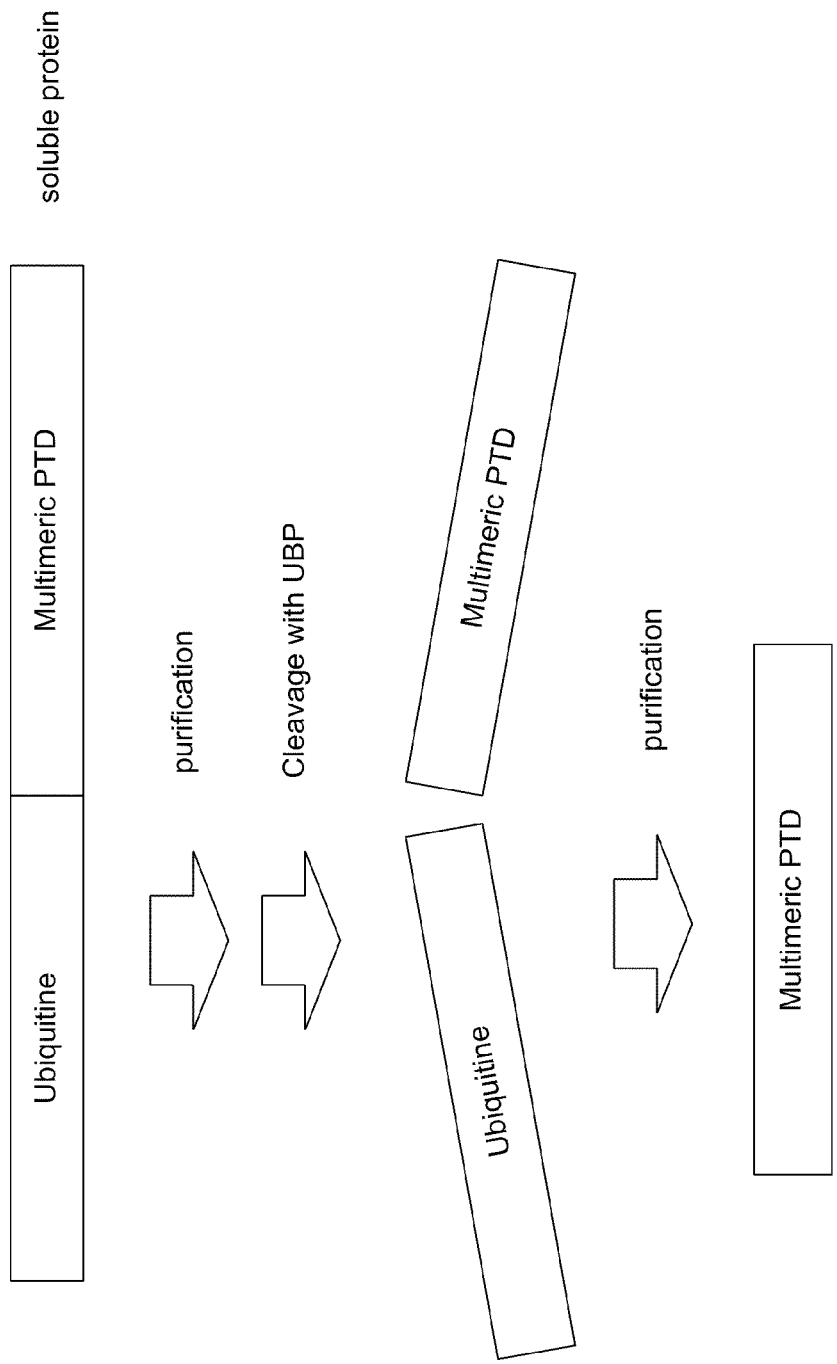
FIG. 3 shows the process to purify a multimeric and/or spacer-incorporated PTD as a soluble protein when it is expressed as an N-terminal fusion protein with ubiquitin.

*E. coli* (BL21) were transformed by the plasmids of FIGS. 2 and 3 according to the conventional heat shock method (Sambrook et al., Molecular cloning $2^{nd}$ Ed.). Recombinant protein expression was induced by the addition of IPTG. After 2-8 hours of induction, cells were harvested by centrifugation, and the cell pellet was resuspended with the appropriate lysis buffer. The cell suspension was sonicated for 20 mins and clarified by centrifugation. The supernatant was loaded on an ion exchange chromatography column (SP FF, GE Healthcare) for the purification of recombinant protein. Because the Arg residue of PTD has a positive charge in neutral pH, the recombinant protein has a high pI value. Therefore recombinant protein was eluted at high conductivity on SP FF column while most of *E. coli* host protein was not bound on SP FF resin at that high conductivity. The selected N-terminal UB fusion or non-fusion protein in IEX was purified with reversed phase high-performance liquid chromatography (RP-HPLC) for higher purity, and then lyophilized.

In the case of a UB-fusion protein, the lyophilized fusion protein was resuspended in appropriate buffer and UBP was added to induce cleavage between UB and PTDs. Subsequently, the multimeric and/or spacer-incorporated PTDs were purified with RP-HPLC and then lyophilized.

The amino acid sequences of the multimeric and/or spacer-incorporated PTDs thus prepared are as follows:

```
Recombinant MPH-1-PTD dimer:
                                  (SEQ ID NO:19)
YRFYARVRRRGPRRGGARFYARVRRRGPRRGGARV(C);

Recombinant MPH-1-PTD tetramer:
                                  (SEQ ID NO:20)
YRFYARVRRRGPRRGGARFYARVRRRGPRRGGARFYARVRRRGPRRGGAR
FYARVRRRGPRRGGARV(C);

Recombinant MPH-1-PTD octamer:
                                  (SEQ ID NO:21)
YRFYARVRRRGPRRGGARFYARVRRRGPRRGGARFYARVRRRGPRRGGAR
FYARVRRRGPRRGGYRFYARVRRRGPRRGGARFYARVRRRGPRRGGARFY
ARVRRRGPRRGGARFYARVRRRGPRRGGARV(C);

Recombinant Penetratin-UB(v) + MPH(2):
                                  (SEQ ID NO:52)
RQIKIWFQNRRMKWKKGGGQIFVKTLTGKTITLEVESSDTIDNVKSKIQD
KEGIPPDQQRLIFAGKQLEDGRTLSDYNIQKESTLHLVLRLRGVSRVYAR
VRRRGPRRGGARFYARVRRRGPRRGGARV(C);

Recombinant Penetratin-UB(v) + MPH(4):
                                  (SEQ ID NO:58)
RQIKIWFQNRRMKWKKGGGQIFVKTLTGKTITLEVESSDTIDNVKSKIQD
KEGIPPDQQRLIFAGKQLEDGRTLSDYNIQKESTLHLVLRLRGVSRVYAR
VRRRGPRRGGARFYARVRRRGPRRGGARFYARVRRRGPRRGGARFYARVR
RRGPRRGGARV(C);

Recombinant Sim-2-UB(v) + PTD(Hph-1) - (2):
                                  (SEQ ID NO:59)
AKAARQAARGGGQIFVKTLTGKTITLEVESSDTIDNVKSKIQDKEGIPPD
QQRLIFAGKQLEDGRTLSDYNIQKESTLHLVLRLRGVSRVYARVRRRGPR
RGGARFYARVRRRGPRRGGARV(C);

Recombinant Sim-2-UB(v) + PTD (Hph-1) - (4):
                                  (SEQ ID NO:60)
AKAARQAARGGGQIFVKTLTGKTITLEVESSDTIDNVKSKIQDKEGIPPD
QQRLIFAGKQLEDGRTLSDYNIQKESTLHLVLRLRGVSRVYARVRRRGPR
RGGARFYARVRRRGPRRGGARFYARVRRRGPRRGGARFYARVRRRGPRRG
GARV(C);

Recombinant PTD(2)UB:
                                  (SEQ ID NO:44)
YARVRRRGPRRGGARFYARVRRRGPRRGGQIFVKTLTGKTITLEVESSDT
DNVKSKIQDKEGIPPDQQRLIFAGKQLEDGRTLSDYNIQKESTLHLVLRL
RGG_;
and Recombinant PTD(4)UB:
                                  (SEQ ID NO:46)
YRFYARVRRRGPRRGGARFYARVRRRGPRRGGARFYARVRRRGPRRGGAR
```

-continued

FYARVRRRGPRRGGNRVQIFVKTLTGKTITLEVEPSDTIENVKAKIQDKE
GIPPDQQRLIFAGKQLEDGRTLSDYNIQKESTLHLVLRLRGG.

Example 3

Enlargement of a Multimeric PTD by Conjugation

Figure 5:
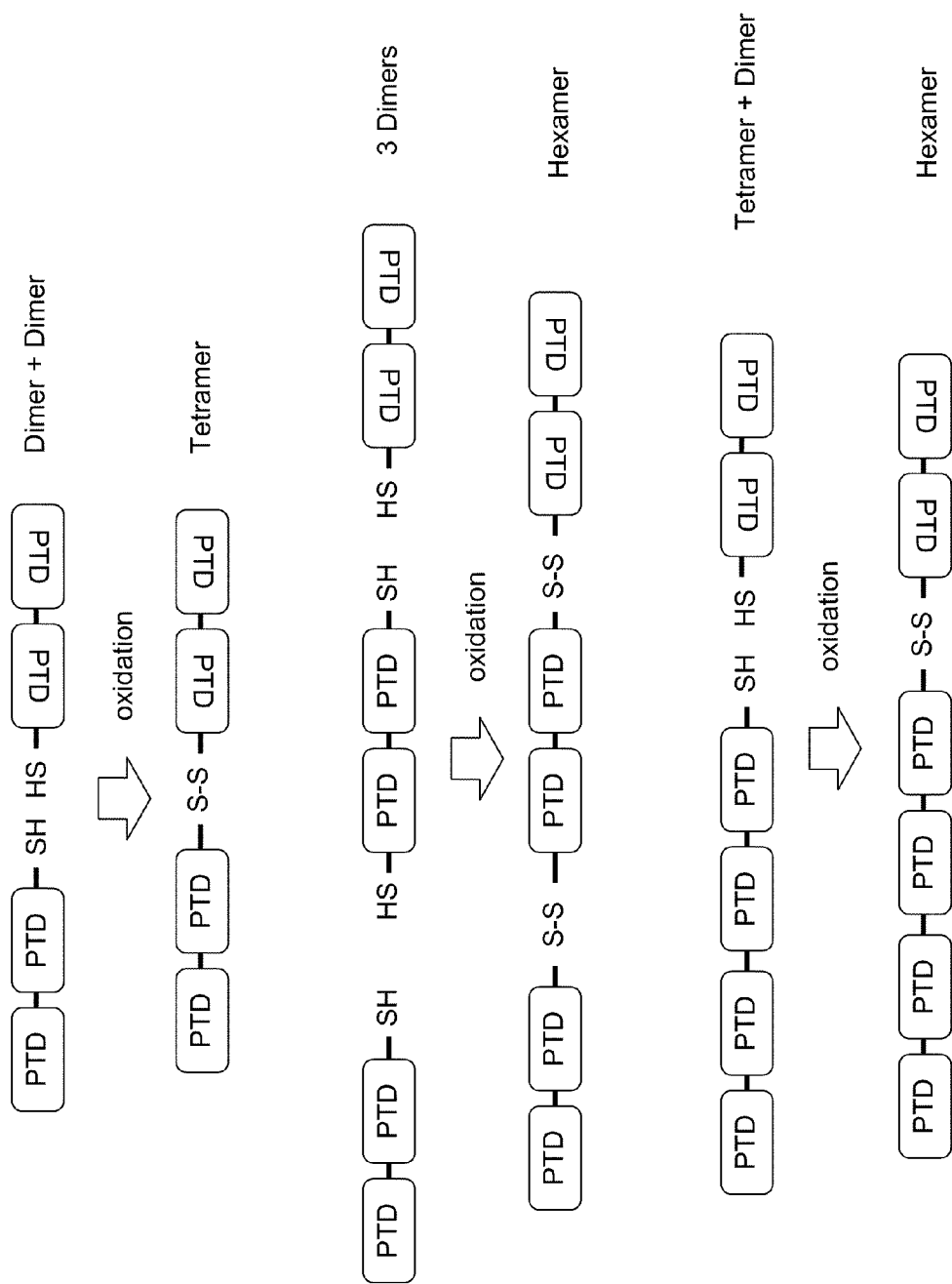
FIG. 5 shows the process to synthesize a PTD tetramer from two PTD dimers, and a PTD hexamer from a PTD tetramer and a PTD dimer by conjugation through a disulfide bond.

To increase the size of a multimeric PTD, a cysteine residue is placed at either or both terminal ends of a PTD such that a disulfide bond can be formed between two PTD molecules. For example, when two PTD dimers with cysteines are linked through a disulfide bond, a tetramer will be formed, and when a dimer and a tetramer are linked, a hexamer will be formed (see FIG. 5).

The induction of a disulfide bond is performed using an air oxidation method with slow stirring at low temperature at pH 8-11.

The multimeric PTDs prepared using the above methods are analyzed by N-terminal sequencing and time-of-flight matrix-assisted laser desorption/ionization mass spectrometry (MALDI-TOF).

The strong positive charge of the multimeric PTD can form a complex with the negatively charged sodium dodecyl sulfate, making it difficult to use sodium dodecyl sulfate polyacrylamide gel electrophoresis (SDS-PAGE) to separate the final multimeric PTD product. Also, general PAGE analysis is difficult to perform because of the high pI of the multimeric PTD. For this reason, PAGE analysis of the multimeric PTD is performed after the pH of PAGE is changed and electrodes are connected reversely.

Example 4

Recombinant Multimeric PTD—Insoluble Expression

Figure 4:
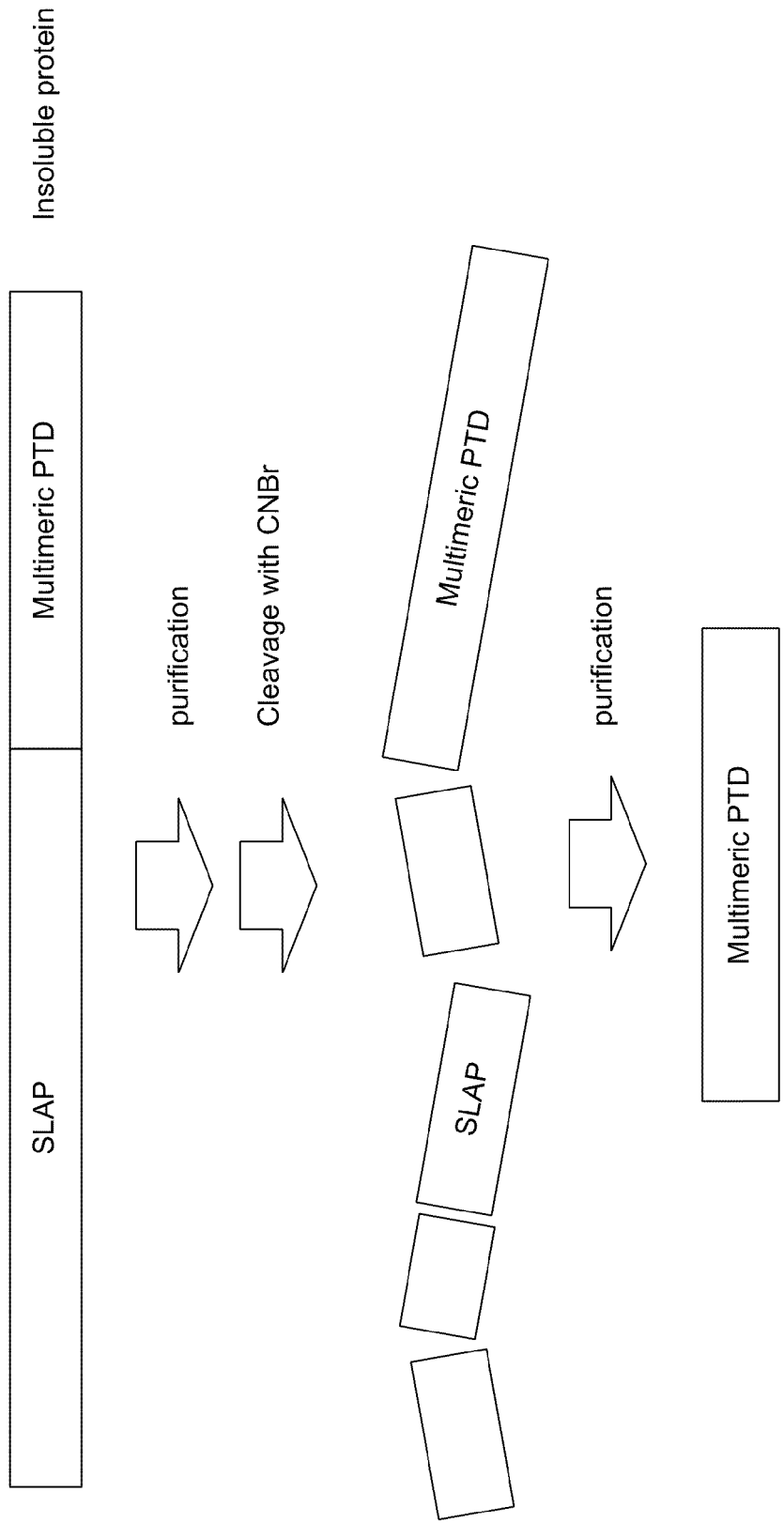
FIG. 4 shows the process to purify a multimeric PTD as an insoluble protein when it is expressed as a fusion protein with Src-like Adaptor Protein (SLAP).

The multimeric PTDs show some toxicity when they are expressed in *E. coli*, and they also tend to be degraded rapidly. Moreover, some PTDs, e.g., TAT-PTD or MPH-1-PTD, contain no methionine. Thus, the present inventors designed a method which comprises insertion of methionine between the fusion partner and the multimeric PTD. Furthermore, the present inventors also designed a method which comprises substituting the fusion partner of the multimeric PTD with a protein which easily aggregates, instead of ubiquitin, for example, Src-like Adaptor Protein (SLAP) or Zeta-chain-associated protein kinase 70 (Zap70). These fusions are useful because proteins that aggregate easily accumulate in inclusion bodies, and therefore, generally have low toxicity. Additionally, they can be protected from degradation and purified in a relatively easy manner. However, inclusion bodies do not dissolve in a moderate and physiological condition. To dissolve inclusion bodies, chaotropic agents—such as urea, guanidine HCl, detergent should be used, or the buffer pH should be at an extreme range. Generally, biological protease cannot be active in such a condition. Therefore, the present inventors adopted a chemical cleavage. Cyanogen bromide (CNBr) cuts peptide bonds specifically at the carboxyl-terminal side of methionine residues. Because many PTDs do not have a methionine residue, a methionine can be inserted at the amino-terminus of a PTD, so that cleavage of fusion protein with CNBr can generate multimeric PTDs (FIG. 4).

For example, a vector similar to that of Example 2, was made for insoluble expression by using SLAP as the fusion partner instead of UB. The construction of the SLAP vector was performed as described in Example 2. Fermentation, induction, harvesting of the cells, and lysis were performed as described in Example 2. After lysis, the cell-suspension was centrifuged, and the supernant was discarded. The remaining inclusion bodies were dissolved in 8M urea buffer and then purified with IEX (SP FF, GE Healthcare). HCl was added in the fraction of the purified fusion-protein in the range of 0.3 to 1 M. CNBr was added for cleavage, and the solution was incubated for 12 hours at room temperature in the dark. After cleavage with CNBr, the multimeric PTD was purified with RP-HPLC in the same manner as described in Example 2, and then lyophilized. Since SLAP has several methionine residues, cleavage of the fusion protein with CNBr generated several fragments showing many peaks in the chromatogram of RP-HPLC, compared with only 2 peaks in the UB-fusion protein.

Example 5

Production of a Nucleic Acid-Multimeric PTD Complex

Figure 1:
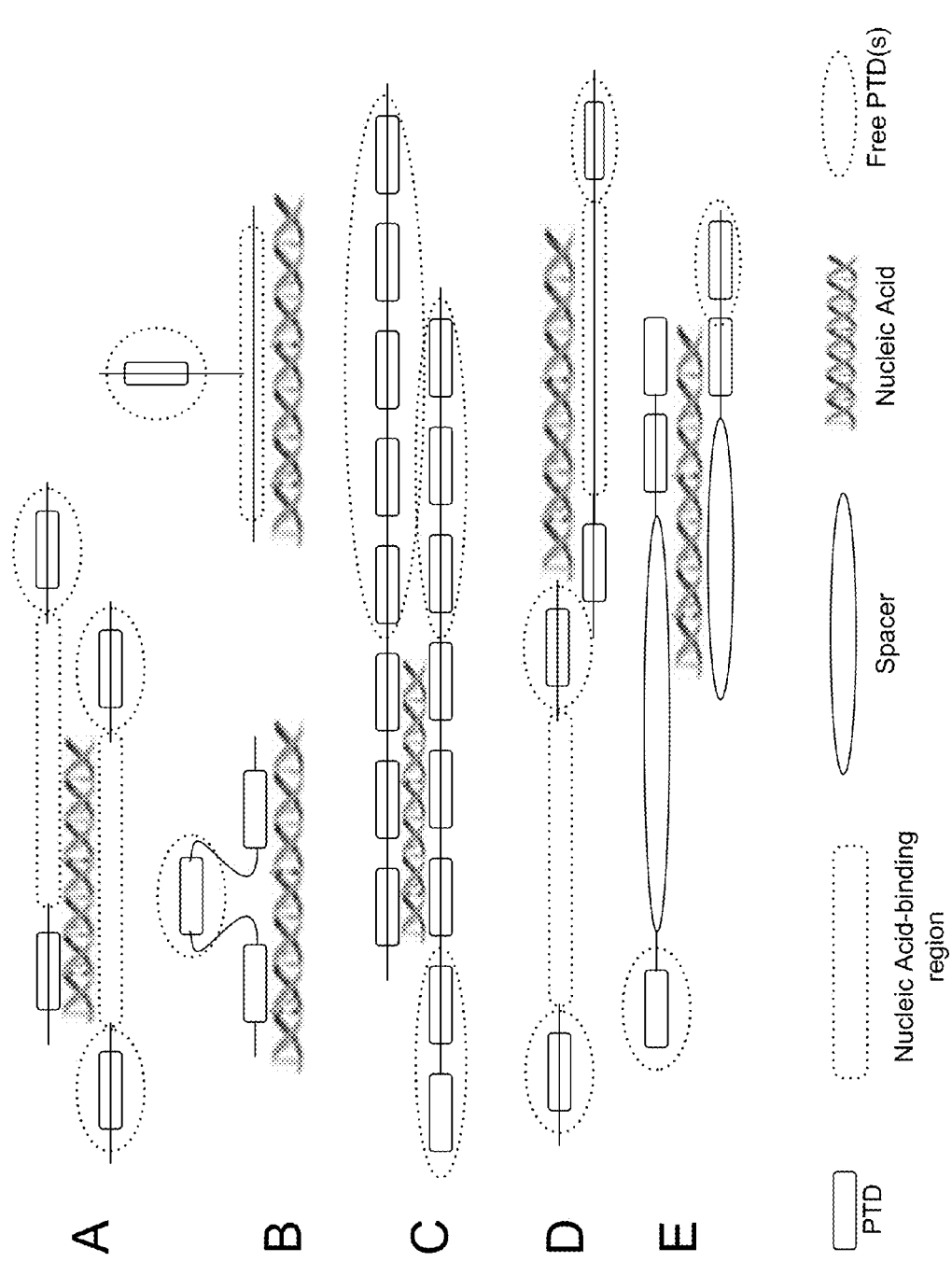
Figure 2A:
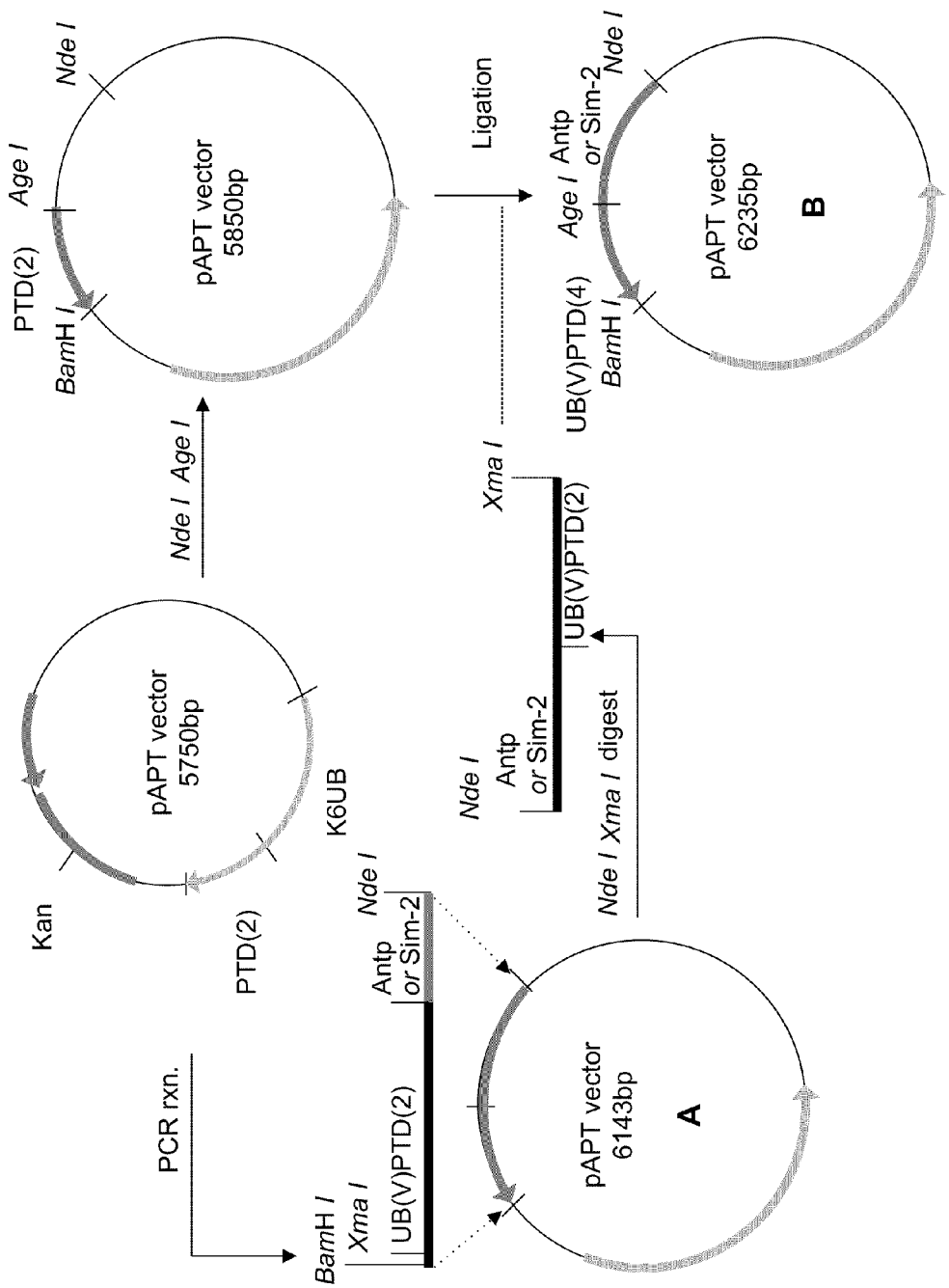
Figure 2B:
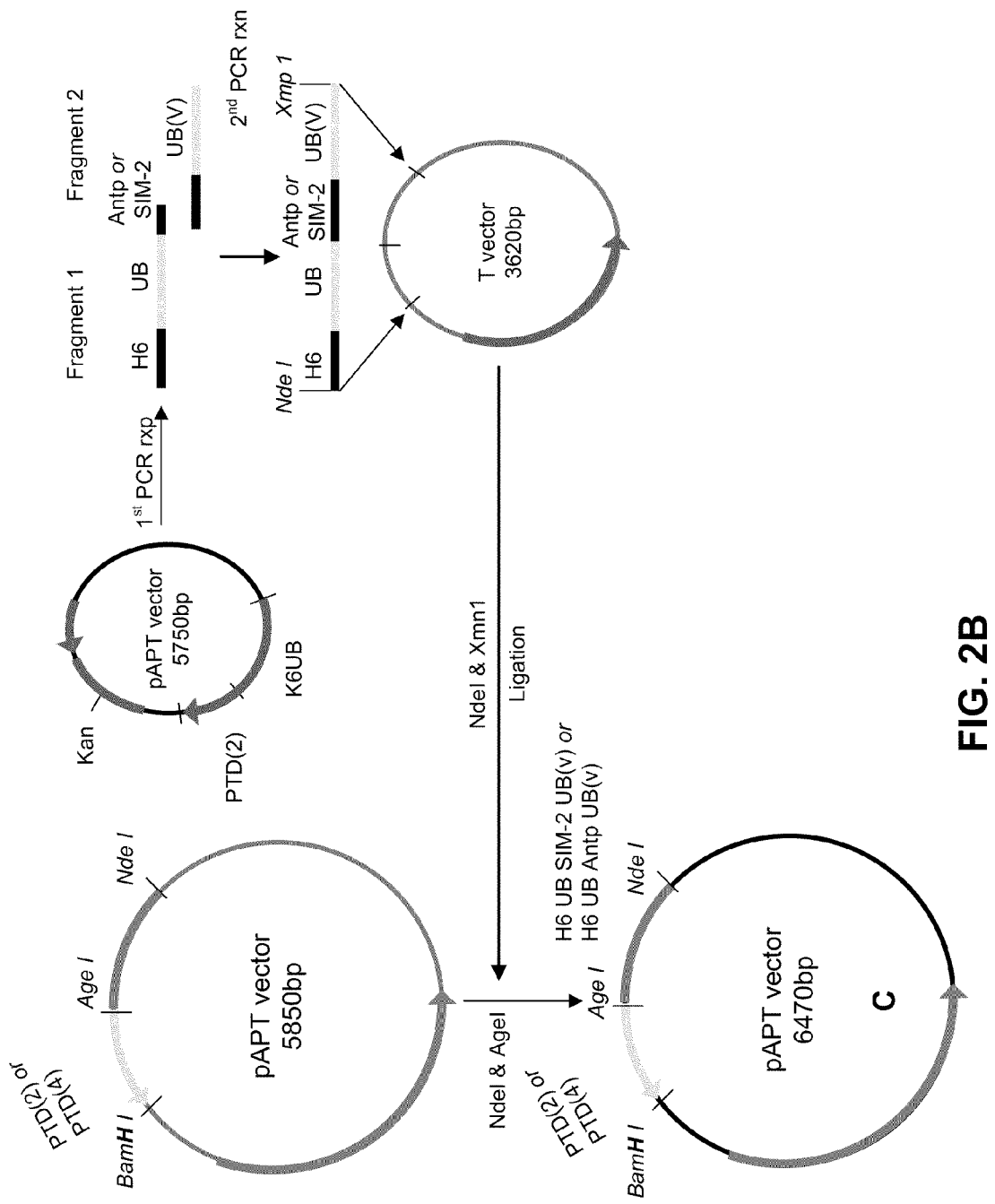
Figure 2C:
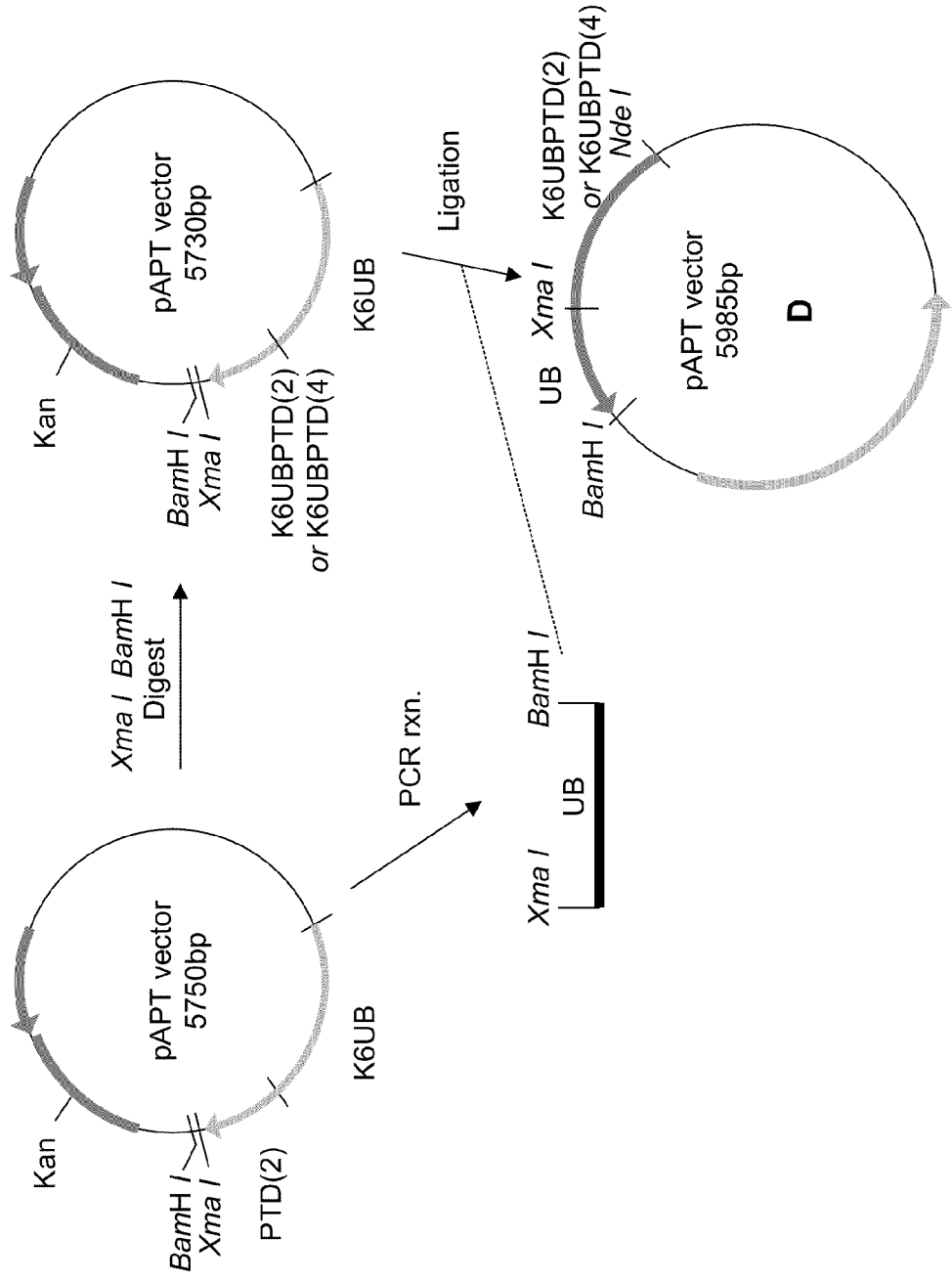
Figure 2D:
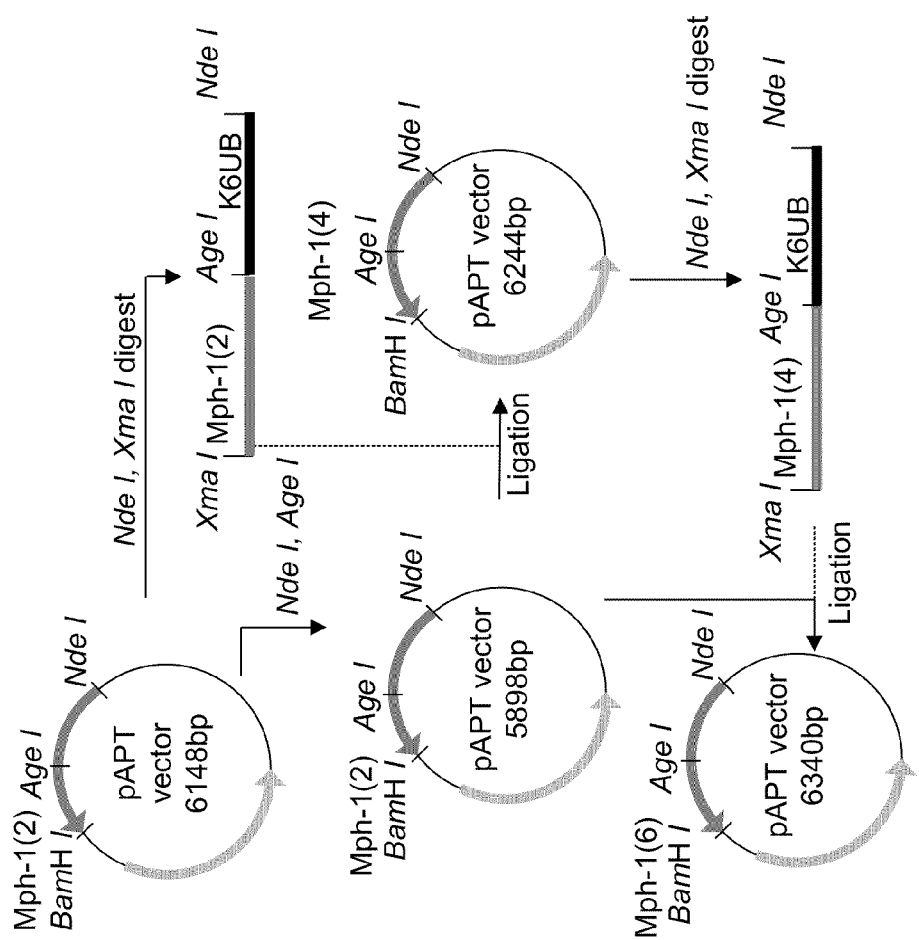
Figure 2E:
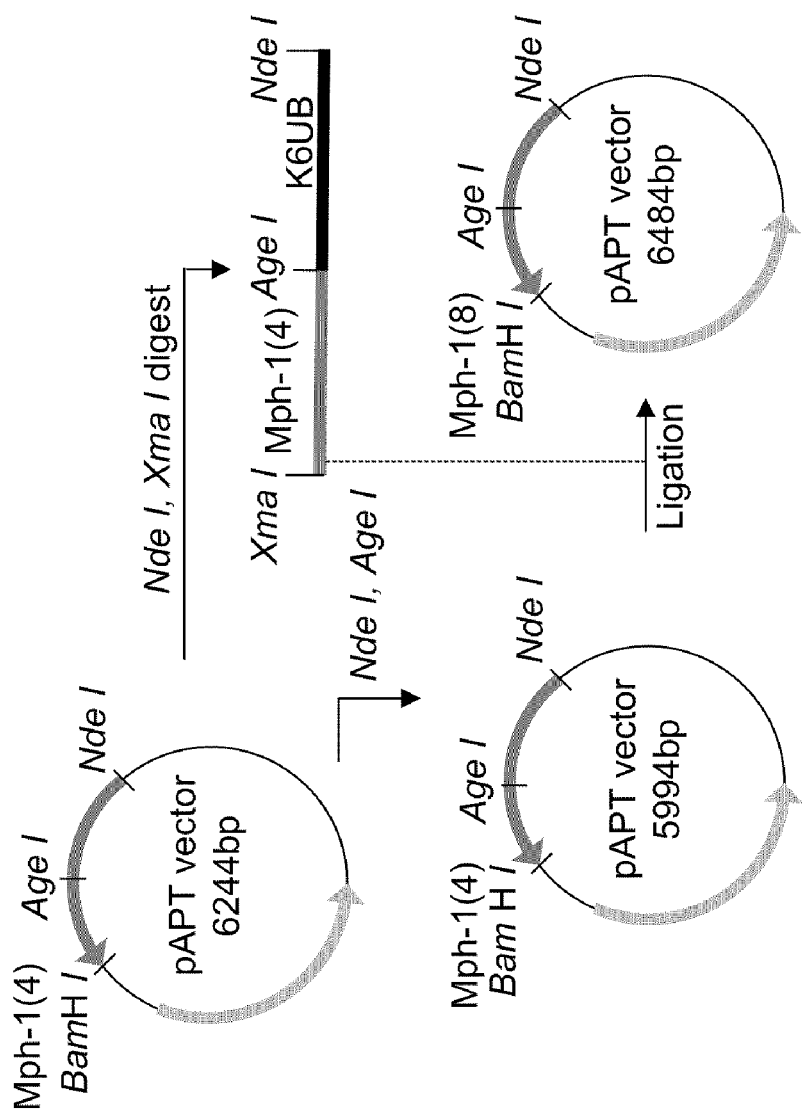

A PTD and a nucleic acid can be complexed through the formation of a stable non-covalent bond between them (FIG. 1). In order to form a nucleic acid-multimeric PTD complex, nucleic acids and multimeric PTDs were mixed at defined ratios. This ratio can be important because an excessive amount of multimeric PTDs can cause insoluble aggregates to form. In contrast, excessive amounts of nucleic acids can decrease the delivery efficiency of the complex. This is demonstrated by the following experiment.

Tetrameric PTD and siRNA were prepared as lyophilized powders. Tetrameric PTD was dissolved in 2×PBS solution, and siRNA was dissolved in deionized water (D.W.). The concentration of PTD and siRNA was 1 uM. The tetrameric PTD of Example 2 was added in the amount of 100, 150, 200, 400, 700 or 1000 ul to a microfuge tube containing 100 ul of the GAPDH siRNA solution. The contents of the tube were thoroughly mixed and allowed to stand for 20 minutes at room temperature. Each mixture was analyzed for the transduction efficiency using a FACS machine. Results are shown in FIG. 9. The mixture became aggregated and showed turbidity when the amount of PTD was 700 ul or more per 100 ul of siRNA. Thus, efficient delivery of a nucleic acid can occur with a ratio of PTD:siRNA of 1:1 to 7:1. In particular, efficient delivery can be achieved with a PTD:siRNA ratio of 3:1. Minimal protein aggregation and efficient delivery of nucleic acids was seen with a PTD:siRNA ratio of 2:1.

Example 6

Production of Nucleic Acid-Multimeric and/or Spacer-Incorporated PTD Conjugates Similar to the method of enlarging multimeric PTDs in Example 4, a thiol group (—SH) is introduced at the 5' end of a nucleic acid to enable conjugation with a cysteine residue at the terminal ends of a multimeric and/or spacer-incorporated PTD. The conjugation is performed using an air oxidation method as described in Example 2.

Figure 6:
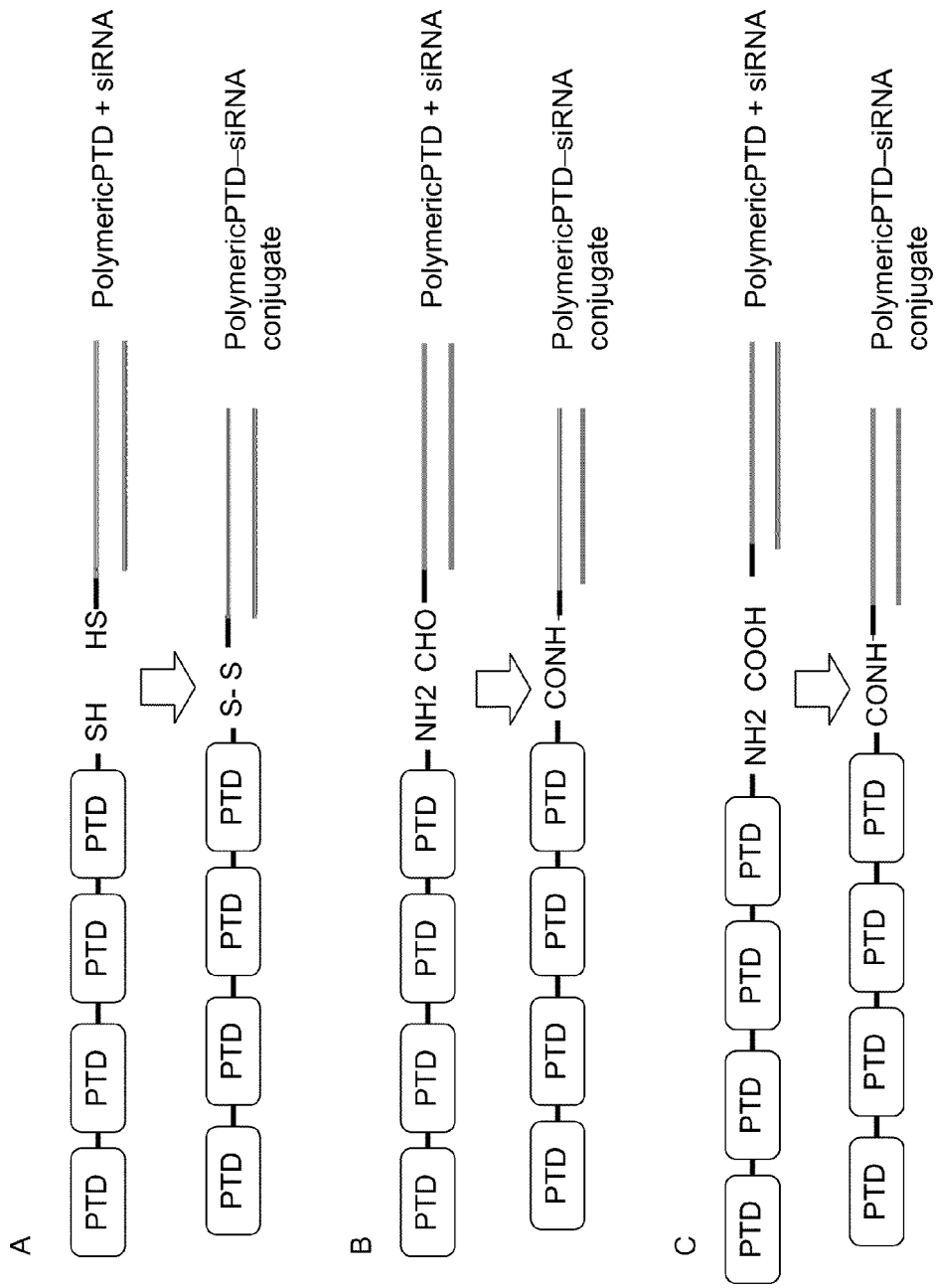
FIG. 6 shows the process to synthesize an siRNA-multimeric PTD by conjugation through different covalent bonds.

Other chemical bonds can also be used to conjugate a multimeric and/or spacer-incorporated PTD and a nucleic acid. For example, introduction of an aldehyde in a nucleic acid can induce the conjugation with the amine group in a peptide. Introduction of a carboxyl group in a nucleic acid can allow formation of an amide bond with the amine group in a peptide (see FIG. 6).

Example 7

Multimeric and/or Spacer-Incorporated PTD-Mediated Intracellular Delivery of siRNA The ability of multimeric and/or spacer-incorporated PTDs to mediate intracellular delivery of siRNAs was evaluated. In these experiments, siRNA was complexed with multimeric and/or spacer-incorporated PTDs, e.g, MPH-1 dimer with spacer (SEQ ID NOs: 44-47), MPH-1 monomer (SEQ ID NO:15), MPH-1 dimer (SEQ ID NO:19), or MPH-1 tetramer (SEQ ID NO:20). MPH-1 monomers were synthesized chemically. Dimers and tetramers were produced recombinantly as described in Example 2. One strand of the siRNA was labeled with carboxyfluorescein (FAM), a fluorescent material, in order to quantitate intracellular siRNA.

siRNA complexed with multimeric and/or spacer-incorporated PTDs were prepared as lyophilized powder. Each multimeric and/or spacer-incorporated PTD was dissolved in 2×PBS solution, and siRNA was dissolved in D.W. The concentration of the siRNA was 1 uM. The concentrations of the monomeric, dimeric and tetrameric PTDs and spacer-incorporated PTDs were 4 uM, 2 uM and 1 uM respectively. The concentration difference between the different PTD multimers was designed to compensate for the differing charge ratios. For the spacer-incorporated PTDs, the concentration of protein depends on the experimental design. The siRNA solution and PTD solution were mixed in equal volume. The final concentration of the siRNA in the mixture was 100 nM.

The siRNA-multimeric PTD complexes were introduced into HeLa cell cultures. After incubation for 0.5-2 h in the $CO_2$ incubator, the medium was removed and the cells were washed with PBS 3 times and collected with a rubber scraper in 1 ml of PBS. The collected cells were centrifuged. The supernatant was discarded, and the cells were resuspended in 1 ml of PBS. This washing step was repeated 3 times.

After washing, the delivery efficiency of siRNA was analyzed using fluorescence-activated cell-sorting (FACS). The results are shown in FIGS. 7 and 8. FIG. 8 shows the height of fluorescence intensity for the 530/30 filter (FL-1H).

As expected, the efficiency of delivery of the monomeric PTD was low. This may be due to the interaction of the siRNA with the monomeric PTD, causing a loss of the PTD's function as a transduction unit. The dimeric PTD showed medium efficiency, and the tetrameric PTD showed the highest efficiency. These results demonstrate that the efficiency of delivery of siRNA increased in proportion with the number of PTDs in the PTD multimers. This indicates that the efficiency may be due to the free PTDs available to function as transduction units.

In the case of the spacer-incorporated PTDs, all the samples showed high transduction-efficiency.

Example 8

The Activity of siRNA Delivered into Cells

The activity of the PTD-delivered siRNAs was also evaluated. In these experiments, the tetrameric MPH-1 PTD (SEQ ID NO:20), as described in Example 7, and the spacer-incorporated PTDs (SEQ ID NOs: 43-60) were used. The tetrameric PTD was complexed with Glyceraldehyde 3-phosphate dehydrogenase (GAPDH) siRNA. The complex was transfected into HeLa cells, and the effect on GAPDH expression was examined. GAPDH expression levels were assessed by measuring GAPDH enzymatic activity.

The spacer-incorporated proteins were complexed with siRNA targeted to Human-protein-kinase C a-subunit (PKCA). The complex was transfected into HeLa cells, and the effect on mRNA level of PKCA was examined. mRNA level of PKCA was measured by quantitative real time PCR. The mixture was introduced into HeLa cells with cultured DMEM medium. After 2 hours, the cells were washed 3 times with fresh medium. After the washes, fresh medium was added to the cells again, and the cells were cultured for 24 hours. After 24 hours-incubation, RNAs were extracted from cells according to the Trizol® (Invitrogen (Carlsbad, Calif.)) instruction manual. cDNAs were synthesized from extracted RNA using High capacity RNA to cDNA kit (Applied Biosystems, Foster city, CA), according to the instruction manual. qRT-PCR was performed using synthesized cDNAs as template, according to the manufacturer's instruction manual (Applied Biosystems 7500 system). The mRNA level of GAPDH was measured for internal compensation.

As shown in FIG. 10, introduction of PKCA siRNA alone did not decrease mRNA level of PKCA. However, when PKCA siRNA was complexed with a spacer-incorporated PTD, mRNA level of PKCA decreased in all samples. This data demonstrates that siRNAs retain inhibition activity when delivered by a spacer-incorporated PTD.

In these experiments, tetrameric PTD was prepared as in Example 2, and mixed with siRNA in the same manner as described in Example 4. The mixture was introduced into HeLa cells with cultured DMEM medium. After 2 h, the cells were washed 3 times with fresh medium. After the washes, fresh medium was added to the cells again, and the cells were cultured for 2 days before GAPDH activity was analyzed according to the KDalert™ (Ambion (Applied Biosystems, Foster city, CA)) instruction manual.

As shown in FIG. 11, introduction of GAPDH siRNA alone did not decrease GAPDH activity. However, when GAPDH siRNA was complexed with tetrameric PTD, GAPDH activity decreased in a dose dependent manner. This data demonstrates that siRNAs retain activity when delivered by tetrameric PTD.

Example 9

Multimeric PTD-Mediated Intracellular Delivery of a DNA Vector

The ability of a multimeric PTD to deliver a DNA vector into HeLa cells was also evaluated. An enhanced green fluorescent protein (EGFP) encoding vector (pEGFP-N1 (Clontech, Mountain View, Calif.)) was used for these experiments.

Tetrameric PTD was prepared as described in Example 2, and a DNA vector was prepared using a DNA prep Kit (Promega, Madison, Wis.). PTD was dissolved in 2×PBS to a concentration of 0.4 mg/ml. The concentration of DNA was adjusted to 0.1 mg/ml with D.W. The DNA solution and PTD solution were mixed in equal volume. After 30 minutes of incubation at room temperature, 20 ul of the mixture was added drop wise into the medium of a 6 mm culture dish. After transduction of the DNA vector into the cells, the cells were incubated for 48 hours to allow for the expression of EGFP. The fluorescence of EGFP was measured by FACS to determine the delivery efficiency of the DNA vector. Similar transfections were done using lipofectamine 2000™ (Invitrogen, Carlsbad, Calif.) transfection reagent, to serve as a positive control.

As shown in FIG. 12, the efficiency of DNA transfection was higher with tetrameric PTD than with lipofectamine. FIG. 12 shows the height of fluorescence intensity for the 530/30 filter (FL-1H).

What is claimed is:

1. A complex or conjugate comprising a nucleic acid sequence complexed or conjugated to a nucleic acid binding molecule, wherein the nucleic acid binding molecule comprises one or more spacer-incorporated protein-transduction domains (PTDs) which comprise one or more PTDs and one or more spacers wherein said spacer comprises one or more amino acid sequences that do not bind said nucleic acid, and wherein the spacer-incorporated PTD comprises the sequence of SEQ ID NO:59.

2. The complex or conjugate of claim 1, wherein the nucleic acid sequence is a single-stranded nucleic acid which comprises a phosphate backbone.

3. The complex or conjugate of claim 1, wherein the spacer-incorporated PTDs comprise two or more, three or more, four or more, or five or more PTDs.

4. The complex or conjugate of claim 2, wherein the single-stranded nucleic acid is selected from the group consisting of: shRNA, antisense RNA, and cDNA.

5. The complex or conjugate of claim 1, wherein the spacer-incorporated protein-transduction domain (PTD) is selected from the group consisting of: homomeric PTD and heteromeric PTD.

6. The complex or conjugate of claim 1, wherein the nucleic acid binding molecule further comprises one or more nucleic acid binding regions.

7. The complex or conjugate of claim 6, wherein the nucleic acid binding region comprises cationic substances.

8. The complex or conjugate of claim 7, wherein the cationic substances are selected from the group consisting of: polylysine, polyarginine, and polyethylenimine.

9. The complex or conjugate of claim 8, wherein the polylysine is selected from the group consisting of: poly-L-lysine and poly-D-lysine.

10. The complex or conjugate of claim 1, wherein the nucleic acid complexed or conjugated with the nucleic binding molecule forms a nanoparticle.

11. The complex or conjugate of claim 1, wherein the complex or conjugate is soluble.

12. The complex or conjugate of claim 1, wherein the nucleic acid is a double-stranded RNA, and wherein one of the strands is substantially complementary to a target gene.

13. The complex or conjugate of claim 12, wherein the double-stranded RNA molecule is selected from the group consisting of: siRNA, miRNA, an engineered RNA precursor, and shRNA.

14. The complex or conjugate of claim 1, wherein the nucleic acid sequence is a double-stranded nucleic acid.

15. A composition comprising the complex or conjugate of claim 1.

16. The complex or conjugate of claim 1, wherein at least one spacer consists of the Fc domain of an antibody.

17. A complex or conjugate comprising a nucleic acid sequence complexed or conjugated to a nucleic acid binding molecule, wherein the nucleic acid binding molecule comprises one or more spacer-incorporated protein-transduction domains (PTDs) which comprise one or more PTDs and one or more spacers, wherein said spacer comprises one or more amino acid sequences that do not bind said nucleic acid, and wherein the spacer-incorporated PTD comprises a sequence that is at least 90% identical to the sequence of SEQ ID NO:59.

18. The complex or conjugate of claim 17, wherein the spacer-incorporated PTD comprises a sequence that is at least 95% identical to the sequence of SEQ ID NO:59.

19. The complex or conjugate of claim 18, wherein the spacer-incorporated PTD comprises a sequence that is at least 96% identical to the sequence of SEQ ID NO:59.

20. The complex or conjugate of claim 19, wherein the spacer-incorporated PTD comprises a sequence that is at least 97% identical to the sequence of SEQ ID NO:59.

21. The complex or conjugate of claim 20, wherein the spacer-incorporated PTD comprises a sequence that is at least 98% identical to the sequence of SEQ ID NO:59.

22. The complex or conjugate of claim 21, wherein the spacer-incorporated PTD comprises a sequence that is at least 99% identical to the sequence of SEQ ID NO:59.

23. The complex or conjugate of claim 17, wherein the spacer-incorporated PTD is capable of delivering a polypeptide into a cell.

24. The complex or conjugate of claim 18, wherein the spacer-incorporated PTD is capable of delivering a polypeptide into a cell.

25. The complex or conjugate of claim 19, wherein the spacer-incorporated PTD is capable of delivering a polypeptide into a cell.

26. The complex or conjugate of claim 20, wherein the spacer-incorporated PTD is capable of delivering a polypeptide into a cell.

27. The complex or conjugate of claim 21, wherein the spacer-incorporated PTD is capable of delivering a polypeptide into a cell.

28. The complex or conjugate of claim 22, wherein the spacer-incorporated PTD is capable of delivering a polypeptide into a cell.

29. The complex or conjugate of claim 1, wherein the spacer-incorporated PTD is capable of delivering a polypeptide into a cell.

* * * * *